US009683269B2

(12) United States Patent
Gottwein et al.

(10) Patent No.: US 9,683,269 B2
(45) Date of Patent: *Jun. 20, 2017

(54) INFECTIOUS HEPATITIS C VIRUSES OF GENOTYPE 3A AND 4A AND USES THEREOF

(71) Applicants: Hvidovre Hospital, Hvidovre (DK); The United States of America, as Represented by the Secretary, Department of Health and Human Services, Washington, DC (US)

(72) Inventors: Judith M. Gottwein, Frederiksberg (DK); Troels Kasper Hoyer Scheel, Copenhagen (DK); Robert Purcell, Bethesda, MD (US); Jens Bukh, Praestø (DK)

(73) Assignees: Hvidovre Hospital, Hvidovre (DK); The United States of America, As Represented by the Secretary, Department of Health and Human Services, Washington, DC (US)

( * ) Notice: Subject to any disclaimer, the term of this patent is extended or adjusted under 35 U.S.C. 154(b) by 40 days.

This patent is subject to a terminal disclaimer.

(21) Appl. No.: 14/514,023

(22) Filed: Oct. 14, 2014

(65) Prior Publication Data
US 2015/0105290 A1    Apr. 16, 2015

Related U.S. Application Data

(63) Continuation of application No. 13/499,663, filed as application No. PCT/DK2010/050236 on Sep. 16, 2010, now Pat. No. 8,946,398.

(30) Foreign Application Priority Data

Oct. 2, 2009  (DK) ................................ 2009 70143

(51) Int. Cl.
*C12N 7/00* (2006.01)
*C12Q 1/70* (2006.01)
*C12N 15/86* (2006.01)
*G01N 33/50* (2006.01)

(52) U.S. Cl.
CPC ............... *C12Q 1/707* (2013.01); *C12N 7/00* (2013.01); *C12N 15/86* (2013.01); *G01N 33/5008* (2013.01); *C12N 2770/24221* (2013.01); *C12N 2770/24243* (2013.01)

(58) Field of Classification Search
None
See application file for complete search history.

(56) References Cited

U.S. PATENT DOCUMENTS

| 8,889,848 | B2 | 11/2014 | Delaney, IV et al. |
| 8,889,849 | B2 | 11/2014 | Delaney, IV et al. |
| 8,946,398 | B2 * | 2/2015 | Gottwein ................. C12N 7/00 435/5 |
| 2004/0166488 | A1 | 8/2004 | Tang et al. |

FOREIGN PATENT DOCUMENTS

| WO | 2005/118626 A2 | 12/2005 |
| WO | 2008/125117 A1 | 10/2008 |
| WO | 2008/125119 A1 | 10/2008 |
| WO | 2009/022236 A2 | 2/2009 |

OTHER PUBLICATIONS

GenBank: ADF97231.1 polyprotein [Hepatitis C virus S52] 2010.*
Saeed et al., "Efficient Replication of Genotype 3a and 4a Hepatitis C Virus Replicons in Human Hepatoma Cells", Antimicrobial Agents and Chemotherapy, Oct. 2012, pp. 5365-5373, vol. 56 No. 10.
Peng et al., "Development of Robust Hepatitis C Virus Genotype 4 Subgenomic Replicons", Journal of Gastroenterology, 2013, pp. 59-61.e6, vol. 144, No. 1.
Binder et al, "Development of Hepatitis C Virus (HCV) Chimeric Replicons for Identifying Broad Spectrum NS3 Proteses Inhibitors", Program and Abstracts/Antiviral Research, 2007, pp. A38, A1-A97.
Chamberlain, et al., "Complete Neclotide Sequence of a Type 4 Hepatitis C Virus Variant, the Predominant Genotype in the Middle East", Journal of General Virology, 1997, pp. 1341-1347, vol. 78.
Gottwein et al., "Robust Hepatitis C Genotype 3a Cell Culture Releasing Adapted Intergenotype 3a/2a (S52/JFH1) Viruses", Gastroenterology, 2007, pp. 1614-1626, vol. 133.
Gottwein et al., "Development and Characterization of Hepatitis C Virus Genotype 1-7 Cell Culture Systems: Role of CD81 and Scavenger Receptor Class B Type I and Effect of Antiviral Drugs", Hepatology, 2009, pp. 364-377, vol. 49, No. 2.
Gottwein et al., "Novel Infectious cDNA Clones of Hepatitis C Virus Genotype 3a (Strain S52) abd 4a (Strain ED43): Genetic Analysis and in Vivo Pathogenesis Studies", Journal of Virology, May 2010, pp. 5277-5293, vol. 84, No. 10.
Jensen et al., "Highly Efficient JFH1-Based Cell-Culture System for Hepatitis C Virus Genotype 5a: Failure of Homologous Neutralizing-Antibody Treatment to Control Infection", Journal of Infectious Diseases, Dec. 15, 2008, pp. 1756-1765, vol. 198.

(Continued)

*Primary Examiner* — Michelle S Horning
(74) *Attorney, Agent, or Firm* — Thompson Copburn, LLP; Charles P. Romano

(57) ABSTRACT

The present invention relates to molecular approaches to the production of nucleic acid sequences, which comprises the genome of infectious hepatitis C virus. In particular, the invention provides nucleic acid sequences which comprise the genomes of infectious hepatitis C viruses of either genotype 3a (strain S52) or genotype 4a (strain ED43). The invention therefore relates to the use of the nucleic acid sequences and polypeptides encoded by all or part of the sequences in the development of vaccines and diagnostic assays for HCV and in the development of screening assays for the identification of antiviral agents for HCV. The invention therefore also relates to the use of viral particles derived from laboratory animals infected with S52 and ED43 viruses.

13 Claims, 9 Drawing Sheets

(56) References Cited

OTHER PUBLICATIONS

Kaul et al., "Cell Culture Adaptation of Hepatitis C Virus and in Vivo Viability of an Adapted Variant", Journal of Virology, Dec. 2007, pp. 13168-13179, vol. 81, No. 23.

Kolykhalov et al., "Transmission of Hepatitis C by Intrahepatic Inoculation with Transcribed RNA", Science, Jul. 1997, pp. 570-574, vol. 277.

Lanford et al., "Infectious cDNA Clone of the Hepatitus C Virus Genotype 1 Prototype Sequence", Journal of General Virology, 2001, pp. 1291-1297, vol. 82.

Lindenbach et al., "Complete Replication of Hepatitis C Virus in Cell Culture", Science, Jul. 22, 2005, pp. 623-626, vol. 309.

Lindenbach et al., "Cell Culture-Growth Hepatitis C Virus is Infectious in Vivo and can be Recultured in Vitro", Proceedings of the National Academy of Sciences, Mar. 7, 2006, pp. 3805-3809, vol. 103, No. 10.

Pietschmann et al., "Construction and Characterization of Infectious Intragenotypic and Intergenotypic Hepatitis C Virus Chimeras", Proceedings of the National Academy of Sciences, May 9, 2006, pp. 7408-7413, vol. 103, No. 19.

Scheel et al., "Development of JFH1-Based Cell Culture Systems for Hepatitis C Virus Genotype 4a and Evidence for Cross-Genotype Neutralization", Proceedings of the National Academy of Sciences, Jan. 22, 2008, pp. 997-1002, vol. 105, No. 3.

Timm et al., "Characterization of Full-Length Hepatitis C Virus Genotype 4 Sequences", Journal of Viral Hepatitis, 2007, pp. 330-337, vol. 14.

Wakita et al., "Production of Infectious Hepatitis C Virus in Tissue Culture from a Cloned Viral Genome", Nature Medicine, Jul. 2005, pp. 791-796, vol. 11, No. 7.

Yanagi et al., "Transcripts from a Single Full-Length cDNA Clone of Hepatitis C Virus are Infectious when Directly Transfected into the Liver of a Chimpanzee", Proceedings of the National Academy of Sciences, Aug. 1997, pp. 8738-8743, vol. 94.

Yanagi et al., "Transcripts of a Chimeric cDNA Clone of Hepatitis C Virus Genotype 1b are Infectious in Vivo", Virology, 1998, pp. 161-172, vol. 244.

Yanagi et al., "Hepatitis C Virus: An Infectious Molecular Clone of a Second Major Genotype (2a) and Lack of Viability of Intertypic 1a and 2a Chimeras", Virology, 1999, pp. 250-263, vol. 262.

Yi et al., "Compensatory Mutations in E1, p7, NS2, and NS3 Enhance Yields of Cell Culture-Infectious Intergenotypic Chimeric Hepatitis C Virus", Journal of Virology, Jan. 2007, pp. 629-638, vol. 81, No. 2.

Zhong et al., "Robust Hepatitis C Virus Infection in Vitro", Proceedings of the National Academy of Sciences, Jun. 28, 2005, pp. 9294-9299, vol. 102, No. 26.

Farci, "New Insights into the HCV Quasispecies and Compartmentalization", Seminars in Liver Disease, 2011, pp. 356-374, vol. 31, No. 4.

Wyatt et al., "Immunity in Chimpanzees Chronically Infected with Hepatitis C Virus: Role of Minor Quasispecies in Reinfection", Journal of Virology, Mar. 1998, pp. 1725-1730, vol. 72, No. 3.

UniProtKB/Swiss-Prot: o92933 submitted by Shukla et al., 1998.

Tellinghuisen et al., "The NS5A Protein of Hepatitis C Virus is a Zinc Metalloprotein", The Journal of Biological Chemistry, Nov. 19, 2004, pp. 48576-48587, vol. 279 No. 47.

Bukh et al., "Mutations that Permit Efficient Replication of Hepatitis C Virus RNA in Huh-7 Cells Prevent Productive Replication in Chimpanzees", Proceedings of the National Academy of Sciences (PNAS) of the United States of America, Oct. 29, 2002 pp. 14416-14421, vol. 99 No. 22.

Bartenschlager et al., "Replication of the Hepatitis C Virus in Cell Culture", Antiviral Research, 2003, pp. 31-102, vol. 60.

Blight et al, "Efficient Replication of Hepatitis C Virus Genotype 1a RNAs in Cell Culture", Journal of Virology, Mar. 2003, pp. 3181-3190, vol. 77, No. 5.

Forns et al., "Quasispecies in Viral Persistence and Pathogenesis of Hepatitis C Virus", Trends in Microbiology, October 1999, pp. 402-410, vol. 7, No. 10.

Yi et al., "3' Nontranslated RNA Signals Required for Replication of Hepatitis C Virus RNA", Journal of Virology, Mar. 2003, pp. 3557-3568, vol. 77, No. 6.

\* cited by examiner

| Genomic region | nt position(1) | GH ≥1 clone | | GH ≥ 2 clone | | aa position(1) | GH ≥1 clone | |
|---|---|---|---|---|---|---|---|---|
| | | # | % | # | % | | # | % |
| 5'UTR | 24-339 | 3 | 0,9 | 0 | 0,0 | | | |
| Core | 340-912 | 7 | 1,2 | 3 | 0,5 | 1-191 | 2 | 1,0 |
| E1 | 913-1488 | 18 | 3,1 | 4 | 0,7 | 192-383 | 4 | 2,1 |
| E2 | 1489-2595 | 41 | 3,7 | 8 | 0,7 | 384-752 | 15 | 4,1 |
| HVR1 | 1489-1569 | 4 | 4,9 | 1 | 1,2 | 384-410 | 0 | 0,0 |
| p7 | 2596-2784 | 8 | 4,2 | 1 | 0,5 | 753-815 | 3 | 4,8 |
| NS2 | 2785-3435 | 26 | 4,0 | 10 | 1,5 | 816-1032 | 9 | 4,1 |
| NS3 | 3436-5328 | 34 | 1,8 | 6 | 0,3 | 1033-1663 | 12 | 1,9 |
| NS4A | 5329-5490 | 4 | 2,5 | 3 | 1,9 | 1664-1717 | 1 | 1,9 |
| NS4B | 5491-6273 | 10 | 1,3 | 4 | 0,5 | 1718-1978 | 2 | 0,8 |
| NS5A | 6274-7629 | 22 | 1,6 | 14 | 1,0 | 1979-2430 | 11 | 2,4 |
| NS5B | 7630-9402 | 29 | 1,6 | 10 | 0,6 | 2431-3021 | 8 | 1,4 |
| ORF | 340-9402 | 199 | 2,2 | 63 | 0,7 | 1-3021 | 67 | 2,2 |

Fig. 3

| Genomic region | nt position(1) | Genbank accession number | | | | | |
|---|---|---|---|---|---|---|---|
| | | D17763 (NZL1) | | D28917 (HCV-K3a/650) | | DQ437509 (452) | |
| | | # | % | # | % | # | % |
| Core | 340-912 | 11 | 1,9 | 31 | 5,4 | 14 | 2,5 |
| E1 | 913-1488 | 27 | 4,7 | 34 | 5,9 | 36 | 6,3 |
| E2 | 1489-2595 | 94 | 8,5 | 108 | 9,7 | 118 | 10,6 |
| HVR1 | 1489-1569 | 25 | 30,9 | 24 | 29,6 | 21 | 25,9 |
| p7 | 2596-2784 | 10 | 5,3 | 13 | 6,9 | 12 | 6,3 |
| NS2 | 2785-3435 | 39 | 6,0 | 45 | 6,9 | 36 | 5,5 |
| NS3 | 3436-5328 | 80 | 4,2 | 112 | 5,9 | 105 | 5,6 |
| NS4A | 5329-5490 | 10 | 6,2 | 11 | 6,8 | 11 | 6,8 |
| NS4B | 5491-6273 | 32 | 4,1 | 52 | 6,7 | 53 | 6,8 |
| NS5A | 6274-7629 | 71 | 5,3 | 85 | 6,3 | 104 | 7,7 |
| NS5B | 7630-9402 | 59 | 3,3 | 95 | 5,3 | 87 | 4,9 |
| ORF | 340-9402 | 434 | 4,8 | 587 | 6,5 | 577 | 6,3 |

| Genomic region | aa position(1) | Genbank accession number | | | | | |
|---|---|---|---|---|---|---|---|
| | | D17763 (NZL1) | | D28917 (HCV-K3a/650) | | DQ437509 (452) | |
| | | # | % | # | % | # | % |
| Core | 1-191 | 1 | 0,5 | 9 | 4,7 | 1 | 0,5 |
| E1 | 192-383 | 6 | 3,1 | 12 | 6,2 | 11 | 5,7 |
| E2 | 384-752 | 39 | 10,6 | 42 | 11,4 | 44 | 11,9 |
| HVR1 | 384-410 | 17 | 63,0 | 11 | 40,7 | 12 | 44,4 |
| p7 | 753-815 | 3 | 4,8 | 3 | 4,8 | 5 | 7,9 |
| NS2 | 816-1032 | 8 | 3,7 | 17 | 7,8 | 8 | 3,7 |
| NS3 | 1033-1663 | 17 | 2,7 | 24 | 3,8 | 20 | 3,2 |
| NS4A | 1664-1717 | 3 | 5,6 | 4 | 7,4 | 3 | 5,6 |
| NS4B | 1718-1978 | 6 | 2,3 | 12 | 4,6 | 5 | 1,9 |
| NS5A | 1979-2430 | 21 | 4,6 | 27 | 6,0 | 27 | 6,0 |
| NS5B | 2431-3021 | 6 | 1,0 | 27 | 4,6 | 17 | 2,9 |
| ORF | 1-3021 | 110 | 3,6 | 177 | 5,9 | 141 | 4,7 |

Fig. 4

| Genomic region | nt position(1) | GH≥1 clone # | GH≥1 clone % | GH≥2 clones # | GH≥2 clones % | aa position(1) | GH≥1 clone # | GH≥1 clone % | GH≥2 clc # |
|---|---|---|---|---|---|---|---|---|---|
| 5'UTR | 1-340 | 6 | 1,8 | 0 | 0 | | | | |
| Core | 341-913 | 13 | 2,3 | 0 | 0,0 | 1-191 | 6 | 3,1 | 0 |
| E1 | 914-1489 | 12 | 2,1 | 0 | 0,0 | 192-383 | 8 | 4,2 | 0 |
| E2 | 1490-2578 | 18 | 1,7 | 1 | 0,1 | 384-746 | 7 | 1,9 | 0 |
| HVR1 | 1490-1570 | 0 | 0,0 | 0 | 0,0 | 384-410 | 0 | 0,0 | 0 |
| p7 | 2579-2767 | 5 | 2,6 | 0 | 0,0 | 747-809 | 3 | 4,8 | 0 |
| NS2 | 2768-3418 | 11 | 1,7 | 0 | 0,0 | 810-1026 | 6 | 2,8 | 0 |
| NS3 | 3419-5311 | 31 | 1,6 | 2 | 0,1 | 1027-1657 | 14 | 2,2 | 0 |
| NS4A | 5312-5473 | 4 | 2,5 | 0 | 0,0 | 1658-1711 | 2 | 3,7 | 0 |
| NS4B | 5474-6256 | 12 | 1,5 | 0 | 0,0 | 1712-1972 | 5 | 1,9 | 0 |
| NS5A | 6257-7591 | 12 | 0,9 | 0 | 0,0 | 1973-2417 | 3 | 0,7 | 0 |
| NS5B | 7592-9364 | 26 | 1,5 | 0 | 0,0 | 2418-3008 | 10 | 1,7 | 0 |
| ORF | 341-9364 | 144 | 1,6 | 3 | 0,0 | 1-3008 | 64 | 2,1 | 0 |

Fig. 5

| Genomic region | nt position(1) | Y11604 (ED43) | | DQ418782 (01-09) | | DQ418783 (02-42) | | DQ418784 (02C) | | DQ418787 (F753) | | DQ418788 (F7157) | | DQ418789 (L835) | |
|---|---|---|---|---|---|---|---|---|---|---|---|---|---|---|---|
| | | # | % | # | % | # | % | # | % | # | % | # | % | # | % |
| Core | 341-913 | 3 | 0,5 | 21 | 3,7 | 20 | 3,5 | 29 | 5,1 | 21 | 3,7 | 19 | 3,3 | 19 | 3,3 |
| E1 | 914-1489 | 4 | 0,7 | 56 | 9,7 | 48 | 8,4 | 60 | 10,4 | 57 | 9,9 | 60 | 10,4 | 56 | 9,7 |
| E2 | 1490-2578 | 5 | 0,5 | 170 | 15,6 | 144 | 13,2 | 155 | 14,3 | 147 | 13,5 | 165 | 15,2 | 155 | 14,3 |
| HVR1 | 1490-1570 | 0 | 0,0 | 31 | 38,3 | 34 | 42,0 | 28 | 34,6 | 36 | 44,4 | 37 | 45,7 | 38 | 46,9 |
| p7 | 2579-2767 | 2 | 1,1 | 26 | 13,8 | 26 | 13,8 | 21 | 11,1 | 26 | 13,8 | 24 | 12,7 | 28 | 14,8 |
| NS2 | 2768-3418 | 9 | 1,4 | 77 | 11,9 | 85 | 13,1 | 87 | 13,4 | 91 | 14,1 | 86 | 13,2 | 75 | 11,6 |
| NS3 | 3419-5311 | 24 | 1,3 | 168 | 8,9 | 175 | 9,2 | 166 | 8,8 | 177 | 9,4 | 171 | 9,0 | 177 | 9,4 |
| NS4A | 5312-5473 | 0 | 0,0 | 11 | 6,8 | 12 | 7,4 | 14 | 8,6 | 15 | 9,3 | 12 | 7,4 | 15 | 9,3 |
| NS4B | 5474-6256 | 18 | 2,3 | 68 | 8,7 | 52 | 6,7 | 56 | 7,2 | 57 | 7,3 | 59 | 7,6 | 65 | 8,3 |
| NS5A | 6257-7591 | 36 | 2,7 | 129 | 9,7 | 119 | 8,9 | 137 | 10,3 | 113 | 8,5 | 120 | 9,0 | 118 | 8,9 |
| NS5B | 7592-9364 | 24 | 1,3 | 131 | 7,3 | 113 | 6,3 | 135 | 7,6 | 128 | 7,2 | 111 | 6,2 | 112 | 6,3 |
| ORF | 341-9364 | 125 | 1,4 | 857 | 9,5 | 794 | 8,8 | 860 | 9,5 | 832 | 9,2 | 827 | 9,2 | 820 | 9,1 |

| Genomic region | aa position(1) | Y11604 (ED43) | | DQ418782 (01-09) | | DQ418783 (02-42) | | DQ418784 (02C) | | DQ418787 (F753) | | DQ418788 (F7157) | | DQ418789 (L835) | |
|---|---|---|---|---|---|---|---|---|---|---|---|---|---|---|---|
| | | # | % | # | % | # | % | # | % | # | % | # | % | # | % |
| Core | 1-191 | 2 | 1,0 | 2 | 1,0 | 3 | 1,6 | 3 | 1,6 | 2 | 1,0 | 2 | 1,0 | 2 | 1,0 |
| E1 | 192-383 | 1 | 0,5 | 11 | 5,7 | 8 | 4,2 | 10 | 5,2 | 11 | 5,7 | 11 | 5,7 | 14 | 7,3 |
| E2 | 384-746 | 1 | 0,3 | 57 | 15,7 | 41 | 11,3 | 46 | 12,7 | 48 | 13,2 | 54 | 14,9 | 53 | 14,6 |
| HVR1 | 384-410 | 0 | 0,0 | 16 | 59,3 | 10 | 37,0 | 10 | 37,0 | 16 | 59,3 | 16 | 59,3 | 15 | 55,6 |
| p7 | 747-809 | 1 | 1,6 | 13 | 20,6 | 10 | 15,9 | 10 | 15,9 | 9 | 14,3 | 9 | 14,3 | 10 | 15,9 |
| NS2 | 810-1026 | 7 | 3,2 | 30 | 13,8 | 28 | 12,9 | 30 | 13,8 | 30 | 13,8 | 30 | 13,8 | 27 | 12,4 |
| NS3 | 1027-1657 | 11 | 1,7 | 21 | 3,3 | 23 | 3,6 | 31 | 4,9 | 26 | 4,1 | 22 | 3,5 | 24 | 3,8 |
| NS4A | 1658-1711 | 0 | 0,0 | 1 | 1,9 | 1 | 1,9 | 1 | 1,9 | 2 | 3,7 | 0 | 0,0 | 1 | 1,9 |
| NS4B | 1712-1972 | 11 | 4,2 | 2 | 0,8 | 3 | 1,1 | 3 | 1,1 | 4 | 1,5 | 4 | 1,5 | 5 | 1,9 |
| NS5A | 1973-2417 | 20 | 4,5 | 27 | 6,1 | 22 | 5,0 | 37 | 8,3 | 21 | 4,7 | 24 | 5,4 | 22 | 5,0 |
| NS5B | 2418-3008 | 13 | 2,2 | 25 | 4,2 | 26 | 4,4 | 30 | 5,1 | 24 | 4,1 | 23 | 3,9 | 22 | 3,7 |
| ORF | 1-3008 | 67 | 2,2 | 189 | 6,2 | 165 | 5,4 | 201 | 6,6 | 177 | 5,9 | 179 | 5,9 | 180 | 5,9 |

Fig. 6

```
pS52                    TGAGCTGGTAGGATAACACTCCATT-CTTTTTTTTTTTTTTTTTTTTTT
D28917 (HCV-K3a/650)    .........................-.C......G.....CCC.......
AF009075 (WS)           .........................T........G...............
D17763 (NZL1)           ..........A..............T........G................
D85024 (n.a.)           ..........A.C............A.T..G.........C..........
D85025 (n.a.)           ..........A.C............A.T..G....................
```

Fig. 7

```
pED43            TAGGCAGCTTAACACTCCGACCTTAGGGTCCCCTTGTTTTTTTTTTTTTTTT
Y11604 (ED43)    ...................................T...............GG
AF009077 (43E)   ..................................................C...
D86533 (SD001)   ------............................TG.T.................
D86535 (SD003)   ------...........................A.CTG.................
D86536 (SD004)   ------..............................T.....G............
D86540 (SD016)   ------............................TG.T................--
D86541 (SD024)   ------............................T..T.GG..............
D86542 (SD033)   ------...........................T..GT.................
```

Fig. 8

SEQUENCE LISTING

```
<160> NUMBER OF SEQ ID NOS: 4

<210> SEQ ID NO 1
<211> LENGTH: 3021
<212> TYPE: PRT
<213> ORGANISM: Hepatitis C virus

<400> SEQUENCE: 1

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
                20                  25                  30

Gly Val Tyr Val Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95
```

-continued

```
Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
    210                 215                 220

Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
    290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Val Ala His
                325                 330                 335

Ile Leu Arg Leu Pro Gln Thr Leu Phe Asp Ile Leu Ala Gly Ala His
            340                 345                 350

Trp Gly Ile Leu Ala Gly Leu Ala Tyr Tyr Ser Met Gln Gly Asn Trp
        355                 360                 365

Ala Lys Val Ala Ile Val Met Ile Met Phe Ser Gly Val Asp Ala Glu
    370                 375                 380

Thr Tyr Val Thr Gly Gly Ser Val Ala His Ser Ala Arg Gly Leu Thr
385                 390                 395                 400

Ser Leu Phe Ser Met Gly Ala Lys Gln Lys Leu Gln Leu Val Asn Thr
                405                 410                 415

Asn Gly Ser Trp His Ile Asn Ser Thr Ala Leu Asn Cys Asn Glu Ser
            420                 425                 430

Ile Asn Thr Gly Phe Ile Ala Gly Leu Phe Tyr Tyr His Lys Phe Asn
        435                 440                 445

Ser Thr Gly Cys Pro Gln Arg Leu Ser Ser Cys Lys Pro Ile Ile Ser
    450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
            500                 505                 510

Ser Pro Val Val Val Gly Thr Thr Asp Ile Lys Gly Lys Pro Thr Tyr
```

```
                515                 520                 525
Asn Trp Gly Glu Asn Glu Thr Asp Val Phe Leu Leu Glu Ser Leu Arg
    530                 535                 540
Pro Pro Ser Gly Arg Trp Phe Gly Cys Ala Trp Met Asn Ser Thr Gly
545                 550                 555                 560
Phe Leu Lys Thr Cys Gly Ala Pro Pro Cys Asn Ile Tyr Gly Gly Glu
                565                 570                 575
Gly Asp Pro Glu Asn Glu Thr Asp Leu Phe Cys Pro Thr Asp Cys Phe
            580                 585                 590
Arg Lys His Pro Glu Ala Thr Tyr Ser Arg Cys Gly Ala Gly Pro Trp
                595                 600                 605
Leu Thr Pro Arg Cys Met Val Asp Tyr Pro Tyr Arg Leu Trp His Tyr
            610                 615                 620
Pro Cys Thr Val Asn Phe Thr Leu Phe Lys Val Arg Met Phe Val Gly
625                 630                 635                 640
Gly Phe Glu His Arg Phe Thr Ala Ala Cys Asn Trp Thr Arg Gly Glu
                645                 650                 655
Arg Cys Asn Ile Glu Asp Arg Asp Arg Ser Glu Gln His Pro Leu Leu
            660                 665                 670
His Ser Thr Thr Glu Leu Ala Ile Leu Pro Cys Ser Phe Thr Pro Met
        675                 680                 685
Pro Ala Leu Ser Thr Gly Leu Ile His Leu His Gln Asn Ile Val Asp
690                 695                 700
Val Gln Tyr Leu Tyr Gly Val Gly Ser Asp Met Val Gly Trp Ala Leu
705                 710                 715                 720
Lys Trp Glu Phe Val Ile Leu Val Phe Leu Leu Leu Ala Asp Ala Arg
                725                 730                 735
Val Cys Val Ala Leu Trp Leu Met Leu Met Val Ser Gln Ala Glu Ala
                740                 745                 750
Ala Leu Glu Asn Leu Val Thr Leu Asn Ala Val Ala Ala Ala Gly Thr
            755                 760                 765
His Gly Ile Gly Trp Tyr Leu Val Ala Phe Cys Ala Ala Trp Tyr Val
    770                 775                 780
Arg Gly Lys Leu Val Pro Leu Thr Ile Tyr Gly Leu Thr Gly Leu Trp
785                 790                 795                 800
Ser Leu Ala Leu Leu Val Leu Leu Pro Gln Arg Ala Tyr Ala Trp
                805                 810                 815
Ser Gly Glu Asp Ser Ala Thr Leu Gly Ala Gly Val Leu Ala Leu Phe
            820                 825                 830
Gly Phe Phe Thr Leu Ser Pro Trp Tyr Lys His Trp Ile Gly Arg Leu
            835                 840                 845
Met Trp Trp Asn Gln Tyr Thr Ile Cys Arg Cys Glu Ala Ala Leu Gln
    850                 855                 860
Val Trp Val Pro Pro Leu Leu Ala Arg Gly Ser Arg Asp Gly Val Ile
865                 870                 875                 880
Leu Leu Thr Ser Leu Leu Tyr Pro Ser Leu Ile Phe Asp Ile Thr Lys
                885                 890                 895
Leu Leu Ile Ala Val Ile Gly Pro Leu Tyr Leu Ile Gln Ala Ala Ile
            900                 905                 910
Thr Thr Thr Pro Tyr Phe Val Arg Ala His Val Leu Val Arg Leu Cys
            915                 920                 925
Met Leu Val Arg Ser Val Met Gly Gly Lys Tyr Phe Gln Met Ala Ile
        930                 935                 940
```

-continued

```
Leu Ser Ile Gly Arg Trp Phe Asn Thr Tyr Leu Tyr Asp His Leu Ala
945                 950                 955                 960

Pro Met Gln His Trp Ala Ala Ala Gly Leu Lys Asp Leu Ala Val Ala
                965                 970                 975

Thr Glu Pro Val Ile Phe Ser Pro Met Glu Ile Lys Val Ile Thr Trp
            980                 985                 990

Gly Ala Asp Thr Ala Ala Cys Gly Asp Ile Leu Cys Gly Leu Pro Val
        995                 1000                1005

Ser Ala Arg Leu Gly Arg Glu Val Leu Leu Gly Pro Ala Asp Asp
    1010                1015                1020

Tyr Arg Glu Met Gly Trp Arg Leu Leu Ala Pro Ile Thr Ala Tyr
    1025                1030                1035

Ala Gln Gln Thr Arg Gly Leu Leu Gly Thr Ile Val Thr Ser Leu
    1040                1045                1050

Thr Gly Arg Asp Lys Asn Ile Val Thr Gly Glu Val Gln Val Leu
    1055                1060                1065

Ser Thr Ala Thr Gln Thr Phe Leu Gly Thr Val Gly Gly Val
    1070                1075                1080

Met Trp Thr Val Tyr His Gly Ala Gly Ser Lys Thr Leu Ala Gly
    1085                1090                1095

Ala Lys His Pro Ala Leu Gln Met Tyr Thr Asn Val Asp Gln Asp
    1100                1105                1110

Leu Val Gly Trp Pro Ala Pro Pro Gly Ala Lys Ser Leu Glu Pro
    1115                1120                1125

Cys Ala Cys Gly Ser Ala Asp Leu Tyr Leu Val Thr Arg Asp Ala
    1130                1135                1140

Asp Val Ile Pro Ala Arg Arg Arg Gly Asp Ser Thr Ala Ser Leu
    1145                1150                1155

Leu Ser Pro Arg Pro Leu Ala Cys Leu Lys Gly Ser Ser Gly Gly
    1160                1165                1170

Pro Val Met Cys Pro Ser Gly His Val Ala Gly Ile Phe Arg Ala
    1175                1180                1185

Ala Val Cys Thr Arg Gly Val Ala Lys Ala Leu Gln Phe Val Pro
    1190                1195                1200

Val Glu Thr Leu Ser Thr Gln Ala Arg Ser Pro Ser Phe Ser Asp
    1205                1210                1215

Asn Ser Thr Pro Pro Ala Val Pro Gln Ser Tyr Gln Val Gly Tyr
    1220                1225                1230

Leu His Ala Pro Thr Gly Ser Gly Lys Ser Thr Lys Val Pro Ala
    1235                1240                1245

Ala Tyr Val Ala Gln Gly Tyr Asn Val Leu Val Leu Asn Pro Ser
    1250                1255                1260

Val Ala Ala Thr Leu Gly Phe Gly Ser Phe Met Ser Arg Ala Tyr
    1265                1270                1275

Gly Ile Asp Pro Asn Ile Arg Thr Gly Asn Arg Thr Val Thr Thr
    1280                1285                1290

Gly Ala Lys Leu Thr Tyr Ser Thr Tyr Gly Lys Phe Leu Ala Asp
    1295                1300                1305

Gly Gly Cys Ser Gly Gly Ala Tyr Asp Val Ile Ile Cys Asp Glu
    1310                1315                1320

Cys His Ala Gln Asp Ala Thr Ser Ile Leu Gly Ile Gly Thr Val
    1325                1330                1335
```

-continued

```
Leu Asp Gln Ala Glu Thr Ala Gly Val Arg Leu Thr Val Leu Ala
    1340                1345                1350
Thr Ala Thr Pro Pro Gly Ser Ile Thr Val Pro His Ser Asn Ile
    1355                1360                1365
Glu Glu Val Ala Leu Gly Ser Glu Gly Glu Ile Pro Phe Tyr Gly
    1370                1375                1380
Lys Ala Ile Pro Ile Ala Leu Leu Lys Gly Gly Arg His Leu Ile
    1385                1390                1395
Phe Cys His Ser Lys Lys Cys Asp Glu Val Ala Ala Lys Leu
    1400                1405                1410
Arg Gly Met Gly Leu Asn Ala Val Ala Tyr Tyr Arg Gly Leu Asp
    1415                1420                1425
Val Ser Val Ile Pro Thr Thr Gly Asp Val Val Cys Ala Thr
    1430                1435                1440
Asp Ala Leu Met Thr Gly Phe Thr Gly Asp Phe Asp Ser Val Ile
    1445                1450                1455
Asp Cys Asn Val Ala Val Glu Gln Tyr Val Asp Phe Ser Leu Asp
    1460                1465                1470
Pro Thr Phe Ser Ile Glu Thr Arg Thr Ala Pro Gln Asp Ala Val
    1475                1480                1485
Ser Arg Ser Gln Arg Arg Gly Arg Thr Gly Arg Gly Arg Leu Gly
    1490                1495                1500
Thr Tyr Arg Tyr Val Ala Pro Gly Glu Arg Pro Ser Gly Met Phe
    1505                1510                1515
Asp Ser Val Val Leu Cys Glu Cys Tyr Asp Ala Gly Cys Ser Trp
    1520                1525                1530
Tyr Asp Leu Gln Pro Ala Glu Thr Thr Val Arg Leu Arg Ala Tyr
    1535                1540                1545
Leu Asn Thr Pro Gly Leu Pro Val Cys Gln Asp His Leu Asp Phe
    1550                1555                1560
Trp Glu Ser Val Phe Thr Gly Leu Thr His Ile Asp Ala His Phe
    1565                1570                1575
Leu Ser Gln Thr Lys Gln Gln Gly Leu Asn Phe Ser Phe Leu Thr
    1580                1585                1590
Ala Tyr Gln Ala Thr Val Cys Ala Arg Ala Gln Ala Ser Pro Pro
    1595                1600                1605
Ser Trp Asp Glu Thr Trp Lys Cys Leu Val Arg Leu Lys Pro Thr
    1610                1615                1620
Leu His Gly Pro Thr Pro Leu Leu Tyr Arg Leu Gly Pro Val Gln
    1625                1630                1635
Asn Asp Ile Cys Leu Thr His Pro Val Thr Lys Tyr Ile Met Ala
    1640                1645                1650
Cys Met Ser Ala Asp Leu Glu Val Thr Thr Ser Thr Trp Val Leu
    1655                1660                1665
Leu Gly Gly Val Leu Ala Ala Leu Ala Ala Tyr Cys Leu Ser Val
    1670                1675                1680
Gly Cys Val Val Ile Val Gly His Ile Glu Leu Arg Gly Lys Pro
    1685                1690                1695
Ala Leu Val Pro Asp Arg Glu Val Leu Tyr Gln Gln Tyr Asp Glu
    1700                1705                1710
Met Glu Glu Cys Ser Gln Ala Ala Pro Tyr Ile Glu Gln Ala Gln
    1715                1720                1725
Ala Ile Ala His Gln Phe Lys Glu Lys Ile Leu Gly Leu Leu Gln
```

-continued

```
            1730                1735                1740

Arg Ala Thr Gln Gln Ala Val Ile Glu Pro Ile Val Ala Thr
        1745                1750                1755

Asn Trp Gln Lys Leu Glu Thr Phe Trp His Lys His Met Trp Asn
    1760                1765                1770

Phe Val Ser Gly Ile Gln Tyr Leu Ala Gly Leu Ser Thr Leu Pro
    1775                1780                1785

Gly Asn Pro Ala Val Ala Ser Leu Met Ala Phe Thr Ala Ser Val
    1790                1795                1800

Thr Ser Pro Leu Thr Thr Asn Gln Thr Met Phe Phe Asn Ile Leu
    1805                1810                1815

Gly Gly Trp Val Ala Thr His Leu Ala Gly Pro Gln Ser Ser Ser
    1820                1825                1830

Ala Phe Val Val Ser Gly Leu Ala Gly Ala Ala Ile Gly Gly Ile
    1835                1840                1845

Gly Leu Gly Arg Val Leu Leu Asp Ile Leu Ala Gly Tyr Gly Ala
    1850                1855                1860

Gly Val Ser Gly Ala Leu Val Ala Phe Lys Ile Met Gly Gly Glu
    1865                1870                1875

Leu Pro Thr Thr Glu Asp Met Val Asn Leu Leu Pro Ala Ile Leu
    1880                1885                1890

Ser Pro Gly Ala Leu Val Val Gly Val Ile Cys Ala Ala Ile Leu
    1895                1900                1905

Arg Arg His Val Gly Pro Gly Glu Gly Ala Val Gln Trp Met Asn
    1910                1915                1920

Arg Leu Ile Ala Phe Ala Ser Arg Gly Asn His Val Ser Pro Thr
    1925                1930                1935

His Tyr Val Pro Glu Ser Asp Ala Ala Ala Arg Val Thr Ala Leu
    1940                1945                1950

Leu Ser Ser Leu Thr Val Thr Ser Leu Leu Arg Arg Leu His Lys
    1955                1960                1965

Trp Ile Asn Glu Asp Tyr Pro Ser Pro Cys Ser Gly Asp Trp Leu
    1970                1975                1980

Arg Asp Ile Trp Asp Trp Val Cys Ser Val Leu Ser Asp Phe Lys
    1985                1990                1995

Thr Trp Leu Ser Ala Lys Ile Met Pro Ala Leu Pro Gly Leu Pro
    2000                2005                2010

Phe Ile Ser Cys Gln Lys Gly Tyr Lys Gly Val Trp Arg Gly Asp
    2015                2020                2025

Gly Val Met Ser Thr Arg Cys Pro Cys Gly Ala Ser Ile Thr Gly
    2030                2035                2040

His Val Lys Asn Gly Ser Met Arg Leu Ala Gly Pro Arg Met Cys
    2045                2050                2055

Ala Asn Met Trp His Gly Thr Phe Pro Ile Asn Glu Tyr Thr Thr
    2060                2065                2070

Gly Pro Ser Thr Pro Cys Pro Ser Pro Asn Tyr Thr Arg Ala Leu
    2075                2080                2085

Trp Arg Val Ala Ala Ser Ser Tyr Val Glu Val Arg Arg Val Gly
    2090                2095                2100

Asp Phe His Tyr Ile Thr Gly Ala Thr Glu Asp Glu Leu Lys Cys
    2105                2110                2115

Pro Cys Gln Val Pro Ala Ala Glu Phe Phe Thr Glu Val Asp Gly
    2120                2125                2130
```

```
Val  Arg  Leu  His  Arg  Tyr  Ala  Pro  Pro  Cys  Lys  Pro  Leu  Leu  Arg
     2135           2140                     2145

Glu  Glu  Ile  Thr  Phe  Ser  Val  Gly  Leu  His  Ser  Tyr  Ala  Ile  Gly
2150                2155                          2160

Ser  Gln  Leu  Pro  Cys  Glu  Pro  Glu  Pro  Asp  Val  Ser  Val  Leu  Thr
2165                     2170                     2175

Ser  Met  Leu  Arg  Asp  Pro  Ser  His  Ile  Thr  Ala  Glu  Thr  Ala  Ala
2180                     2185                     2190

Arg  Arg  Leu  Ala  Arg  Gly  Ser  Pro  Pro  Ser  Glu  Ala  Ser  Ser  Ser
2195                     2200                     2205

Ala  Ser  Gln  Leu  Ser  Ala  Pro  Ser  Leu  Lys  Ala  Thr  Cys  Gln  Thr
2210                     2215                     2220

His  Arg  Pro  His  Pro  Asp  Ala  Glu  Leu  Val  Asp  Ala  Asn  Leu  Leu
2225                     2230                     2235

Trp  Arg  Gln  Glu  Met  Gly  Ser  Asn  Ile  Thr  Arg  Val  Glu  Ser  Glu
2240                     2245                     2250

Thr  Lys  Val  Val  Ile  Leu  Asp  Ser  Phe  Glu  Pro  Leu  Arg  Ala  Glu
2255                     2260                     2265

Ala  Asp  Asp  Ala  Glu  Leu  Ser  Val  Ala  Ala  Glu  Cys  Phe  Lys  Lys
2270                     2275                     2280

Pro  Pro  Lys  Tyr  Pro  Pro  Ala  Leu  Pro  Ile  Trp  Ala  Arg  Pro  Asp
2285                     2290                     2295

Tyr  Asn  Pro  Pro  Leu  Leu  Asp  Arg  Trp  Lys  Ala  Pro  Asp  Tyr  Val
2300                     2305                     2310

Pro  Pro  Thr  Val  His  Gly  Cys  Ala  Leu  Pro  Pro  Arg  Gly  Ala  Pro
2315                     2320                     2325

Pro  Val  Pro  Pro  Pro  Arg  Arg  Lys  Arg  Thr  Ile  Gln  Leu  Asp  Gly
2330                     2335                     2340

Ser  Asn  Val  Ser  Ala  Ala  Leu  Ala  Ala  Leu  Ala  Glu  Lys  Ser  Phe
2345                     2350                     2355

Pro  Thr  Pro  Lys  Ser  Gln  Glu  Glu  Asn  Ser  Ser  Ser  Ser  Gly  Val
2360                     2365                     2370

Asp  Thr  Gln  Ser  Ser  Thr  Thr  Ser  Arg  Met  Pro  Pro  Ser  Pro  Gly
2375                     2380                     2385

Gly  Glu  Ser  Asp  Ser  Glu  Ser  Cys  Ser  Ser  Met  Pro  Pro  Leu  Glu
2390                     2395                     2400

Gly  Glu  Pro  Gly  Asp  Pro  Asp  Leu  Ser  Cys  Asp  Ser  Trp  Ser  Thr
2405                     2410                     2415

Val  Ser  Asp  Asn  Glu  Glu  Gln  Ser  Val  Val  Cys  Cys  Ser  Met  Ser
2420                     2425                     2430

Tyr  Ser  Trp  Thr  Gly  Ala  Leu  Ile  Thr  Pro  Cys  Ser  Ala  Glu  Glu
2435                     2440                     2445

Glu  Lys  Leu  Pro  Ile  Ser  Pro  Leu  Ser  Asn  Ser  Leu  Leu  Arg  His
2450                     2455                     2460

His  Asn  Leu  Val  Tyr  Ser  Thr  Ser  Ser  Arg  Ser  Ala  Ser  Gln  Arg
2465                     2470                     2475

Gln  Arg  Lys  Val  Thr  Phe  Asp  Arg  Leu  Gln  Val  Leu  Asp  Asp  His
2480                     2485                     2490

Tyr  Lys  Thr  Ala  Leu  Lys  Glu  Val  Lys  Glu  Arg  Ala  Ser  Arg  Val
2495                     2500                     2505

Lys  Ala  Arg  Met  Leu  Thr  Ile  Glu  Glu  Ala  Cys  Ala  Leu  Val  Pro
2510                     2515                     2520
```

```
Pro His Ser Ala Arg Ser Lys Phe Gly Tyr Ser Ala Lys Asp Val
2525                2530                2535

Arg Ser Leu Ser Ser Arg Ala Ile Asp Gln Ile Arg Ser Val Trp
2540                2545                2550

Glu Asp Leu Leu Glu Asp Thr Thr Thr Pro Ile Pro Thr Thr Ile
2555                2560                2565

Met Ala Lys Asn Glu Val Phe Cys Val Asp Pro Ala Lys Gly Gly
2570                2575                2580

Arg Lys Pro Ala Arg Leu Ile Val Tyr Pro Asp Leu Gly Val Arg
2585                2590                2595

Val Cys Glu Lys Arg Ala Leu Tyr Asp Val Ile Gln Lys Leu Ser
2600                2605                2610

Ile Glu Thr Met Gly Ser Ala Tyr Gly Phe Gln Tyr Ser Pro Gln
2615                2620                2625

Gln Arg Val Glu Arg Leu Leu Lys Met Trp Thr Ser Lys Lys Thr
2630                2635                2640

Pro Leu Gly Phe Ser Tyr Asp Thr Arg Cys Phe Asp Ser Thr Val
2645                2650                2655

Thr Glu Gln Asp Ile Arg Val Glu Glu Glu Ile Tyr Gln Cys Cys
2660                2665                2670

Asn Leu Glu Pro Glu Ala Arg Lys Val Ile Ser Ser Leu Thr Glu
2675                2680                2685

Arg Leu Tyr Cys Gly Gly Pro Met Phe Asn Ser Lys Gly Ala Gln
2690                2695                2700

Cys Gly Tyr Arg Arg Cys Arg Ala Ser Gly Val Leu Pro Thr Ser
2705                2710                2715

Phe Gly Asn Thr Ile Thr Cys Tyr Ile Lys Ala Thr Ala Ala Ala
2720                2725                2730

Lys Ala Ala Gly Leu Arg Asn Pro Asp Phe Leu Val Cys Gly Asp
2735                2740                2745

Asp Leu Val Val Val Ala Glu Ser Asp Gly Val Asp Glu Asp Arg
2750                2755                2760

Ala Ala Leu Arg Ala Phe Thr Glu Ala Met Thr Arg Tyr Ser Ala
2765                2770                2775

Pro Pro Gly Asp Ala Pro Gln Pro Thr Tyr Asp Leu Glu Leu Ile
2780                2785                2790

Thr Ser Cys Ser Ser Asn Val Ser Val Ala Arg Asp Asp Lys Gly
2795                2800                2805

Arg Arg Tyr Tyr Tyr Leu Thr Arg Asp Ala Thr Thr Pro Leu Ala
2810                2815                2820

Arg Ala Ala Trp Glu Thr Ala Arg His Thr Pro Val Asn Ser Trp
2825                2830                2835

Leu Gly Asn Ile Ile Met Tyr Ala Pro Thr Ile Trp Val Arg Met
2840                2845                2850

Val Met Met Thr His Phe Phe Ser Ile Leu Gln Ser Gln Glu Ile
2855                2860                2865

Leu Asp Arg Pro Leu Asp Phe Glu Met Tyr Gly Ala Thr Tyr Ser
2870                2875                2880

Val Thr Pro Leu Asp Leu Pro Ala Ile Ile Glu Arg Leu His Gly
2885                2890                2895

Leu Ser Ala Phe Thr Leu His Ser Tyr Ser Pro Val Glu Leu Asn
2900                2905                2910

Arg Val Ala Gly Thr Leu Arg Lys Leu Gly Cys Pro Pro Leu Arg
```

```
                    2915                  2920                  2925
Ala Trp Arg His Arg Ala Arg Ala Val Arg Ala Lys Leu Ile Ala
    2930                  2935                  2940

Gln Gly Gly Lys Ala Lys Ile Cys Gly Leu Tyr Leu Phe Asn Trp
    2945                  2950                  2955

Ala Val Arg Thr Lys Thr Asn Leu Thr Pro Leu Pro Ala Thr Gly
    2960                  2965                  2970

Gln Leu Asp Leu Ser Ser Trp Phe Thr Val Gly Val Gly Gly Asn
    2975                  2980                  2985

Asp Ile Tyr His Ser Val Ser Arg Ala Arg Thr Arg His Leu Leu
    2990                  2995                  3000

Leu Cys Leu Leu Leu Leu Thr Val Gly Val Gly Ile Phe Leu Leu
    3005                  3010                  3015

Pro Ala Arg
    3020

<210> SEQ ID NO 2
<211> LENGTH: 3008
<212> TYPE: PRT
<213> ORGANISM: Hepatitis C virus

<400> SEQUENCE: 2

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Asn Tyr Arg Asn Val Ser Gly Ile Tyr His Val Thr Asn Asp Cys Pro
        195                 200                 205

Asn Ser Ser Ile Val Tyr Glu Ala Asp His His Ile Leu His Leu Pro
    210                 215                 220

Gly Cys Val Pro Cys Val Arg Glu Gly Asn Gln Ser Arg Cys Trp Val
225                 230                 235                 240

Ala Leu Thr Pro Thr Val Ala Pro Tyr Ile Gly Ala Pro Leu Glu
                245                 250                 255
```

```
Ser Leu Arg Ser His Val Asp Leu Met Val Gly Ala Ala Thr Val Cys
            260                 265                 270

Ser Gly Leu Tyr Ile Gly Asp Leu Cys Gly Gly Leu Phe Leu Val Gly
        275                 280                 285

Gln Met Phe Ser Phe Arg Pro Arg His Trp Thr Thr Gln Asp Cys
290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Leu Val Leu Ala Gln
                325                 330                 335

Val Met Arg Ile Pro Thr Thr Leu Val Asp Leu Leu Ser Gly Gly His
            340                 345                 350

Trp Gly Val Leu Val Gly Val Ala Tyr Phe Ser Met Gln Ala Asn Trp
        355                 360                 365

Ala Lys Val Ile Leu Val Leu Phe Leu Phe Ala Gly Val Asp Ala Glu
    370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
                435                 440                 445

Ser Ser Gly Cys Ser Glu Arg Leu Ala Cys Cys Lys Ser Leu Asp Ser
450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
            500                 505                 510

Ser Pro Val Val Gly Thr Thr Asp His Val Gly Val Pro Thr Tyr
        515                 520                 525

Thr Trp Gly Glu Asn Glu Thr Asp Val Phe Leu Leu Asn Ser Thr Arg
530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
            580                 585                 590

Thr Tyr Ala Lys Cys Gly Ser Gly Pro Trp Ile Thr Pro Arg Cys Leu
        595                 600                 605

Ile Asp Tyr Pro Tyr Arg Leu Trp His Phe Pro Cys Thr Ala Asn Phe
    610                 615                 620

Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
                645                 650                 655

Arg Asp Arg Val Glu Leu Ser Pro Leu Leu Leu Thr Thr Thr Ala Trp
            660                 665                 670

Gln Ile Leu Pro Cys Ser Phe Thr Thr Leu Pro Ala Leu Ser Thr Gly
```

```
                675                 680                 685
Leu Ile His Leu His Gln Asn Ile Val Asp Val Gln Tyr Leu Tyr Gly
            690                 695                 700
Val Gly Ser Ala Val Val Ser Trp Ala Leu Lys Trp Glu Tyr Val Val
705                 710                 715                 720
Leu Ala Phe Leu Leu Leu Ala Asp Ala Arg Val Ser Ala Cys Leu Trp
                725                 730                 735
Met Met Phe Met Val Ser Gln Val Glu Ala Ala Leu Ser Asn Leu Ile
            740                 745                 750
Asn Ile Asn Ala Ala Ser Ala Ala Gly Ala Gln Gly Phe Trp Tyr Ala
            755                 760                 765
Ile Leu Phe Ile Cys Ile Val Trp His Val Lys Gly Arg Phe Pro Ala
            770                 775                 780
Ala Ala Ala Tyr Ala Ala Cys Gly Leu Trp Pro Leu Phe Leu Leu Leu
785                 790                 795                 800
Leu Met Leu Pro Glu Arg Ala Tyr Ala Tyr Asp Gln Glu Val Ala Gly
                805                 810                 815
Ser Leu Gly Gly Ala Ile Val Val Met Leu Thr Ile Leu Thr Leu Ser
            820                 825                 830
Pro His Tyr Lys Leu Trp Leu Ala Arg Gly Leu Trp Trp Ile Gln Tyr
            835                 840                 845
Phe Ile Ala Arg Thr Glu Ala Val Leu His Val Tyr Ile Pro Ser Phe
850                 855                 860
Asn Val Arg Gly Pro Arg Asp Ser Val Ile Val Leu Ala Val Leu Val
865                 870                 875                 880
Cys Pro His Leu Val Phe Asp Ile Thr Lys Tyr Leu Leu Ala Ile Leu
                885                 890                 895
Gly Pro Leu His Ile Leu Gln Ala Ser Leu Leu Arg Ile Pro Tyr Phe
            900                 905                 910
Val Arg Ala Gln Ala Leu Val Lys Ile Cys Ser Leu Leu Arg Gly Val
            915                 920                 925
Val Tyr Gly Lys Tyr Phe Gln Met Val Val Leu Lys Ala Gly Ala Leu
            930                 935                 940
Thr Gly Thr Tyr Ile Tyr Asp His Leu Thr Pro Met Ser Asp Trp Ala
945                 950                 955                 960
Ala Thr Gly Leu Arg Asp Leu Ala Val Ala Leu Glu Pro Val Val Phe
                965                 970                 975
Thr Pro Met Glu Lys Lys Val Ile Val Trp Gly Ala Asp Thr Ala Ala
                980                 985                 990
Cys Gly Asp Ile Ile Arg Gly Leu Pro Val Ser Ala Arg Leu Gly Asn
            995                 1000                1005
Glu Ile Leu Leu Gly Pro Ala Asp Thr Glu Thr Ser Lys Gly Trp
            1010                1015                1020
Arg Leu Leu Ala Pro Ile Thr Ala Tyr Ala Gln Gln Thr Arg Gly
            1025                1030                1035
Leu Phe Ser Thr Ile Val Thr Ser Leu Thr Gly Arg Asp Thr Asn
            1040                1045                1050
Glu Asn Cys Gly Glu Val Gln Val Leu Ser Thr Ala Thr Gln Ser
            1055                1060                1065
Phe Leu Gly Thr Ala Val Asn Gly Val Met Trp Thr Val Tyr His
            1070                1075                1080
Gly Ala Gly Ala Lys Thr Ile Ser Gly Pro Lys Gly Pro Val Asn
            1085                1090                1095
```

```
Gln Met Tyr Thr Asn Val Asp Gln Asp Leu Val Gly Trp Pro Ala
    1100            1105            1110

Pro Pro Gly Val Arg Ser Leu Ala Pro Cys Thr Cys Gly Ser Ala
    1115            1120            1125

Asp Leu Tyr Leu Val Thr Arg His Ala Asp Val Ile Pro Val Arg
    1130            1135            1140

Arg Arg Gly Asp Thr Arg Gly Ala Leu Leu Ser Pro Arg Pro Ile
    1145            1150            1155

Ser Thr Leu Lys Gly Ser Ser Gly Gly Pro Leu Leu Cys Pro Met
    1160            1165            1170

Gly His Ala Ala Gly Ile Phe Arg Ala Ala Val Cys Thr Arg Gly
    1175            1180            1185

Val Ala Lys Ala Val Asp Phe Val Pro Val Glu Ser Leu Glu Thr
    1190            1195            1200

Thr Met Arg Ser Pro Val Phe Thr Asp Asn Ser Thr Pro Pro Ala
    1205            1210            1215

Val Pro Gln Thr Tyr Gln Val Ala His Leu His Ala Pro Thr Gly
    1220            1225            1230

Ser Gly Lys Ser Thr Lys Val Pro Ala Ala Tyr Ala Ala Gln Gly
    1235            1240            1245

Tyr Lys Val Leu Val Leu Asn Pro Ser Val Ala Ala Thr Leu Gly
    1250            1255            1260

Phe Gly Val Tyr Met Ser Lys Ala Tyr Gly Ile Asp Pro Asn Ile
    1265            1270            1275

Arg Ser Gly Val Arg Thr Ile Thr Thr Gly Ala Pro Ile Thr Tyr
    1280            1285            1290

Ser Thr Tyr Gly Lys Phe Leu Ala Asp Gly Gly Cys Ser Gly Gly
    1295            1300            1305

Ala Tyr Asp Ile Ile Ile Cys Asp Glu Cys His Ser Thr Asp Ser
    1310            1315            1320

Thr Thr Ile Leu Gly Ile Gly Thr Val Leu Asp Gln Ala Glu Thr
    1325            1330            1335

Ala Gly Val Arg Leu Thr Val Leu Ala Thr Ala Thr Pro Pro Gly
    1340            1345            1350

Ser Val Thr Thr Pro His Ser Asn Ile Glu Glu Val Ala Leu Pro
    1355            1360            1365

Thr Thr Gly Glu Ile Pro Phe Tyr Gly Lys Ala Ile Pro Leu Glu
    1370            1375            1380

Leu Ile Lys Gly Gly Arg His Leu Ile Phe Cys His Ser Lys Lys
    1385            1390            1395

Lys Cys Asp Glu Leu Ala Arg Gln Leu Thr Ser Leu Gly Leu Asn
    1400            1405            1410

Ala Val Ala Tyr Tyr Arg Gly Leu Asp Val Ser Val Ile Pro Thr
    1415            1420            1425

Ser Gly Asp Val Val Val Cys Ala Thr Asp Ala Leu Met Thr Gly
    1430            1435            1440

Phe Thr Gly Asp Phe Asp Ser Val Ile Asp Cys Asn Thr Ser Val
    1445            1450            1455

Ile Gln Thr Val Asp Phe Ser Leu Asp Pro Thr Phe Ser Ile Glu
    1460            1465            1470

Thr Thr Thr Val Pro Gln Asp Ala Val Ser Arg Ser Gln Arg Arg
    1475            1480            1485
```

-continued

```
Gly Arg Thr Gly Arg Gly Arg Leu Gly Thr Tyr Arg Tyr Val Thr
1490                1495                1500

Pro Gly Glu Arg Pro Ser Gly Met Phe Asp Thr Ala Val Leu Cys
1505                1510                1515

Glu Cys Tyr Asp Ala Gly Cys Ala Trp Tyr Glu Leu Thr Pro Ala
1520                1525                1530

Glu Thr Thr Thr Arg Leu Lys Ala Tyr Phe Asp Thr Pro Gly Leu
1535                1540                1545

Pro Val Cys Gln Asp His Leu Glu Phe Trp Glu Ser Val Phe Thr
1550                1555                1560

Gly Leu Thr His Ile Asp Gly His Phe Leu Ser Gln Thr Lys Gln
1565                1570                1575

Ser Gly Glu Asn Phe Pro Tyr Leu Val Ala Tyr Gln Ala Thr Val
1580                1585                1590

Cys Ala Lys Ala Leu Ala Pro Pro Ser Trp Asp Thr Met Trp
1595                1600                1605

Lys Cys Leu Ile Arg Leu Lys Pro Thr Leu His Gly Pro Thr Pro
1610                1615                1620

Leu Leu Tyr Arg Leu Gly Ser Val Gln Asn Glu Val Val Leu Thr
1625                1630                1635

His Pro Ile Thr Lys Tyr Ile Met Ala Cys Met Ser Ala Asp Leu
1640                1645                1650

Glu Val Val Thr Ser Thr Trp Val Leu Val Gly Gly Val Leu Ala
1655                1660                1665

Ala Leu Ala Ala Tyr Cys Leu Ser Val Gly Ser Val Val Ile Val
1670                1675                1680

Gly Arg Val Val Leu Ser Gly Gln Pro Ala Val Ile Pro Asp Arg
1685                1690                1695

Glu Val Leu Tyr Gln Gln Phe Asp Glu Met Glu Glu Cys Ser Lys
1700                1705                1710

His Leu Pro Leu Val Glu His Gly Leu Gln Leu Ala Glu Gln Phe
1715                1720                1725

Lys Gln Lys Ala Leu Gly Leu Leu Asn Phe Ala Gly Lys Gln Ala
1730                1735                1740

Gln Glu Ala Thr Pro Val Ile Gln Ser Asn Phe Ala Lys Leu Glu
1745                1750                1755

Gln Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ser Phe Thr Ala Ala Val Thr Ser Pro Leu Thr Thr
1790                1795                1800

Gln Gln Thr Leu Leu Phe Asn Ile Leu Gly Gly Trp Val Ala Ser
1805                1810                1815

Gln Ile Ala Thr Pro Thr Ala Ser Thr Ala Phe Val Val Ser Gly
1820                1825                1830

Leu Ala Gly Ala Ala Val Gly Ser Val Gly Leu Gly Lys Ile Leu
1835                1840                1845

Val Asp Ile Leu Ala Gly Tyr Gly Ala Gly Val Ala Gly Ala Val
1850                1855                1860

Val Thr Phe Lys Ile Met Ser Gly Glu Met Pro Ser Thr Glu Asp
1865                1870                1875

Leu Val Asn Leu Leu Pro Ala Ile Leu Ser Pro Gly Ala Leu Val
```

-continued

```
            1880                1885                1890
Val Gly Val Val Cys Ala Ala Ile Leu Arg Arg His Val Gly Pro
            1895                1900                1905
Gly Glu Gly Ala Val Gln Trp Met Asn Arg Leu Ile Ala Phe Ala
            1910                1915                1920
Ser Arg Gly Asn His Val Ser Pro Thr His Tyr Val Pro Glu Ser
            1925                1930                1935
Asp Ala Ala Ala Arg Val Thr Thr Ile Leu Ser Ser Leu Thr Val
            1940                1945                1950
Thr Ser Leu Leu Arg Arg Leu His Lys Trp Ile Asn Glu Asp Cys
            1955                1960                1965
Ser Thr Pro Cys Ala Glu Ser Trp Leu Trp Glu Val Trp Asp Trp
            1970                1975                1980
Val Cys Thr Val Leu Ser Asp Phe Lys Thr Trp Leu Lys Ala Lys
            1985                1990                1995
Leu Leu Pro Leu Met Pro Gly Ile Pro Phe Leu Ser Cys Gln Arg
            2000                2005                2010
Gly Tyr Lys Gly Glu Trp Arg Gly Asp Gly Val Met His Thr Thr
            2015                2020                2025
Cys Pro Cys Gly Ala Asp Leu Ala Gly His Ile Lys Asn Gly Ser
            2030                2035                2040
Met Arg Ile Thr Gly Pro Lys Thr Cys Ser Asn Thr Trp His Gly
            2045                2050                2055
Thr Phe Pro Ile Asn Ala Tyr Thr Thr Gly Pro Gly Val Pro Ile
            2060                2065                2070
Pro Ala Pro Asn Tyr Lys Phe Ala Leu Trp Arg Val Ser Ala Glu
            2075                2080                2085
Asp Tyr Val Glu Val Arg Arg Val Gly Asp Phe His Tyr Val Thr
            2090                2095                2100
Gly Val Thr Gln Asp Asn Ile Lys Cys Pro Cys Gln Val Pro Ala
            2105                2110                2115
Pro Glu Phe Phe Thr Glu Val Asp Gly Ile Arg Leu His Arg His
            2120                2125                2130
Ala Pro Lys Cys Lys Pro Leu Leu Arg Asp Glu Val Ser Phe Ser
            2135                2140                2145
Val Gly Leu Asn Ser Phe Val Val Gly Ser Gln Leu Pro Cys Glu
            2150                2155                2160
Pro Glu Pro Asp Val Ala Val Leu Thr Ser Met Leu Thr Asp Pro
            2165                2170                2175
Ser His Ile Thr Ala Glu Ser Ala Arg Arg Leu Ala Arg Gly
            2180                2185                2190
Ser Arg Pro Ser Leu Ala Ser Ser Ser Ala Ser Gln Leu Ser Ala
            2195                2200                2205
Pro Ser Leu Lys Ala Thr Cys Thr Ala Pro His Asp Ser Pro Gly
            2210                2215                2220
Thr Asp Leu Leu Glu Ala Asn Leu Leu Trp Gly Ser Thr Ala Thr
            2225                2230                2235
Arg Val Glu Thr Asp Glu Lys Val Ile Ile Leu Asp Ser Phe Glu
            2240                2245                2250
Ser Cys Val Ala Glu Pro Asn Asp Asp Arg Glu Val Ser Val Ala
            2255                2260                2265
Ala Glu Ile Leu Arg Pro Thr Lys Lys Phe Pro Pro Ala Leu Pro
            2270                2275                2280
```

-continued

Ile Trp Ala Arg Pro Asp Tyr Asn Pro Pro Leu Thr Glu Thr Trp
2285             2290                 2295

Lys Gln Gln Asp Tyr Lys Pro Pro Thr Val His Gly Cys Ala Leu
2300             2305                 2310

Pro Pro Gly Lys Gln Pro Val Pro Pro Arg Arg Lys Arg
2315             2320                 2325

Thr Val Gln Leu Thr Glu Ser Val Val Ser Thr Ala Leu Ala Glu
2330             2335                 2340

Leu Ala Ala Lys Thr Phe Gly Gln Ser Glu Pro Ser Ser Asp Arg
2345             2350                 2355

Asp Thr Asp Leu Thr Thr Pro Thr Glu Thr Asp Ser Gly Pro
2360             2365                 2370

Ile Val Val Asp Asp Ala Ser Asp Asp Gly Ser Tyr Ser Ser Met
2375             2380                 2385

Pro Pro Leu Glu Gly Glu Pro Gly Asp Pro Asp Leu Thr Ser Asp
2390             2395                 2400

Ser Trp Ser Thr Val Ser Gly Ser Glu Asp Val Cys Cys Ser
2405             2410                 2415

Met Ser Tyr Ser Trp Thr Gly Ala Leu Val Thr Pro Cys Ala Ala
2420             2425                 2430

Glu Glu Ser Lys Leu Pro Ile Ser Pro Leu Ser Asn Ser Leu Leu
2435             2440                 2445

Arg His His Asn Met Val Tyr Ala Thr Thr Thr Arg Ser Ala Val
2450             2455                 2460

Thr Arg Gln Lys Lys Val Thr Phe Asp Arg Leu Gln Val Val Asp
2465             2470                 2475

Ser His Tyr Asn Glu Val Leu Lys Glu Ile Lys Ala Arg Ala Ser
2480             2485                 2490

Arg Val Lys Ala Arg Leu Leu Thr Thr Glu Glu Ala Cys Asp Leu
2495             2500                 2505

Thr Pro Pro His Ser Ala Arg Ser Lys Phe Gly Tyr Gly Ala Lys
2510             2515                 2520

Asp Val Arg Ser His Ser Arg Lys Ala Ile Asn His Ile Ser Ser
2525             2530                 2535

Val Trp Lys Asp Leu Leu Asp Asp Asn Asn Thr Pro Ile Pro Thr
2540             2545                 2550

Thr Ile Met Ala Lys Asn Glu Val Phe Ala Val Asn Pro Ala Lys
2555             2560                 2565

Gly Gly Arg Lys Pro Ala Arg Leu Ile Val Tyr Pro Asp Leu Gly
2570             2575                 2580

Val Arg Val Cys Glu Lys Arg Ala Leu His Asp Val Ile Lys Lys
2585             2590                 2595

Leu Pro Glu Ala Val Met Gly Ala Ala Tyr Gly Phe Gln Tyr Ser
2600             2605                 2610

Pro Ala Gln Arg Val Glu Phe Leu Leu Thr Ala Trp Lys Ser Lys
2615             2620                 2625

Lys Thr Pro Met Gly Phe Ser Tyr Asp Thr Arg Cys Phe Asp Ser
2630             2635                 2640

Thr Val Thr Glu Lys Asp Ile Arg Val Glu Glu Glu Val Tyr Gln
2645             2650                 2655

Cys Cys Asp Leu Glu Pro Glu Ala Arg Lys Val Ile Thr Ala Leu
2660             2665                 2670

```
Thr Asp Arg Leu Tyr Val Gly Gly Pro Met His Asn Ser Lys Gly
2675                 2680                2685

Asp Leu Cys Gly Tyr Arg Arg Cys Arg Ala Ser Gly Val Tyr Thr
2690                 2695                2700

Thr Ser Phe Gly Asn Thr Leu Thr Cys Tyr Leu Lys Ala Thr Ala
2705                 2710                2715

Ala Ile Arg Ala Ala Gly Leu Arg Asp Cys Thr Met Leu Val Cys
2720                 2725                2730

Gly Asp Asp Leu Val Val Ile Ala Glu Ser Asp Gly Val Glu Glu
2735                 2740                2745

Asp Asn Arg Ala Leu Arg Ala Phe Thr Glu Ala Met Thr Arg Tyr
2750                 2755                2760

Ser Ala Pro Pro Gly Asp Ala Pro Gln Pro Ala Tyr Asp Leu Glu
2765                 2770                2775

Leu Ile Thr Ser Cys Ser Ser Asn Val Ser Val Ala His Asp Val
2780                 2785                2790

Thr Gly Lys Lys Val Tyr Tyr Leu Thr Arg Asp Pro Glu Thr Pro
2795                 2800                2805

Leu Ala Arg Ala Ala Trp Glu Thr Val Arg His Thr Pro Val Asn
2810                 2815                2820

Ser Trp Leu Gly Asn Ile Ile Val Tyr Ala Pro Thr Ile Trp Val
2825                 2830                2835

Arg Met Ile Leu Met Thr His Phe Phe Ser Ile Leu Gln Ser Gln
2840                 2845                2850

Glu Ala Leu Glu Lys Ala Leu Asp Phe Asp Met Tyr Gly Val Thr
2855                 2860                2865

Tyr Ser Ile Thr Pro Leu Asp Leu Pro Ala Ile Ile Gln Arg Leu
2870                 2875                2880

His Gly Leu Ser Ala Phe Thr Leu His Gly Tyr Ser Pro His Glu
2885                 2890                2895

Leu Asn Arg Val Ala Gly Ala Leu Arg Lys Leu Gly Val Pro Pro
2900                 2905                2910

Leu Arg Ala Trp Arg His Arg Ala Arg Ala Val Arg Ala Lys Leu
2915                 2920                2925

Ile Ala Gln Gly Gly Arg Ala Lys Ile Cys Gly Ile Tyr Leu Phe
2930                 2935                2940

Asn Trp Ala Val Lys Thr Lys Leu Lys Leu Thr Pro Leu Pro Ala
2945                 2950                2955

Ala Ala Lys Leu Asp Leu Ser Gly Trp Phe Thr Val Gly Ala Gly
2960                 2965                2970

Gly Gly Asp Ile Tyr His Ser Met Ser His Ala Arg Pro Arg Tyr
2975                 2980                2985

Leu Leu Leu Cys Leu Leu Leu Leu Thr Val Gly Val Gly Ile Phe
2990                 2995                3000

Leu Leu Pro Ala Arg
    3005
```

<210> SEQ ID NO 3
<211> LENGTH: 9637
<212> TYPE: DNA
<213> ORGANISM: Hepatitis C virus

<400> SEQUENCE: 3
gcctgcctct tacgaggcga cactccacca tggatcactc ccctgtgagg aacttctgtc    60

```
ttcacgcgga aagcgcctag ccatggcgtt agtacgagtg tcgtgcagcc tccaggaccc     120
cccctcccgg gagagccata gtggtctgcg gaaccggtga gtacaccgga atcgctgggg     180
tgaccgggtc ctttcttgga gcaacccgct caatacccag aaatttgggc gtgccccgc      240 gagatcacta gccgagtagt gttgggtcgc gaaaggcctt gtggtactgc ctgatagggt     300
gcttgcgagt gccccgggag gtctcgtaga ccgtgcaaca tgagcacact tcctaaacct    360
caaagaaaaa ccaaaagaaa caccatccgt cgcccacagg acgttaagtt cccgggtggc    420
ggacagatcg ttggtggagt atacgtgttg ccgcgcaggg gcccacgatt gggtgtgcgc    480
gcgacgcgta aaacttctga acggtcacag cctcgcggac gacgcagcc tatccccaag    540 gcgcgtcgga gcgaaggccg gtcctgggct cagcccgggt acccttggcc cctctatggt    600
aatgagggct gcgggtgggc agggtggctc ctgtccccgc gcggctcccg tccatcttgg    660
ggcccaaacg accccggcg gaggtcccgc aatttgggta aagtcatcga taccctacg     720 tgcggattcg ccgacctcat ggggtacatc ccgctcgtcg gcgctcccgt aggaggcgtc    780
gcaagagccc tcgcgcatgg cgtgagggcc cttgaagacg ggataaattt tgcaacaggg    840
aacttgcccg gttgctcctt ttctatcttc cttcttgctc tgttctcctg cttagttcat    900
cctgcagcta gtcttgagtg gcggaatacg tctggcctct atgtccttac caacgactgt    960
tccaatagca gtattgtgta tgaggccgat gacgtcattc tgcacacacc cggctgtgta   1020
ccttgtgttc aggacgacaa tacatccacg tgctggaccc cagtgacacc tacggtggca   1080
gtcaggtacg tcggagcaac caccgcttcg atacgcagtc atgtggacct attagtgggc   1140
gcggccacgc tgtgctctgc gctctatgtg ggtgatatgt gtggggccgt ctttctcgtg   1200
ggacaagcct tcacgttcag acctcgtcgc catcaaacgg tccagacctg taactgctcg   1260
ctgtacccag gccatgtttc aggacatcga atggcttggg atatgatgat gaattggtcc   1320
cccgctgtgg gtatggtggt ggcgcacatc ctgcgattgc cccagacctt gtttgacata   1380
ctggccgggg cccattgggg catcttggcg ggcctagcct attattctat gcagggcaac   1440
tgggccaagg tcgctattgt catgattatg ttttcagggg tcgatgctga acatatgtc   1500 accggtggca gtgtagctca tagtgccaga gggttaacta gcctttttag tatgggcgcc   1560
aagcagaaac tgcaattggt caacaccaat ggctcgtggc acatcaacag tactgccctg   1620
aactgcaatg agtccataaa caccgggttc atagctgggt tgttttatta ccataagttc   1680
aactctactg gatgtcctca aaggcttagc agctgcaagc ccatcatttc cttcaggcag   1740
gggtggggcc ccttgacaga tgctaacatc accggtcctt ctgatgatag accgtattgc   1800
tggcactacg cacctagacc ttgtagtgtt gtcccggcat caagtgtctg cggccctgtg   1860
tactgcttca ccatcgcc agtggtcgta ggcactactg atatcaaagg caagccgacc    1920
tacaactggg gtgagaatga gacagatgtg ttcctgctgg agtccctgcg gcctcccagt   1980
ggccggtggt ttggatgcgc gtggatgaac tccacggggt tcctcaagac gtgtggagct   2040 ccccccttgta acatctatgg gggtgagggg gatcccgaaa atgagacaga cctcttctgc   2100
cccaccgact gcttcaggaa acatcctgag gccacataca gccggtgtgg tgcggggccc   2160
tggttgacac ctcgctgcat ggtcgactat ccataccggc tttggcatta cccatgtaca   2220
gtcaatttca cattgttcaa ggtgaggatg tttgtgggcg gatttgaaca ccggtttacc   2280
gccgcttgta actggaccag gggggagcgc tgcaatatcg aggatcgtga tcgcagcgag   2340
caacatccgc tgctgcattc aacaactgag cttgctatac tgccttgctc tttcacgccc   2400
atgcctgcat tgtcaacagg tctaatacac ctccaccaaa atatcgtgga tgtccaatac   2460
```

```
ctttatggtg ttggatctga catggtggga tgggcgctga aatgggagtt cgtcatcctc    2520
gttttcctcc tcctggcaga cgcacgcgtg tgcgttgccc tttggctgat gctgatggta    2580
tcacaagcag aagcagcctt ggagaacctt gtcacgctga acgccgtcgc tgctgctggg    2640
acacatggta ttggttggta cctggtagcc ttttgcgcgg cgtggtacgt gcggggtaaa    2700
cttgtcccgc tgacgatcta cggcctgacg ggtctttggt ccctagcatt gcttgtcctc    2760
ttgctccccc aacgggcgta tgcttggtcg ggtgaagaca cgcgctactct cggcgctggg    2820 gtcttggccc tcttcggctt cttttacctta tcaccctggt acaagcattg gatcggccgc    2880
ctcatgtggt ggaaccagta cactatatgt agatgcgagg ccgcccttca agtgtgggtc    2940 cccccttac ttgcacgcgg gagtagggac ggtgtcatcc tgctaacaag cttgctttat    3000
ccatccttaa ttttgacat cactaagctg ctgatagcag taataggccc attatactta    3060
atacaggctg ccatcactac caccccctac tttgtgcgcg cacatgtact ggtccgcctt    3120
tgcatgctcg tgcgctccgt gatgggggga aagtacttcc agatggccat actgagcatt    3180
ggcagatggt tcaacaccta cctatatgac cacctagcgc caatgcaaca ttgggccgca    3240
gctggcctca aagacctagc agtggccact gaacctgtaa tatttagtcc catggaaatt    3300
aaggtcatca cctggggcgc ggacacagcg gcttgcggag atattctttg cgggctgccg    3360
gtctccgcgc gattaggccg tgaggtattg ttgggacctg ctgatgatta tcggaaatg    3420 ggttggcgtc tgttggcccc gatcacagca tacgcccagc aaaactaggg ccttcttggg    3480
actattgtga ccagcttgac tggcagggat aagaacattg tgaccggtga agtgcaggtg    3540 cttttctacgg ctacccagac cttcctaggt acaacagtag ggggggttat gtggactgtt    3600
taccatggtg caggttcgaa aacgctcgcg ggcgccaaac atcccgcgct ccaaatgtac    3660
acaaatgtgg atcaggacct cgttgggtgg ccagcccctc caggggctaa gtctcttgaa    3720
ccgtgcgcct gcgggtctgc agacttatac ttggttaccc gcgatgccga tgtcatccct    3780
gctcggcgca gagggactc cacagcgagc ttgctcagtc ctagacctct cgcctgtctc    3840
aaaggttcct ctggaggtcc tgttatgtgc ccttctgggc atgttgcggg gatctttagg    3900
gctgctgtgt gcaccagagg tgtagcaaaa gccctacagt tcgtaccagt ggaaacccctt    3960 agcacacagg ctaggtctcc atctttctct gacaattcaa ctcctcctgc tgttccacag    4020
agctatcaag tagggtacct tcatgccccg accggcagcg gtaagagcac aaaggtcccg    4080
gccgcttatg tagcacaagg atataatgtt ctcgtgctga atccatcggt ggcggccaca    4140
ctaggcttcg gctcttttcat gtcgcgtgcc tatgggatcg accccaacat ccgcactggg    4200
aaccgcaccg tcacaactgg tgctaaacta acctattcca cctacggtaa gtttcttgcg    4260
gacgggggtt gctccggggg ggcatatgat gtgatcatct gtgatgaatg tcatgcccaa    4320
gacgctacta gcatattggg tataggcacg gtcttagatc aggctgagac ggccggggtg    4380
aggttgacgg ttttagcaac agcaactccc ccaggcagca tcactgtgcc acattctaac    4440
atcgaagaag tggccctggg ctctgaaggt gagatcccctt tctacggtaa ggctataccg    4500
atagccctgc tcaagggggg gaggcaccctt atcttttgcc attccaagaa aaaatgtgat    4560
gaggtggcag ccaaactcag aggcatgggg ctcaacgctg tggcgtacta tagggggtctc    4620 gatgtgtccg tcataccaac aacaggagac gtcgtagttt gcgctactga cgccctcatg    4680
actggattca ccggagactt cgattctgtc atagattgca acgtggctgt tgaacagtac    4740
gttgacttca gcctggaccc caccttttcc attgagaccc gcaccgctcc ccaagatgcg    4800
```

```
gtttcccgca gccaacgtcg tggccgtacg ggccgaggta gactcggtac gtaccgatat   4860
gttgccccgg gtgaaagacc gtctggaatg tttgactcgg ttgttctctg tgagtgctat   4920
gacgcgggct gctcgtggta cgatctgcag ccagctgaga ccacagtcag actgagagct   4980
tacttgaaca cgccggggtt acctgtctgc caggaccatt tagacttttg ggagagcgtc   5040
ttcactggat tgactcacat agacgcccac tttctgtcac agactaagca cagggactt    5100
aacttctcgt tcctaactgc ctaccaagcc actgtgtgtg cccgcgcaca ggcttctcca   5160
ccaagttggg acgagacgtg gaagtgcctc gtgcggctta agccaacact acatggacct   5220
acgccccttc tatatcggtt agggcctgtc caaaatgaca tctgcttgac acaccccgtc   5280
acaaaataca tcatggcatg catgtcagct gatctggaag taaccaccag cacctgggtg   5340
ttgcttggag gggtccttgc ggccctagcg gcctactgct tgtcagtcgg ctgcgttgtg   5400
atcgtgggtc atattgagct gagaggcaag ccggcactcg taccggacag agaggtgttg   5460
tatcaacaat acgatgagat ggaggagtgc tcacaagccg ccccatatat cgaacaagct   5520
caggcaatcg cccaccagtt caaggaaaaa atcctaggac tgctgcagcg agccacccag   5580
caacaagctg tcatcgagcc catagtagct accaactggc aaaaacttga gaccttctgg   5640
cacaagcata tgtggaattt tgtgagtggg atccaatacc tagcaggcct ctccactttg   5700
cccggcaacc cagctgtggc gtctcttatg gcgttcactg cttcagtcac cagtcccctg   5760
acgaccaacc agactatgtt ttttaacata ctcgggggggt gggtcgccac ccatttggca   5820
gggccccaga gctcttccgc gttcgtggta agcggcttag ccggcgctgc catagggggt   5880
ataggcctgg gcagggtctt gctggacatc ctggcaggat acggagctgg tgtctcaggc   5940
gccttggtgg ctttttaagat catgggagga gaactcccca ctactgagga catggtcaac   6000
ctgttgcccg ccatactatc tccgggcgct ctcgtcgtcg gtgtgatatg cgctgccata   6060
ctacgtcgac acgtaggacc tggggaggga gcggtacagt ggatgaacag gctcatcgca   6120
ttcgcgtccc ggggcaacca cgtctcacca acgcactatg ttcccgagag cgatgctgca   6180
gcgagggtca ccgcattgct gagttctcta actgtcacaa gtctgctccg gcggttacac   6240
aagtggatca atgaagacta cccaagccct tgcagcggcg attggctgcg tgacatctgg   6300
gactgggttt gctcggtgtt gtccgacttc aagacgtggc tctctgctaa gattatgcca   6360
gcactccctg ggctgcccttt catctcctgt caaaagggat acaagggcgt gtggcggggg   6420
gatggtgtga tgtcgacacg ctgtccttgc ggggcatcaa tcactggcca cgtgaagaat   6480
gggtccatgc ggcttgcggg gccgcgtatg tgtgctaaca tgtggcacgg tactttcccc   6540
atcaatgagt acaccaccgg acccagcaca ccttgcccat cacccaacta cactcgcgca   6600
ctatggcgcg tggctgccag cagctacgtt gaggtgcgcc gggtgggggga cttccattat   6660
attacggggg ctacagaaga tgagctcaag tgtccgtgcc aagtgccggc tgctgagttc   6720
tttactgaag tggatggggt gagactccac cgttacgccc ctccatgtaa gccctgttg    6780
agagaagaga tcactttctc ggtagggttg cattcctacg cgataggatc tcaactcccc   6840
tgtgagccag aaccagatgt ttctgtgttg acctcgatgt tgagagaccc ttctcatatc   6900
accgccgaga cggcagcgcg ccgccttgcg cgcgggtccc ctccatcaga ggcaagctca   6960
tccgccagcc aactatcggc tccgtcgttg aaggccactt gccagacgca taggcctcat   7020
ccagacgctg agctggtgga cgccaacttg ttatggcggc aagagatggg cagcaacatt   7080
acacgggtgg agtctgaaac gaaggttgtg attcttgatt cattcgaacc tctgagagcc   7140
gaagctgacg acgccgagct ctcggtggct gcagagtgtt tcaagaagcc tcccaagtat   7200
```

```
cctccagccc ttcctatctg ggccaggccg gactacaacc ctccactgtt ggaccgctgg    7260
aaagcaccgg attatgtacc accaactgtc catggatgtg ccttaccacc acggggcgct    7320
ccaccggtgc ctcctcctcg gaggaaaaga acaatccagc tggacggctc caatgtgtcc    7380
gcggcgctag ctgcgctagc ggaaaaatca ttcccgaccc caaaatcgca ggaagagaat    7440
agctcatcct ctggggtcga cacacagtcc agcactacct ccaggatgcc cccctctcca    7500
ggaggggagt ccgactcaga gtcatgctcg tccatgcctc ctctcgaggg agagccgggc    7560
gatccggact tgagttgcga ctcttggtcc accgttagtg acaacgagga gcagagcgtg    7620
gtctgctgct ctatgtcgta ctcttggacc ggtgccctga taacaccatg tagtgctgag    7680
gaggagaaac tgcccatcag cccactcagc aattctttgt tgagacatca taacctagtc    7740
tattcaacgt cgtcaagaag cgcttctcag cgtcagagga aggttacctt cgacagactg    7800
caggtgctcg acgaccatta taagactgca ttaaaggagg tgaaggagcg agcgtctagg    7860
gtgaaggccc gcatgctcac catcgaggaa gcgtgcgcgc tcgtccctcc tcactctgcc    7920
cggtcgaagt tcgggtatag tgcgaaggac gttcgctcct tgtccagcag ggccattgac    7980
cagatccgct ccgtctggga ggacctgctg gaagacacca caactccaat tccaaccacc    8040
atcatggcga agaacgaggt gttttgtgtg gaccccgcta aggggggccg caagcccgct    8100
cgcctcattg tgtaccctga tctggggggtg cgtgtctgtg agaaacgcgc cctatatgac    8160
gtgatacaga agttgtcaat tgagacgatg ggttccgctt atggattcca atactcgcct    8220
caacagcggg tcgaacgtct actgaagatg tggacctcaa agaaaacccc cttggggttc    8280
tcatatgaca cccgctgctt tgactcaact gtcactgaac aggacatcag ggtagaagag    8340
gagatatatc aatgctgtaa ccttgaaccg gaggccagga aagtgatctc ctccctcacg    8400
gagcggcttt actgcggggg ccctatgttc aacagcaagg gggcccagtg tggttatcgc    8460
cgttgccgcg ccagtggagt tctgcctacc agctttggca atacaatcac ttgttacatc    8520
aaggccacag cggccgcgaa ggccgcaggc ctccggaacc cggactttct tgtctgcgga    8580
gatgatttgg tcgtggtggc tgagagtgat ggcgtcgatg aggatagagc agccctgaga    8640
gccttcacgg aggctatgac caggtactct gctccacccg gagatgcccc acagcccacc    8700
tatgaccttg agctcattac atcttgctcc tctaacgtct ccgtagcacg ggacgacaag    8760
gggaggaggt attattacct cacccgtgat gccactactc cctagcccg cgcggcttgg    8820 gaaacagccc gtcacactcc agtcaactcc tggttaggta acatcatcat gtacgcgcct    8880
accatctggg tgcgcatggt aatgatgaca cactttttct ccatactcca atcccaggag    8940
atacttgatc gaccccttga ctttgaaatg tacggggcca cttactctgt cactccgctg    9000
gatttaccag caatcattga aagactccat ggtctaagcg cattcacgct ccacagttac    9060
tctccagtag agctcaatag ggtcgcgggg acactcagga agcttgggtg ccccccccta    9120
cgagcttgga gacatcgggc acgagcagtg cgcgccaagc ttatcgccca gggagggaag    9180
gccaaaatat gcggccttta tctcttcaat tgggcggtac gcaccaagac caatctcact    9240
ccactgccag ccactggcca gttggatttg tccagctggt ttacggttgg tgtcggcggg    9300
aacgacattt atcacagcgt gtcacgtgcc cgaacccgcc atttgctgct ttgcctactc    9360
ctactaacgg taggggtagg catctttctc ctgccagctc ggtgagctgg taggataaca    9420
ctccattctt tttttttttt tttttttttt tttttttttt tttttttttt tttttttttt    9480
tttttttttt ttttctttt cctttcccct tcttttctga cctttaatct tccttcttag    9540
```

```
gtggctccat cttagcccta gtcacggcta gctgtgaaag gtccgtgagc cgcatgactg    9600
cagagagtgc tgatactggc ctctctgcag atcatgt                             9637

<210> SEQ ID NO 4
<211> LENGTH: 9579
<212> TYPE: DNA
<213> ORGANISM: Hepatitis C virus

<400> SEQUENCE: 4
acctgctctc tatgagagca acactccacc atgaaccgct ccctgtgag gaactactgt       60 cttcacgcag aaagcgtcta gccatggcgt tagtatgagt gttgtacagc ctccaggacc     120 cccctcccg ggagagccat agtggtctgc ggaaccggtg agtacaccgg aatcgccggg      180
atgaccgggt cctttcttgg attaacccgc tcaatgcccg gaaatttggg cgtgccccg      240 caagactgct agccgagtag tgttgggtcg cgaaaggcct tgtggtactg cctgataggg     300
tgcttgcgag tgccccggga ggtctcgtag accgtgcacc atgagcacga atcctaaacc     360
tcaaagaaaa accaaacgta acaccaaccg ccgcccaatg acgttaagt tcccgggtgg     420 tggccagatc gttggcggag tttacttgtt gccgcgcagg ggcccagat gggtgtgcg      480 cgcgactcgg aagacttcgg agcggtcgca acctcgtgga agacgccaac ctatccccaa     540
ggcgcgtcga cccgagggaa ggtcctgggc acaaccagga tatccatggc ctctttacgg     600
taatgagggt tgtgggtggg caggatggct cttgtccccc gtggctctc gaccgtcttg      660 ggcccaaat gatccccggc ggaggtcccg caatttgggt aaggtcatcg atacctaac       720 ctgcggcttc gccgacctca tgggatacat cccgctcgta ggcgccccg tgggtggcgt      780 cgccagggcc ctggcacatg tgtcagggc tttggaggac gggatcaatt atgcaacagg     840
gaatctcccc ggttgctcct tttctatctt cctcttggca cttctttcgt gcctgactgt     900
ccccgcttcg gccgttaact atcgcaatgt ctcgggcatc taccatgtca ccaatgactg     960
cccgaattca agcatagtgt atgaggccga ccatcacatc ttgcacctc caggttgcgt    1020 gccctgcgtg agagagggga atcagtcacg ctgctgggtg gcccttactc ctaccgtcgc    1080
agcgccatac atcggcgcac gcttgagtc cttacggagt catgtggatt tgatggtggg    1140
ggccgccact gttttgctcgg gtctttacat cggggacctg tgtggcggct tgttcctagt    1200
tggccagatg ttttcattcc gaccacggcg ccactggacc acccaggatt gcaattgttc    1260
catctacaca gggcacatta caggccacag aatggcctgg gacatgatga tgaactggag    1320
tccaacaacc accttagttc tcgcccaggt catgaggatc ccaaccactc tggtagactt    1380
actctctgga ggccactggg gtgtcctcgt gggagtggcc tatttcagca tgcaggccaa    1440
ttgggccaaa gtcatcttgg tcctattcct ctttgcaggg gttgatgccg agactcacgt    1500
gtctggggca gcagtcggcc ggagtaccgc cggcttggct aacctctttt cttctgggtc    1560
taagcagaat ttacagctca tcaacagcaa tgggagctgg catataaata ggactgccct    1620
taactgcaat gacagcttaa acactgggtt cttggctagc ttgttctaca cccacaagtt    1680
taacagctca gggtgttccg aacggctcgc gtgctgcaag agccttgaca gctacggcca    1740 aggctgggggc ccactcgggg tcgctaacat cagcggctcg tctgatgaca ggccttattg    1800
ctggcactac gcgcctcggc cgtgcgggat tgtgccagca tccagtgtgt gtggccccgt    1860
gtattgtttc actcccagcc ctgtcgtggt cggtactact gatcacgtcg gggtccctac    1920
ttacacctgg ggggagaatg agactgatgt cttccttttg aactcgacca gccgccgca    1980 tggtgcgtgg tttggatgcg tgtggatgaa cagtaccggg ttcaccaaaa cctgtggcgc    2040
```

```
ccctccatgc gaggttaaca ccaataatgg gacctggcac tgccccaccg attgcttcag    2100
gaagcatccg gagactacct acgccaagtg cggatcaggg ccttggatca caccgcgctg    2160
cctgattgat tacccgtacc ggctgtggca tttcccgtgc accgccaact tctccgtctt    2220
taacatcagg acatttgtcg gcggtataga gcatcggatg caagcggcat gcaactggac    2280
cagggggggaa gtctgtggct tggagcacag ggatcgcgta gagctatcac ccctgctcct    2340
taccactaca gcgtggcaga tcctcccctg ctctttcacc actttacctg ccctctccac    2400
cggcttgatc cacctccacc aaaatatcgt ggacgtccag tacctctatg gtgttgggtc    2460
tgcagtggta tcttgggccc ttaagtggga atatgtggtg ctcgcgttcc tgcttctcgc    2520
ggacgcgaga gtctctgcct gcctatggat gatgtttatg gtaagtcaag ttgaggcggc    2580
tctgtccaac ctgattaaca tcaatgctgc ttcagccgct ggtgcccaag gcttctggta    2640
cgccatcctc ttcatctgca ttgtctggca tgtcaagggc cggttcccag ctgctgctgc    2700
ctacgcagcc tgcgggctgt ggcccctgtt tctcctgctt ctgatgctgc tgagagggc    2760
ttatgcatac gaccaggaag tggcagggtc ccttggcggc gccatcgttg tcatgctgac    2820
cattctgaca ctgtctccgc actacaagtt atggctggct aggggattgt ggtggatcca    2880
atattttata gctaggaccg aggctgtgct gcatgtctat attccatcct tcaacgtgcg    2940
cgggcctcgc gactcagtga ttgttcttgc agtcctggtc tgtccacacc tagtatttga    3000
catcacaaaa tatcttctgg ccatcttagg gcccctccac atactccagg cctcgctcct    3060
acgcatccct tactttgtga gggcacaagc gctggttaag atctgcagct tgttgcgtgg    3120
ggtagtttat ggcaagtact tccaaatggt cgtgcttaaa gcaggggccc tgactggtac    3180
ttacatctat gaccacctta ctcccatgtc agattgggcc gctacgggcc tccgcgattt    3240
ggcggtggcc ctagagccag ttgtgttcac gcccatggag aagaaagtca tcgtctgggg    3300
cgctgacacc gctgcgtgcg gagacatcat aaggggatta cctgtttcgg ccaggttggg    3360
caatgaaatc ttgctcggac cagccgatac agaaacatca aagggggtgga gactccttgc    3420
ccccatcaca gcatacgcgc agcagacccg cggcttgttc agcaccatcg taacgagcct    3480
cactggcagg gacaccaatg agaattgtgg cgaagtgcag gtcttatcca ccgctacgca    3540
gtccttcctg ggtactgcgg ttaacggcgt gatgtggacc gtctaccacg ggcgggtgc    3600
caagaccatc agcggcccga agggacctgt caatcaaatg tacactaatg ttgaccaaga    3660
cttggtgggg tggccagcac ccccggagt cagatctctt gctccgtgca cctgcggctc    3720
ggcagacttg tatctagtca ccaggcacgc agatgtaata cccgtgcgca ggagaggaga    3780
caccagagga gctctcttga gccctagacc aatatccact cttaagggat cttccggagg    3840
tccgctgctg tgcccatgg gacacgccgc cggcatattc cgtgcggcgg tgtgtactcg    3900
aggggtagcc aaggcggtag acttcgtccc ggttgaatct cttgagacta ccatgagatc    3960
accagtgttc actgacaact caacacctcc agcagtgccc cagacctacc aggtcgcgca    4020
cctacacgca ccaacaggaa gtggcaagag caccaaagtc ccggcggcgt atgctgccca    4080
aggctataaa gtgctagtgc tcaatccttc ggttgcggcc acactgggtt ttgggggtata    4140
catgtccaag gcatatggca tcgacccgaa catccggtcg ggagtcagga ccatcaccac    4200
gggtgcgcca atcacgtact caacgtatgg taagttcctg gctgatggag gttgcagcgg    4260
aggggcatac gacataatca tctgtgacga gtgccattcc actgactcca caacgatcct    4320
tggcataggc acagtcctgg accaagcgga gaccgctgga gtgcgcctca ccgtgctcgc    4380
```

```
gactgctact ccgccagggt cagtgactac acctcattcc aacatagagg aggtcgccct    4440
gccaacaacg ggggaaatcc ccttttacgg caaggcgatc cctctggagc tgattaaggg    4500
gggcagacat ctcatcttct gccactcaaa gaaaaagtgt gatgaactgg ccagacaact    4560
gacatctctt ggtctgaatg ccgtagccta ctacagaggc ttagacgttt cggtgattcc    4620
cacgtctggg gacgtcgtgg tatgcgccac ggacgccctc atgacgggtt ttaccggcga    4680
ctttgactca gtgatagact gcaatacatc tgtgatacag actgttgact tcagcttgga    4740
ccccaccttc tccatagaga ctacaaccgt tccccaggac gcggtatccc gcagccagcg    4800
gagaggccgc actggtaggg ggaggttggg cacataccgg tatgtcaccc cgggagagag    4860
accatcaggc atgtttgaca ctgcagtgct ttgcgagtgc tacgatgccg ggtgtgcctg    4920
gtacgagctg acacctgctg aaaccacaac aaggctgaaa gcttacttcg acacaccagg    4980
ccttcctgtg tgccaagacc atctggagtt ctggagagc gtctttacag ggttaaccca     5040
catagacggt catttcctat cccagaccaa gcaatcgggt gagaatttcc cgtatcttgt    5100
tgcttaccaa gccacggtgt gcgccaaggc tctggcgcct ccaccaagct gggacaccat    5160
gtggaagtgc ctaattcgcc ttaagcccac cctgcacggg cccacacccc tcctctacag    5220
actgggtct gtgcagaatg aagtggtgct cacccatccc atcaccaaat acatcatggc     5280
ttgcatgtca gctgatctcg aggtagtgac aagtacgtgg gtcttggtgg gcggcgtcct    5340
ggcagctctg gctgcttact gtctttcagt gggcagcgta gtgattgttg ggagagtcgt    5400
cctgtcgggc caacctgctg tcattcccga tcgcgaagtg ctctaccaac agttcgacga    5460
aatggaggag tgttccaaac acctcccact agtcgagcac gggttacaac tggctgagca    5520
gttcaagcag aaggccttag gtctcctaaa tttcgctggc aagcaagccc aagaggcaac    5580
accagtgatc cagtctaact tcgctaaact tgagcagttt tgggcgaagc acatgtggaa    5640
tttcatcagc ggcattcaat atctcgctgg actgtctacc ttgccaggca atcctgccat    5700
tgcttccctc atgtccttta ctgctgctgt tacaagccct ctgaccaccc aacaaaccct    5760
ccttttaac atcttggggg atgggtggc ctcgcagatt gcgactccga cggcttctac       5820
cgcattcgtc gtgagcggct tggcggggc ggcagttggc agtgtgggcc ttggcaaaaat     5880
tttggtggac attctcgccg gttacggcgc cggcgtagct ggcgctgtgg ttaccttcaa    5940
gatcatgagc ggcgagatgc cttccacaga ggacttggta aatttgctcc cggccattct    6000
atcgcccgga gcattggtag tgggggtggt atgcgcggcg attttgcgcc gccacgtggg    6060
cccgggcgaa ggggctgtgc agtggatgaa ccgtctaatt gcgttcgcat cgcgaggcaa    6120
tcacgtgtct cccacgcatt acgtccctga gtccgacgcg gcagcccgcg tgaccaccat    6180
actatcatcc ctcactgtga catcccttct cagacgcctc cacaagtgga tcaatgaaga    6240
ttgctccacc ccatgtgccg aatcttggct atgggaggta tgggattggg tctgcaccgt    6300
gctgagtgac ttcaagacgt ggctaaaagc caagttgctg ccctcatgc caggcatccc      6360
cttcctctca tgccagaggg gctataaggg agagtggcgc ggagatggcg tgatgcatac    6420
cacatgcccc tgcggagcag atctggcagg tcacatcaag aacggctcga tgagaatcac    6480
cgggccgaaa acctgcagca acacatggca tggtaccttc cccatcaatg cttacaccac    6540
aggccctggt gtaccatcc cggcgccgaa ctacaagttc gcgctttgga gggtgtccgc    6600
cgaggactac gtgaggttc gcagagtggg tgatttccat tatgtcaccg gggtaacaca     6660
agacaacatc aagtgcccct gccaagttcc ggccccagag ttcttcacgg aagtggacgg    6720
catcaggcta caccgccacg ccccgaagtg caaaccccttg ctgcgggacg aagtgtcgtt   6780
```

```
ctcagtagga ctcaattcgt tcgtagtggg atcacaactc ccatgcgagc cagagccgga   6840
cgtggcagtg ctaacatcca tgctgacaga cccatcacac ataacggcgg aatcggcgcg   6900
tcggagattg gctcgagggt cacgaccctc gctagctagt tcctcggcga gtcagctttc   6960
cgccccgtct ctcaaggcca cgtgtaccgc tccccatgac tcccctggta ctgatctcct   7020
cgaggctaac ctcttgtggg ggtctaccgc taccagggtt gagacggacg agaaggtaat   7080
aatactagac tcttttgagt catgtgtggc tgagccaaat gatgacaggg aagtctcggt   7140
tgccgcggaa atcctgcgtc cgaccaagaa gttccctcca gcactaccga tctgggcccg   7200
gccggattac aatccacctc ttaccgagac gtggaagcag caggactaca agcctccgac   7260
cgtccacggg tgcgctctgc ctcccggcaa gcagcccccc gttcctcctc ccaggaggaa   7320
acggacggta cagctcactg agtccgttgt ttctaccgct ttggcagagc tggccgcaaa   7380
gacctttggc cagtcagagc cgagctcaga ccgtgataca gaccttacca ccccaactga   7440
gaccacagac tcgggcccca tcgtcgtgga tgatgcatcc gatgacggat cttattcgtc   7500
aatgcctcca ctagaggggg agcccggtga cccggacttg acatcagact cttggtccac   7560
tgttagcgga tcggaggacg tcgtgtgctg ctcaatgtca tattcatgga ctggggcgct   7620
tgtaacacct tgcgcggctg aagaatcaaa gctgccaatt agcccccctga gcaattcact   7680
tttgcgccat cacaatatgg tgtatgccac gaccacccgt tctgctgtga cacggcagaa   7740
gaaggtgacc ttcgaccgcc tgcaggtggt ggacagtcac tacaatgaag tgcttaagga   7800
gataaaggca cgagcatcca gagtgaaggc acgcttgctt accacagagg aagcttgcga   7860
cctgacgccc ccccactcag ccagatcaaa gttcggctac ggggcgaagg atgttcggag   7920
ccattcccgc aaggccatta accacatcag ctccgtgtgg aaggacttgc tggacgacaa   7980
caataccccca ataccaacaa caatcatggc caaaaatgag gtcttcgctg tgaacccagc   8040
gaagggaggt cggaagcctg ctcgcctgat cgtgtatccg gatctcgggg tccgggtttg   8100
cgagaagaga gcgcttcacg acgtcatcaa aaaactgcct gaggccgtga tgggagccgc   8160
ttatggcttc caatactccc cagcgcagcg ggtggaattt cttctgactg cttggaagtc   8220
gaagaagacc ccaatggggt tctcttatga tacccgctgc tttgactcca ctgtaaccga   8280
aaaggacatc agggtcgagg aagaggtcta tcagtgttgt gacctggagc ccgaagcccg   8340
caaagtcatc accgccctca cagatagact ctatgtgggc ggcccctatgc acaacagcaa   8400
gggagacctt tgtgggtatc ggagatgtcg cgcaagcggc gtctacacca ccagcttcgg   8460
gaacacgctg acgtgctatc tcaaagccac ggccgccatc agggcggcgg ggctgagaga   8520
ctgcactatg ttggtttgcg gtgatgactt agtcgtcatc gctgagagcg acggcgtaga   8580
ggaggacaac cgagccctcc gagccttcac ggaggctatg acgagatact cggctccccc   8640
aggtgacgcc ccgcagccag catatgacct ggaactaata acatcatgtt catccaacgt   8700
ctcagtcgcg cacgacgtga cgggtaaaaa ggtatattac ctaacccgag accctgaaac   8760
tcccttggcg cgagccgcat gggagacagt ccgacacact ccagtcaatt cctggttggg   8820
aaacatcata gtctacgctc ccacaatatg ggtgcgcatg atattgatga cccactttt   8880
ctcaatactc cagagccagg aagcccttga gaaagcactc gacttcgata tgtacggagt   8940
cacctactct atcactccgc tggatttacc ggcaatcatt caaagactcc atggcttaag   9000
cgcgttcacg ctgcacggat actctccaca cgaactcaac cgggtggccg gagccctcag   9060
aaaacttggg gtaccccgc tgagagcgtg gagacatcgg gcccgagcag tccgcgctaa   9120
```

-continued

| | |
|---|---|
| gcttatcgcc cagggaggta gagccaaaat atgtggcata tacctcttta actgggcggt | 9180 |
| aaaaaccaaa ctcaaactca ctccattgcc tgccgctgcc aaactcgatt tatcgggttg | 9240 |
| gtttacggta ggcgccggcg ggggagacat ttatcacagc atgtctcatg cccgaccccg | 9300 |
| ctatttactc ctgtgcctac tcctacttac agtaggggta ggcatcttcc tgctgcctgc | 9360 |
| tcggtaggca gcttaacact ccgaccttag ggtccccttg ttttttttt ttttttttt | 9420 |
| ttttttttt ttttttttt ttttttcctt tccttctttc ctttcctaat ctttctttct | 9480 |
| tggtggctcc atcttagccc tagtcacggc tagctgtgaa aggtccgtga gccgcatgac | 9540 |
| tgcagagagt gctgatactg gcctctctgc agatcatgt | 9579 |

INFECTIOUS HEPATITIS C VIRUSES OF GENOTYPE 3A AND 4A AND USES THEREOF

TECHNICAL FIELD OF THE INVENTION

The present invention relates to molecular approaches to the production of nucleic acid sequences, which comprises the genome of infectious hepatitis C virus. In particular, the invention provides nucleic acid sequences, which comprise the genomes of infectious hepatitis C viruses of either genotype 3a (strain S52) or genotype 4a (strain ED43). The invention therefore relates to the use of the nucleic acid sequences and polypeptides encoded by all or part of the sequences in the development of vaccines and diagnostic assays for HCV and in the development of screening assays for the identification of antiviral agents for HCV. The invention therefore also relates to the use of viral particles derived from laboratory animals infected with S52 and ED43 viruses.

BACKGROUND OF THE INVENTION

Hepatitis C virus (HCV) has a positive-sense single-strand RNA genome and is a member of the genus Hepacivirus within the Flaviviridae family of viruses (Rice, 1996). As for all positive-stranded RNA viruses, the genome of HCV functions as mRNA, from which all of the viral proteins necessary for propagation are translated.

The viral genome of HCV is approximately 9600 nucleotides (nts) in length and consists of a highly conserved 5' untranslated region (UTR), a single long open reading frame (ORF) of approximately 9,000 nts and a complex 3' UTR. The 5' UTR contains an internal ribosomal entry site.

The 3' UTR consists of a short variable region, a polypyrimidine tract of variable length and, at the 3' end, a highly conserved region of approximately 100 nucleotides. The last 46 nucleotides of this conserved region were predicted to form a stable stem-loop structure thought to be critical for viral replication.

The ORF encodes a large polypeptide precursor that is cleaved into at least 10 proteins by host and viral proteinases. These proteins are the structural proteins Core, E1, E2; p7; and the nonstructural proteins NS2, NS3, NS4A, NS4B, NS5A, NS5B. The predicted envelope proteins contain several conserved N-linked glycosylation sites and cysteine residues. The NS3 gene encodes a serine protease and an RNA helicase and the NS5B gene encodes an RNA-dependent RNA polymerase.

A remarkable characteristic of HCV is its genetic heterogeneity, which is manifested throughout the genome. The most heterogeneous regions of the genome are found in the envelope genes, in particular the hypervariable region 1 (HVR1) at the N-terminus of E2. HCV circulates as a quasispecies of closely related genomes in an infected individual. Globally, seven major HCV genotypes (genotypes 1-6) and multiple subtypes (a, b, c, etc.) have been identified.

The nucleotide and deduced amino acid sequences among isolates within a quasispecies generally differ by 1-2%; those of different strains/isolates differ by 2-10%, whereas isolates of different subtypes and genotypes usually vary by>20% and>30%, respectively. Genotypes 1, 2 and 3 are found worldwide and constitute more than 90% of the HCV infections in North and South America, Europe, Russia, China, Japan and Australia. Throughout these regions genotype 1 accounts for the majority of HCV infections but genotypes 2 and 3 each account for significant percentage of infections.

More than 80% of individuals infected with HCV become chronically infected and these chronically infected individuals have a relatively high risk of developing chronic hepatitis, liver cirrhosis and hepatocellular carcinoma. The only currently licensed therapy for chronic hepatitis C, interferon-alfa2 (IFN) in combination with ribavirin, induces a sustained viral response in less than 50-80% of treated patients depending on genotype. Consequently, HCV is currently the most common cause of end stage liver failure and the reason for about 30% of liver transplants performed in the U.S.

In addition, a number of recent studies suggested that the severity of liver disease and the outcome of therapy may be genotype-dependent. In particular, these studies suggested that infection with HCV genotype 1b and 3a were associated with more severe liver disease and that HCV genotype 1a and 1b might be associated with a poorer response to IFN therapy. As a result of the inability to develop a universally effective therapy against HCV infection, it is estimated that there are still more than 40,000 new infections yearly in the U.S. and about 3 million worldwide. Moreover, since there is no vaccine for HCV and as mentioned no effective treatment, HCV remains a serious public health problem.

Despite the intense interest in the development of vaccines and therapies for HCV, progress has been hindered by the absence of a useful cell culture system and the lack of convenient small animal models for laboratory study. For example, while replication of HCV in several cell lines has been reported, such observations have turned out not to be highly reproducible. And as described below only the JFH1 starin of HCV genotype 2a can grow in culture. The chimpanzee is the only HCV pathogenesis animal model. Consequently, HCV has been studied mainly by using clinical materials obtained from patients or experimentally infected chimpanzees, an animal model whose availability is very limited.

However, several researchers have recently reported the construction of infectious cDNA clones of HCV, the identification of which would permit a more effective search for susceptible cell lines and facilitate molecular analysis of the viral genes and their function.

Kolykhalov et al., (1997) and Yanagi et al. (1997, 1998) reported the derivation from HCV strains H77 (genotype 1a) and HC-J4 (genotype 1b) of cDNA clones of HCV that are infectious for chimpanzees. Subsequently, several other cDNA clones of genotype 1a (strains HCV-1 and TN), 1b (strains Con1 and HCV-N) and 2a (strains J6 and JFH1) were developed. However, while these infectious clones will aid in studying HCV replication and pathogenesis and will provide an important tool for development of in vitro replication and propagation systems, it is important to have infectious clones of all major HCV genotypes, given the extensive genetic heterogeneity of HCV and the potential impact of such heterogeneity on the development of effective therapies and vaccines for HCV.

In addition, synthetic chimeric viruses can be used to map the functional regions of viruses with different phenotypes. In flaviviruses and pestiviruses, infectious chimeric viruses have been successfully engineered to express different functional units of related viruses and in some cases it has been possible to make chimeras between non-related or distantly related viruses. For instance, the IRES element of poliovirus or bovine viral diarrhea virus has been replaced with IRES sequences from HCV.

The construction of an infectious chimera of two closely related HCV subtypes has been reported. The chimera contained the complete ORF of a genotype 1b strain but had the 5' and 3' termini of a genotype 1a strain (Yanagi et al., 1998).

Recently, it was shown, that transfection of RNA transcripts from cDNA clone of genotype 2a isolate JFH1 into Huh7 hepatoma cells led to productive infection of these cells with JFH1 virus (Wakita 2005, Zhong 2005). It is not known, why JFH1 can grow in cell culture and other HCV isolates cannot. To exploit the exceptional growth characteristics of JFH1 in cell culture, the construction of JFH1-based intra- and intergenotypic recombinants became a research focus. Thus, intragenotypic and intergenotypic recombinants have been constructed containing non structural proteins NS3-NS5B of genotype 2a isolate JFH1 and Core, E1, E2, p7, and NS2 from genotype 1a (strain H77 and TN), 1b (strain J4 and Con-1), 2a (strain J6), 2b (strain J8), 3a (strain S52, DBN, and 452), 4a (strain ED43), 5a (strain SA13), 6a (strain HK6a), and 7a (strain QC69). Transfection of RNA transcripts of cDNA clones of these recombinants led to productive infection of Huh7.5 human hepatoma cells (Pietschmann 2006, Gottwein 2007, Scheel 2008, Jensen 2008, Gottwein, 2009). However, for most of the intergenotypic recombinants, viability in Huh7.5 cells required acquisition of cell culture adaptive mutations, possibly enabling interaction of proteins of different genotype isolates. J6/JFH1 has also been found to be viable in chimpanzees and in the SCID-uPA mouse model (Lindenbach 2005, Lindenbach 2006).

SUMMARY OF THE INVENTION

The present invention relates to nucleic acid sequences, which comprise the genomes of infectious hepatitis C viruses and in particular, nucleic acid sequences which comprises the genome of infectious hepatitis C viruses of genotypes 3a (strain S52) and 4a (strain ED43).

The present invention also relates to a method for producing a hepatitis C virus comprising transfecting a host cell with an RNA transcript of the nucleic acid of the present invention.

The invention further relates to polypeptides encoded by a nucleic acid sequence of the present invention.

An aspect of the present invention relates to a method for assaying candidate antiviral agents for activity against HCV, comprising; exposing a cell or a laboratory animal model containing the hepatitis C virus to the candidate antiviral agent; and measuring the presence or absence of hepatitis C virus replication or correlates thereof in the cell or in the animal.

The present invention also relates to an antiviral agent identified as having antiviral activity for HCV by the methods described herein.

In addition, the present invention relates to an antibody to the polypeptides and the hepatitis C viruses of the present invention.

The present invention relates to a composition comprising nucleic acid molecule and/or polypeptides of the present invention suspended in a suitable amount of a pharmaceutically acceptable diluent or excipient.

BRIEF DESCRIPTION OF THE FIGURES

FIG. 3
Genetic heterogeneity of S52 virus population from chimpanzee acute phase plasma pool.

FIG. 4

Comparison of ORF sequence of S52 with that of other genotype 3a isolates

FIG. 5

Genetic heterogeneity of ED43 virus population from chimpanzee acute phase plasma pool.

FIG. 6
Comparison of ORF sequence of ED43 derived from chimpanzee plasma pool with ORF of other genotype 4a isolates.

FIG. 7 3' UTR variable and poly U region of pS52 (nucleotides 9403 to 9451 of SEQ ID NO: 3) and other genotype 3a isolates.

FIG. 8 3' UTR variable and poly U region of pED43 (nucleotides 9365 to 9416 of SEQ ID NO: 4) and other genotype 4a isolates.

Figure 1:
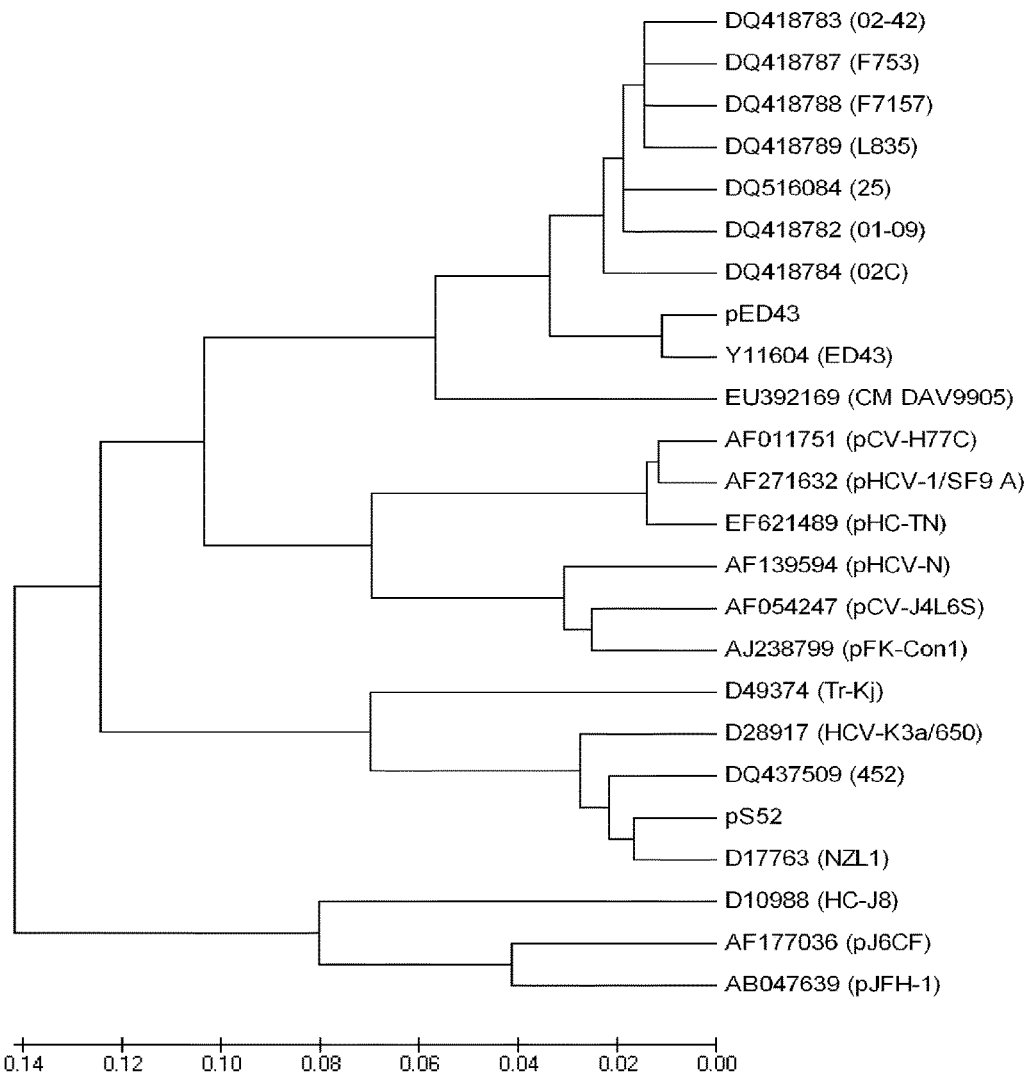
FIG. 1
Phylogenetic tree of pS52, pED43 and representative HCV cDNA clones and isolates of HCV genotypes 1-4.

The present invention will now be described in more detail in the following.

DETAILED DESCRIPTION OF THE INVENTION

Nucleic Acid Molecules and Sequence Identity

It is an object of the invention to provide nucleic acid sequences, which encode infectious hepatitis C viruses. Such nucleic acid sequences are referred to as “infectious nucleic acid sequence”, “nucleic acid sequences of the invention” or “nucleic acid molecules of the present invention” throughout the application.

For the purposes of this application, nucleic acid sequence refers to RNA, DNA, cDNA or any variant thereof capable of directing synthesis of a hepatitis C virus polypeptide by a suitable host organism. It is to be understood that nucleic acid sequences encompasses nucleic acid sequences, which due to degeneracy, encode the same polypeptide sequence as the nucleic acid sequences described herein.

As commonly defined “identity” is here defined as sequence identity between genes or proteins at the nucleotide or amino acid level, respectively. Thus, in the present context “sequence identity” is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two nucleic acid sequences or of two amino acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical nucleic acids or amino acids. Alternatively, alignment of two sequences for the determination of percent identity may be accomplished using a mathematical algorithm. Such an algorithm is incorporated into the NBLAST and XBLAST programs. BLAST nucleotide searches may be performed with the NBLAST program, score=100, word length=12, to obtain nucleotide sequences homologous to a nucleic acid molecules of the invention. BLAST protein searches may be performed with the XBLAST program, score=50, word length=3 to obtain amino acid sequences homologous to a protein molecule of the invention. To obtain gapped alignments for comparison purposes, Gapped BLAST may be utilized. Alternatively, PSI-Blast may be used to perform an iterated search, which detects distant relationships between molecules. When utilizing the NBLAST, XBLAST, and Gapped BLAST programs, the default parameters of the respective programs may be used. See the http world wide web internet site "ncbi.nlm.nih.gov". Alternatively, sequence identity may be calculated after the sequences have been aligned e.g. by the BLAST program in the EMBL database (accessible on the http world wide web internet site "ncbi.nlm.gov/cgi-bin/BLAST"). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

The present invention relates to nucleic acid sequence, which comprises the genome of an infectious hepatitis C virus of genotype 3a or 4a.

An aspect of the present invention relates to an isolated nucleic acid molecule which encodes human hepatitis C virus of genotype 3a, wherein said molecule encodes human hepatitis C virus of genotype 3a with the amino acid sequence according to that of SEQ ID NO: 1 or an amino acid sequence that has a sequence identity of at least 98% to that of SEQ ID NO: 1, such as 90% identity, 91% identity, 92% identity, 93% identity, 94% identity, 95% identity, 96% identity, 97% identity, 98% identity, 98.1% identity, 98.2% identity, 98.3% identity, 98.4% identity, 98.5% identity, 98.6% identity, 98.7% identity, 98.8% identity, 98.9% identity, 99% identity, 99.1% identity, 99.2% identity, 99.3% identity, 99.4% identity, 99.5% identity, 99.6% identity, 99.7% identity, 99.8% identity, or 99.9%.

Another aspect of the present invention relates to an isolated nucleic acid molecule which encodes human hepatitis C virus of genotype 4a, wherein said molecule encodes human hepatitis C virus of genotype 4a with the amino acid sequence according to that of SEQ ID NO: 2 or an amino acid sequence that has a sequence identity of at least 98% to that of SEQ ID NO: 2 such as 90% identity, 91% identity, 92% identity, 93% identity, 94% identity, 95% identity, 96% identity, 97% identity, 98% identity, 98.1% identity, 98.2% identity, 98.3% identity, 98.4% identity, 98.5% identity, 98.6% identity, 98.7% identity, 98.8% identity, 98.9% identity, 99% identity, 99.1% identity, 99.2% identity, 99.3% identity, 99.4% identity, 99.5% identity, 99.6% identity, 99.7% identity, 99.8% identity, 99.9 or 99.9%.

Another aspect of the present invention relates to a nucleic acid molecule that encodes human hepatitis C virus of genotype 3a comprising the nucleic acid sequence according to SEQ ID NO: 3.

In an embodiment of the present invention, the nucleic acid molecule encoding human hepatitis C virus of genotype 3a comprises the nucleic acid sequence according to SEQ ID NO: 3 or nucleic acid sequence with a sequence identity of at least 98% to SEQ ID NO: 3, such as 90% identity, 91% identity, 92% identity, 93% identity, 94% identity, 95% identity, 96% identity, 97% identity, 98% identity, 98.1% identity, 98.2% identity, 98.3% identity, 98.4% identity, 98.5% identity, 98.6% identity, 98.7% identity, 98.8% identity, 98.9% identity, 99% identity, 99.1% identity, 99.2% identity, 99.3% identity, 99.4% identity, 99.5% identity, 99.6% identity, 99.7% identity, 99.8% identity, 99.9 or 99.9%.

Another aspect of the present invention relates to a nucleic acid molecule that encodes human hepatitis C virus of genotype 4a comprising the nucleic acid sequence according to SEQ ID NO: 4.

In an embodiment of the present invention, the nucleic acid molecule encoding human hepatitis C virus of genotype 4a comprises the nucleic acid sequence according to SEQ ID NO: 4 or nucleic acid sequence with a sequence identity of at least 98% to SEQ ID NO: 4, such as 90% identity, 91% identity, 92% identity, 93% identity, 94% identity, 95% identity, 96% identity, 97% identity, 98% identity, 98.1% identity, 98.2% identity, 98.3% identity, 98.4% identity, 98.5% identity, 98.6% identity, 98.7% identity, 98.8% identity, 98.9% identity, 99% identity, 99.1% identity, 99.2% identity, 99.3% identity, 99.4% identity, 99.5% identity, 99.6% identity, 99.7% identity, 99.8% identity, 99.9 or 99.9%.

In one embodiment the genotype 3a is of the strain S52.

In another embodiment the genotype 4a is of the strain ED43.

In one embodiment, the nucleic acid sequences of the invention can be inserted into an expression vector that functions in eukaryotic cells. Eukaryotic expression vectors suitable for producing high efficiency gene transfer in vivo are well known to those of ordinary skill in the art and include, but are not limited to, plasmids, vaccinia viruses, retroviruses, adenoviruses and adeno-associated viruses.

In another embodiment, the sequences contained in the recombinant expression vector can be transcribed in vitro by methods known to those of ordinary skill in the art in order to produce RNA transcripts, which encode the hepatitis C viruses of the invention. The hepatitis C viruses of the invention may then be produced by transfecting cells by methods known to those of ordinary skill in the art with either the in vitro transcription mixture containing the RNA transcripts or with the recombinant expression vectors containing the nucleic acid sequences described herein.

An embodiment of the present invention relates to a DNA construct comprising a nucleic acid molecule of the present invention.

Another embodiment of the present invention relates to an RNA transcript of the DNA construct comprising a nucleic acid molecule of the present invention.

Infectious Nucleic Acid Sequences and Viruses

The invention further relates to mutations of the infectious nucleic acid sequences of the invention where mutation includes, but is not limited to, point mutations, deletions and insertions.

In one embodiment, a gene or fragment thereof can be deleted to determine the effect of the deleted gene or genes on the properties of the encoded virus such as its virulence and its ability to replicate.

In one embodiment, a gene or fragment can be inserted to determine the effect of the insertion. This insertion could be an HCV genome fragment, but also a heterologous sequence, such as a reporter gene.

In an alternative embodiment, a mutation may be introduced into the infectious nucleic acid sequences to examine the effect of the mutation on the properties of the virus.

The invention also relates to the introduction of mutations or deletions into the infectious nucleic acid sequence in order to produce an attenuated hepatitis C virus suitable for vaccine development.

The invention further relates to the use of the infectious nucleic acid sequences to produce attenuated viruses via passage in vitro or in vivo of the viruses produced by transfection of a host cell with the infectious nucleic acid sequences.

The present invention also relates to the use of the nucleic acid sequences of the invention or fragments thereof in the production of polypeptides where "nucleic acid sequences of the invention" refers to infectious nucleic acid sequences, mutations of infectious nucleic acid sequence, chimeric nucleic acid sequence and sequences which comprise the genome of attenuated viruses produced from the infectious nucleic acid sequence of the invention.

The invention further relates to mutations of the infectious nucleic acid sequences where "mutations" include, but are not limited to, point mutations, deletions and insertions. Of course, one of ordinary skill in the art would recognize that the size of the insertions would be limited by the ability of the resultant nucleic acid sequence to be properly packaged within the virion. Such mutations could be produced by techniques known to those of skill in the art such as site-directed mutagenesis, fusion PCR, and restriction digestion followed by religation.

In one embodiment, mutagenesis might be undertaken to determine sequences that are important for viral properties such as replication or virulence. For example, one may introduce a mutation into the infectious nucleic acid sequence, which eliminates the cleavage site between the NS4A and NS4B polypeptides to examine the effects on viral replication and processing of the polypeptide.

Alternatively, one may delete all or part of a gene or of the 5' or 3' untranslated region contained in an infectious nucleic acid sequence and then transfect a host cell (animal or cell culture) with the mutated sequence and measure viral replication in the host by methods known in the art such as RT-PCR. Genes include, but are not limited to, Core, E1, E2, p7, NS2, NS3, NS4A, NS4B, NS5A, and NS5B genes but also the untranslated regions. Of course, those of ordinary skill in the art will understand that deletion of part of a gene, preferably the central portion of the gene, may be preferable to deletion of the entire gene in order to conserve the cleavage site boundaries which exist between proteins in the HCV polyprotein and which are necessary for proper processing of the polyprotein.

In the alternative, if the transfection is into a host animal such as a chimpanzee, one can monitor the virulence phenotype of the virus produced by transfection of the mutated infectious nucleic acid sequence by methods known in the art such as measurement of liver enzyme levels (alanine aminotransferase (ALT) or isocitrate dehydrogenase (ICD)) or by histopathology of liver biopsies. Thus, mutations of the infectious nucleic acid sequences may be useful in the production of attenuated HCV strains suitable for vaccine use.

The invention also relates to the use of the infectious nucleic acid sequence of the present invention to produce attenuated viral strains via passage in vitro or in vivo of the virus produced by transfection with the infectious nucleic acid sequence.

In an embodiment of the present invention the molecule of the present invention is capable of expressing HCV when transfected into cells.

In another embodiment of the present invention the molecule of the present invention is capable of infectivity in vivo.

An embodiment of the present invention relates to an in vivo or an in vitro cell transfected with the DNA comprising a nucleic acid molecule of the present invention.

In an embodiment of the present invention these cells are mammalian cells such as human cells.

In an embodiment of the present invention these cells are mammalian cells such as chimpanzee cells.

Another embodiment of the present invention relates to a cell transfected with an RNA transcript of the DNA comprising a nucleic acid molecule of the present invention or an RNA transcript of the nucleic acid molecule of the present invention.

The present invention therefore relates to the use of the nucleic acid sequence of the invention to identify cell lines capable of supporting the replication of HCV.

In particular, it is contemplated that the mutations of the infectious nucleic acid sequence of the invention and the production of chimeric sequences as discussed above may be useful in identifying sequences critical for cell culture adaptation of HCV and hence, may be useful in identifying cell lines capable of supporting HCV replication.

Transfection of tissue culture cells with the nucleic acid sequences of the invention may be done by methods of transfection known in the art such as electroporation, precipitation with DEAE-Dextran or calcium phosphate or liposomes.

In one such embodiment, the method comprises the growing of animal cells, especially human cells, in vitro and transfecting the cells with the nucleic acid of the invention, then determining if the cells show indicia of HCV infection. Such indicia include the detection of viral antigens in the cell, for example, by immunofluorescence procedures well known in the art; the detection of viral polypeptides by Western blotting using antibodies specific therefore; and the detection of newly transcribed viral RNA within the cells via methods such as RT-PCR. The presence of live, infectious virus particles following such tests may also be shown by injection of cell culture medium or cell lysates into healthy, susceptible animals, with subsequent exhibition of the signs and symptoms of HCV infection.

An embodiment of the present invention relates to a method for determining the susceptibility of cells in vitro to support HCV infection, comprising the steps of: growing cells in vitro, transfecting into said cells the nucleic acid of the present invention, and determining if said cells show indicia of HCV replication.

Suitable cells or cell lines for culturing HCV include, but are not limited to, lymphocyte and hepatocyte cell lines known in the art.

In an embodiment of the present invention pertains to cells for culturing HCV—said cells may be used in a method for determining the susceptibility of cells in vitro to support HCV infection are human cells comprising the steps of: a)

growing animal cells in vitro; b) transfecting into said cells the nucleic acid according to the present invention and c) determining if said cells show indicia of HCV replication.

Alternatively, primary hepatocytes can be cultured, and then infected with HCV; or, the hepatocyte cultures could be derived from the livers of infected chimpanzees. In addition, various immortalization methods known to those of ordinary skill in the art can be used to obtain cell lines derived from hepatocyte cultures. For example, primary hepatocyte cultures may be fused to a variety of cells to maintain stability.

The present invention further relates to the in vitro and in vivo production of hepatitis C viruses from the nucleic acid sequences of the invention.

An embodiment of the present invention relates to a hepatitis C virus polypeptide produced by a cell transfected with DNA comprising a nucleic acid molecule of the present invention.

Another embodiment of the present invention relates to a hepatitis C virus polypeptide produced by a cell transfected with the RNA transcript of the DNA comprising a nucleic acid molecule of the present invention or the nucleic acid molecule of the present invention.

Yet another embodiment of the present invention relates to a hepatitis C virus produced by a cell transfected with DNA comprising a nucleic acid molecule of the present invention.

An embodiment of the present invention relates to a hepatitis C virus produced by a cell transfected with the RNA transcript of DNA comprising a nucleic acid molecule of the present invention or the nucleic acid molecule of the present invention.

Another embodiment of the present invention relates to a hepatitis C virus whose genome comprises the nucleic acid molecule of the present invention.

An embodiment of the present invention relates to a method for producing a hepatitis C virus comprising transfecting a host cell with the RNA transcript of DNA comprising a nucleic acid molecule of the present invention or the nucleic acid molecule of the present invention, or an RNA transcript of the nucleic acid molecules of the invention.

A further embodiment of the present invention relates to a polypeptide encoded by a nucleic acid sequence of the present invention.

Another embodiment of the present invention relates to a polypeptide encoded by a nucleic acid sequence of the present invention, wherein said polypeptide is selected from the group consisting of Core, E1, E2, p7, NS2, NS3, NS4A, NS4B, NS5A, and NS5B.

Chimeric Nucleic Acid Sequences

Nucleic acid sequences, which comprise sequences from two or more HCV genotypes or subtypes are designated "chimeric nucleic acid sequences". Alternatively, they are designated "intergenotypic recombinants", if the sequences stem from different HCV genotypes or subtypes; and they are designated "intragenotypic recombinants" if the sequences stem from different isolates/strains of the same genotype subtype.

The invention also relates to "chimeric nucleic acid sequences" or "intra- and intergenotypic recombinant nucleic acid sequences", where the chimeric nucleic acid sequences consist of open-reading frame sequences and/or 5' and/or 3' untranslated sequences taken from nucleic acid sequences of hepatitis C viruses of different genotypes or subtypes or isolates In one embodiment, the chimeric nucleic acid sequence consists or is comprised of sequences from the genome of infectious HCV of genotype 3a or 4a which encodes structural polypeptides and sequence from the genome of a HCV of a different genotype or subtype which encodes nonstructural polypeptides.

Alternatively, the nonstructural region of infectious HCV of genotypes 3a and 4a and structural region of a HCV of a different genotype or subtype may be combined. This will result in a chimeric nucleic acid sequence consisting of sequence from the genome of infectious HCV of genotype 3a or 4a, which encodes nonstructural polypeptides and sequence from the genome of a HCV of a another genotype or subtype which encodes structural polypeptides.

Alternatively, only one or several structural or non-structural gene from infectious HCV of genotypes 3a and 4a might be inserted into a genome of another HCV isolate. Also, only one or several structural or non-structural gene from another HCV isolate might be inserted into infectious HCV of genotypes 3a and 4a.

Further, only a certain genomic region, not comprising an entire gene of infectious HCV of genotypes 3a and 4a might be inserted into a genome of another HCV isolate. Also only a certain genomic region, not comprising an entire gene from another HCV isolate might be inserted into infectious HCV of genotypes 3a and 4a.

It is believed that the construction of such chimeric nucleic acid sequences will be of importance in studying the growth and virulence properties of hepatitis C virus and in the production of candidate hepatitis C virus vaccines suitable to confer protection against multiple genotypes of HCV. For example, one might produce a "multivalent" vaccine by putting epitopes from several genotypes or subtypes into one clone. Alternatively one might replace just a single gene from an infectious sequence with the corresponding gene from the genomic sequence of a strain from another genotype or subtype or create a chimeric gene, which contains portions of a gene from two genotypes or subtypes. Examples of genes which could be replaced or which could be made chimeric, include, but are not limited to, the E1, E2 and NS4 genes.

Uses of the Nucleic Acid Sequences, Viruses and Polypeptides of the Invention

The hepatitis C viruses produced from the sequences of the invention may be purified or partially purified from the transfected cells by methods known to those of ordinary skill in the art. In a preferred embodiment, the viruses are partially purified prior to their use as immunogens in the pharmaceutical compositions and vaccines of the present invention.

The present invention therefore relates to the use of the hepatitis C viruses produced from the nucleic acid sequences of the invention as immunogens in killed (e.g., formalin inactivated) vaccines to prevent hepatitis C in a mammal.

In an alternative embodiment, the immunogen of the present invention may be an infectious nucleic acid sequence, a chimeric nucleic acid sequence, or a mutated infectious nucleic acid sequence, which encodes a hepatitis C virus. Where the sequence is a cDNA sequence, the cDNAs and their RNA transcripts may be used to transfect a mammal by direct injection into the liver tissue of the mammal as described in the Examples.

Alternatively, direct gene transfer may be accomplished via administration of a eukaryotic expression vector containing a nucleic acid sequence of the invention.

In yet another embodiment, the immunogen may be a polypeptide encoded by the nucleic acid sequences of the invention. The present invention therefore also relates to polypeptides produced from the nucleic acid sequences of the invention or fragments thereof. In one embodiment, polypeptides of the present invention can be recombinantly produced by synthesis from the nucleic acid sequences of the invention or isolated fragments thereof, and purified, or partially purified, from transfected cells using methods already known in the art. In an alternative embodiment, the polypeptides may be purified or partially purified from viral particles produced via transfection of a host cell with the nucleic acid sequences of the invention. Such polypeptides might, for example, include either capsid or envelope polypeptides prepared from the sequences of the present invention.

When used as immunogens, the nucleic acid sequences of the invention, or the polypeptides or viruses produced therefrom, are preferably partially purified prior to use as immunogens in pharmaceutical compositions and vaccines of the present invention. When used as a vaccine, the sequences and the polypeptide and virus products thereof, can be administered alone or in a suitable diluent, including, but not limited to, water, saline, or some type of buffered medium. The vaccine according to the present invention may be administered to an animal, especially a mammal, and most especially a human, by a variety of routes, including, but not limited to, intradermally, intramuscularly, subcutaneously, or in any combination thereof.

Suitable amounts of material to administer for prophylactic and therapeutic purposes will vary depending on the route selected and the immunogen (nucleic acid, virus, polypeptide) administered. One skilled in the art will appreciate that the amounts to be administered for any particular treatment protocol can be readily determined without undue experimentation. The vaccines of the present invention may be administered once or periodically until a suitable titer of anti-HCV antibodies appear in the blood. For an immunogen consisting of a nucleic acid sequence, a suitable amount of nucleic acid sequence to be used for prophylactic purposes might be expected to fall in the range of from about 100 µg to about 5 mg and most preferably in the range of from about 500 µg to about 2 mg. For a polypeptide, a suitable amount to use for prophylactic purposes is preferably 100 ng to 100 µg, and for a virus $10^2$ to $10^6$ infectious doses. Such administration will, of course, occur prior to any sign of HCV infection.

A vaccine of the present invention may be employed in such forms as capsules, liquid solutions, suspensions or elixirs for oral administration, or sterile liquid forms such as solutions or suspensions. An inert carrier is preferably used, such as saline or phosphate-buffered saline, or any such carrier in which the HCV of the present invention can be suitably suspended. The vaccines may be in the form of single dose preparations or in multi-dose flasks, which can be utilized for mass-vaccination programs of both animals and humans. For purposes of using the vaccines of the present invention reference is made to Remington's Pharmaceutical Sciences, Mack Publishing Co., Easton, Pa., Osol (Ed.) (1980); and New Trends and Developments in Vaccines, Voller et al. (Eds.), University Park Press, Baltimore, Md. (1978), both of which provide much useful information for preparing and using vaccines. Of course, the polypeptides of the present invention, when used as vaccines, can include, as part of the composition or emulsion, a suitable adjuvant, such as alum (or aluminum hydroxide) when humans are to be vaccinated, to further stimulate production of antibodies by immune cells. When nucleic acids, viruses or polypeptides are used for vaccination purposes, other specific adjuvants such as CpG motifs (Krieg, A. K. et al. (1995) and (1996)), may prove useful.

When the nucleic acids, viruses and polypeptides of the present invention are used as vaccines or inocula, they will normally exist as physically discrete units suitable as a unitary dosage for animals, especially mammals, and most especially humans, wherein each unit will contain a predetermined quantity of active material calculated to produce the desired immunogenic effect in association with the required diluent. The dose of said vaccine or inoculum according to the present invention is administered at least once. In order to increase the antibody level, a second or booster dose may be administered at some time after the initial dose. The need for, and timing of, such booster dose will, of course, be determined within the sound judgment of the administrator of such vaccine or inoculum and according to sound principles well known in the art. For example, such booster dose could reasonably be expected to be advantageous at some time between about 2 weeks to about 6 months following the initial vaccination. Subsequent doses may be administered as indicated.

The nucleic acid sequences, viruses and polypeptides of the present invention can also be administered for purposes of therapy, where a mammal, especially a primate, and most especially a human, is already infected, as shown by well-known diagnostic measures. When the nucleic acid sequences, viruses or polypeptides of the present invention are used for such therapeutic purposes, much of the same criteria will apply as when it is used as a vaccine, except that inoculation will occur post-infection. Thus, when the nucleic acid sequences, viruses or polypeptides of the present invention are used as therapeutic agents in the treatment of infection, the therapeutic agent comprises a pharmaceutical composition containing a sufficient amount of said nucleic acid sequences, viruses or polypeptides so as to elicit a therapeutically effective response in the organism to be treated. Of course, the amount of pharmaceutical composition to be administered will, as for vaccines, vary depending on the immunogen contained therein (nucleic acid, polypeptide, virus) and on the route of administration.

The therapeutic agent according to the present invention can thus be administered by subcutaneous, intramuscular or intradermal routes. One skilled in the art will certainly appreciate that the amounts to be administered for any particular treatment protocol can be readily determined without undue experimentation. Of course, the actual amounts will vary depending on the route of administration as well as the sex, age, and clinical status of the subject which, in the case of human patients, is to be determined with the sound judgment of the clinician.

The therapeutic agent of the present invention can be employed in such forms as capsules, liquid solutions, suspensions or elixirs, or sterile liquid forms such as solutions or suspensions. An inert carrier is preferably used, such as saline, phosphate-buffered saline, or any such carrier in which the HCV of the present invention can be suitably suspended. The therapeutic agents may be in the form of single dose preparations or in the multi-dose flasks, which can be utilized for mass-treatment programs of both animals and humans. Of course, when the nucleic acid sequences, viruses or polypeptides of the present invention are used as therapeutic agents they may be administered as a single dose or as a series of doses, depending on the situation as determined by the person conducting the treatment.

The nucleic acids, polypeptides and viruses of the present invention can also be utilized in the production of antibodies against HCV. The term "antibody" is herein used to refer to immunoglobulin molecules and immunologically active portions of immunoglobulin molecules. Examples of antibody molecules are intact immunoglobulin molecules, substantially intact immunoglobulin molecules and portions of an immunoglobulin molecule, including those portions known in the art as Fab, F(ab')$_2$ and F(v) as well as chimeric antibody molecules.

Thus, the polypeptides, viruses and nucleic acid sequences of the present invention can be used in the generation of antibodies that immunoreact (i.e., specific binding between an antigenic determinant-containing molecule and a molecule containing an antibody combining site such as a whole antibody molecule or an active portion thereof) with antigenic determinants on the surface of hepatitis C virus particles.

The present invention therefore also relates to antibodies produced following immunization with the nucleic acid sequences, viruses or polypeptides of the present invention. These antibodies are typically produced by immunizing a mammal with an immunogen or vaccine to induce antibody molecules having immunospecificity for polypeptides or viruses produced in response to infection with the nucleic acid sequences of the present invention. When used in generating such antibodies, the nucleic acid sequences, viruses, or polypeptides of the present invention may be linked to some type of carrier molecule. The resulting antibody molecules are then collected from said mammal. Antibodies produced according to the present invention have the unique advantage of being generated in response to authentic, functional polypeptides produced according to the actual cloned HCV genome.

The antibody molecules of the present invention may be polyclonal or monoclonal. Monoclonal antibodies are readily produced by methods well known in the art. Portions of immunoglobin molecules, such as Fabs, as well as chimeric antibodies, may also be produced by methods well known to those of ordinary skill in the art of generating such antibodies.

The antibodies according to the present invention may also be contained in blood, plasma, serum, hybridoma supernatants, and the like. Alternatively, the antibody of the present invention is isolated to the extent desired by well-known techniques such as, for example, using DEAE Sephadex. The antibodies produced according to the present invention may be further purified so as to obtain specific classes or subclasses of antibody such as IgM, IgG, IgA, and the like. Antibodies of the IgG class are preferred for purposes of passive protection.

The antibodies of the present invention are useful in the prevention and treatment of diseases caused by hepatitis C virus in animals, especially mammals, and most especially humans. Examples for indications of antibody treatment are post-exposure prophylaxis after needle-stick injuries or re-infection prophylaxis after liver transplantation.

An embodiment of the present invention relates to an antibody to the polypeptide encoded by the nucleic acid sequences of the present invention.

An embodiment of the present invention relates to an antibody to the hepatitis C virus produced from the nucleic acid sequences of the present invention.

In providing the antibodies of the present invention to a recipient mammal, preferably a human, the dosage of administered antibodies will vary depending on such factors as the mammal's age, weight, height, sex, general medical condition, previous medical history, and the like.

In general, it will be advantageous to provide the recipient mammal with a dosage of antibodies in the range of from about 1 mg/kg body weight to about 10 mg/kg body weight of the mammal, although a lower or higher dose may be administered if found desirable. Such antibodies will normally be administered by intravenous or intramuscular route as an inoculum. The antibodies of the present invention are intended to be provided to the recipient subject in an amount sufficient to prevent, lessen or attenuate the severity, extent or duration of any existing infection.

The antibodies prepared by use of the nucleic acid sequences, viruses or polypeptides of the present invention are also highly useful for diagnostic purposes. For example, the antibodies can be used as in vitro diagnostic agents to test for the presence of HCV in biological samples taken from animals, especially humans. Such assays include, but are not limited to, radioimmunoassays, EIA, fluorescence, Western blot analysis and ELISAs. In one such embodiment, the biological sample is contacted with antibodies of the present invention and a labeled second antibody is used to detect the presence of HCV to which the antibodies are bound.

Such assays may be, for example, direct where the labeled first antibody is immunoreactive with the antigen, such as, for example, a polypeptide on the surface of the virus; indirect where a labeled second antibody is reactive with the first antibody; a competitive protocol such as would involve the addition of a labeled antigen; or sandwich where both labeled and unlabeled antibody are used, as well as other protocols well known and described in the art.

In one embodiment, an immunoassay method would utilize an antibody specific for HCV envelope determinants and would further comprise the steps of contacting a biological sample with the HCV-specific antibody and then detecting the presence of HCV material in the test sample using one of the types of assay protocols as described above. Polypeptides and antibodies produced according to the present invention may also be supplied in the form of a kit, either present in vials as purified material, or present in compositions and suspended in suitable diluents as previously described.

In a preferred embodiment, such a diagnostic test kit for detection of HCV antigens in a test sample comprises in combination a series of containers, each container a reagent needed for such assay. Thus, one such container would contain a specific amount of HCV-specific antibody as already described, a second container would contain a diluent for suspension of the sample to be tested, a third container would contain a positive control and an additional container would contain a negative control. An additional container could contain a blank.

For all prophylactic, therapeutic and diagnostic uses, the antibodies of the invention and other reagents, plus appropriate devices and accessories, may be provided in the form of a kit so as to facilitate ready availability and ease of use.

The present invention also relates to the use of nucleic acid sequences and polypeptides of the present invention to screen potential antiviral agents for antiviral activity against HCV. Such screening methods are known by those of skill in the art. Generally, the antiviral agents are tested at a variety of concentrations, for their effect on preventing viral replication in cell culture systems, which support viral replication, and then for an inhibition of infectivity or of viral pathogenicity (and a low level of toxicity) in an animal model system.

In one embodiment, animal cells (especially human cells) transfected with the nucleic acid sequences of the invention are cultured in vitro and the cells are treated with a candidate antiviral agent (a chemical, peptide etc.) by adding the candidate agent to the medium. The treated cells are then exposed, possibly under transfecting or fusing conditions known in the art, to the nucleic acid sequences of the present invention. A sufficient period of time would then be allowed to pass for infection to occur, following which the presence or absence of viral replication would be determined versus untreated control cells by methods known to those of ordinary skill in the art. Such methods include, but are not limited to, the detection of viral antigens in the cell, for example, by immunofluorescence procedures well known in the art; the detection of viral polypeptides by Western blotting using antibodies specific therefore; the detection of newly transcribed viral RNA within the cells by PT-PCR; and the detection of the presence of live, infectious virus particles by injection of cell culture medium or cell lysates into healthy, susceptible animals, with subsequent exhibition of the signs and symptoms of HCV infection. A comparison of results obtained for control cells (treated only with nucleic acid sequence) with those obtained for treated cells (nucleic acid sequence and antiviral agent) would indicate, the degree, if any, of antiviral activity of the candidate antiviral agent. Of course, one of ordinary skill in the art would readily understand that such cells can be treated with the candidate antiviral agent either before or after exposure to the nucleic acid sequence of the present invention so as to determine what stage, or stages, of viral infection and replication said agent is effective against.

In an alternative embodiment, viral enzyme such as but not exclusively the NS3 protease, NS2-NS3 autoprotease, NS3 helicase, NS4A (NS3 protease co-factor), NS5A or NS5B RNA polymerase may be produced from a nucleic acid sequence of the invention and used to screen for inhibitors, which may act as antiviral agents. The E1/E2 envelope proteins maybe produced to evaluate the function of entry inhibitors in certain laboratory assays. The structural and nonstructural regions of the HCV genome, including nucleotide and amino acid locations, have been determined.

Such above-mentioned protease inhibitors may take the form of chemical compounds or peptides, which mimic the known cleavage sites of the protease and may be screened using methods known to those of skill in the art. For example, a substrate may be employed which mimics the protease's natural substrate, but which provides a detectable signal (e.g. by fluorimetric or colorimetric methods) when cleaved. This substrate is then incubated with the protease and the candidate protease inhibitor under conditions of suitable pH, temperature etc. to detect protease activity. The proteolytic activities of the protease in the presence or absence of the candidate inhibitor are then determined.

In yet another embodiment, a candidate antiviral agent (such as a protease inhibitor) may be directly assayed in vivo for antiviral activity by administering the candidate antiviral agent to a chimpanzee transfected with a nucleic acid sequence of the invention or infected with a virus of the invention and then measuring viral replication in vivo via methods such as RT-PCR. Of course, the chimpanzee may be treated with the candidate agent either before or after transfection with the infectious nucleic acid sequence or infected with a virus of the invention so as to determine what stage, or stages, of viral infection and replication the agent is effective against.

An embodiment of the present invention relates to a method for assaying candidate antiviral agents for activity against HCV, comprising: exposing a cell containing the hepatitis C virus produced by the nucleic acid sequences of the present invention to the candidate antiviral agent; and measuring the presence or absence of hepatitis C virus replication or correlates thereof in said cell.

An embodiment of the present invention relates to a method for assaying candidate antiviral agents for activity against HCV, comprising: exposing a cell containing the hepatitis C virus produced by the nucleic acid sequences of the present invention to the candidate antiviral agent; and measuring the presence or absence of hepatitis C virus replication or correlates thereof in said cell by at least one of the following: negative strand RT-PCR, quantitative RT-PCR, Western blot, immunofluorescence, non-fluorescent immuno-staining, or infectivity in a susceptible animal.

An embodiment of the present invention relates to an antiviral agent identified as having antiviral activity for HCV by the methods for assaying candidate antiviral agents for activity against HCV.

The invention also provides that the nucleic acid sequences, viruses and polypeptides of the invention may be supplied in the form of a kit, alone or in the form of a pharmaceutical composition.

In one embodiment, said polypeptide or polypeptides are fully or partially purified from hepatitis C virus produced by cells transfected with nucleic acid sequence of the invention.

In another embodiment, the polypeptide or polypeptides are produced recombinantly from a fragment of the nucleic acid sequences of the invention.

In yet another embodiment, the polypeptides are chemically synthesized.

The polypeptides of the invention, especially structural polypeptides, can serve as immunogens in the development of vaccines or as antigens in the development of diagnostic assays for detecting the presence of HCV in biological samples.

The invention therefore also relates to vaccines for use in immunizing mammals especially humans against hepatitis C. In one embodiment, the vaccine comprises one or more polypeptides made from the nucleic acid sequence of the invention or fragment thereof. In a second embodiment, the vaccine comprises a hepatitis C virus produced by transfection of host cells with the nucleic acid sequences of the invention.

The present invention therefore relates to methods for preventing hepatitis C in a mammal.

In one embodiment the method comprises administering to a mammal a polypeptide or polypeptides encoded by the nucleic acid sequence of the invention in an amount effective to induce protective immunity to hepatitis C.

In another embodiment, the method of prevention comprises administering to a mammal a hepatitis C virus of the invention in an amount effective to induce protective immunity against hepatitis C.

In yet another embodiment, the method of protection comprises administering to a mammal the nucleic acid sequence of the invention or a fragment thereof in an amount effective to induce protective immunity against hepatitis C.

The invention also relates to hepatitis C viruses produced by host cells transfected with the nucleic acid sequence of the present invention.

The invention therefore also provides pharmaceutical compositions comprising the nucleic acid sequence of the invention and/or the encoded hepatitis C viruses. The invention further provides pharmaceutical compositions comprising polypeptides encoded by the nucleic acid sequence of the invention or fragments thereof. The pharmaceutical compositions of the invention may be used prophylactic or therapeutically.

An embodiment of the present invention relates to a composition comprising a polypeptide encoded by the nucleic acid sequences of the present invention suspended in a suitable amount of a pharmaceutically acceptable diluent or excipient.

An embodiment of the present invention relates to a composition comprising a nucleic acid molecule of the present invention suspended in a suitable amount of a pharmaceutically acceptable diluent or excipient.

The invention also relates to antibodies to the hepatitis C virus of the invention or their encoded polypeptides and to pharmaceutical compositions comprising these antibodies.

The invention also relates to the use of the nucleic acid sequences of the invention to identify cell lines capable of supporting the replication of HCV in vitro.

The invention further relates to the use of the nucleic acid sequences of the invention or their encoded viral enzymes (e.g. NS3 serine protease, NS3 helicase, NS4A, NS5A, NS5B RNA polymerase) to develop screening assays to identify antiviral agents for HCV.

An embodiment of the present invention relates to a method for assaying candidate antiviral agents for activity against HCV, comprising: exposing an HCV protease encoded by a nucleic acid sequence of the present invention or a fragment thereof to the candidate antiviral agent in the presence of a protease substrate; and measuring the protease activity of said protease.

An embodiment of the present invention relates to a method for assaying candidate antiviral agents for activity against HCV, comprising: exposing an HCV protease encoded by a nucleic acid sequence of the present invention or a fragment thereof to the candidate antiviral agent in the presence of a protease substrate; and measuring the protease activity of said protease, wherein said HCV protease is selected from the group consisting of an NS3 domain protease, an NS3-NS4A fusion polypeptide, or an NS2-NS3 protease.

An embodiment of the present invention relates to an antiviral agent identified as having antiviral activity for HCV by the method assaying candidate antiviral agents for activity against HCV.

All scientific publication and/or patents cited herein are specifically incorporated by reference. The following examples illustrate various aspects of the invention but are in no way intended to limit the scope thereof.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

Figures

FIG. 1

Phylogenetic Tree of pS52, pED43 and Representative HCV cDNA Clones and Isolates of HCV Genotypes 1-4

Genbank accession numbers and names of isolates/clones (in parenthesis) are given. Multiple polyprotein sequence alignment and neighbor-joining tree analysis using amino acid p-distance model were done with Mega4.1. (*) Infectious cDNA clones.

FIG. 2

Course of infection with HCV following intrahepatic transfection of chimpanzees 5276 (FIG. 2A) and 5300 (FIG. 2B) with RNA transcripts of pS52 (genotype 3a) and pED43 (genotype 4a), respectively.

Serum samples collected weekly were tested for HCV-RNA by in-house TAQMAN™ assay (detection limit of 10 IU/ml) and/or by the Roche Monitor Test 2.0 (detection limit of 600 IU/ml): filled rectangle, positive by TAQMAN™ and/or by Monitor; empty rectangle, negative by TAQMAN™. Black dots, HCV Monitor titers—samples below the detection limit are shown as not detected (ND). Anti-HCV antibodies were detected in the 2nd generation ELISA: +, positive; – negative. Shaded area: serum ALT (U/L). Weekly liver biopsies were collected and examined for necro-inflammatory changes: 0, normal; 1, mild; 2, mild-moderate; 3, moderate-severe or 4, severe. The nucleotide sequence of the entire open reading frame of recovered virus genomes in CH5276 (at weeks 7 and 10; open arrows) and CH5300 (at weeks 1 and 6; open arrows) were identical with the sequence of pS52 and pED43, respectively.

Serum Neutralizing antibodies: Percent neutralization of JFH1-based intergenotypic recombinants expressing the S52 (A) or ED43 (B) envelope proteins (>50% considered significant). Percent neutralization of 1:20 serum dilutions was determined by comparison with replicates of weeks −1 and 0, as described in Materials and Methods below. Values represent the mean of three neutralizations; SEM ranged from 3-13% and 1-16% for the S52 (A) and ED43 (B), respectively. Negative values are shown as 0%. We also tested 1:80 serum dilutions; in all cases percent neutralization was<20%.

Peripheral and intrahepatic CD4+/CD8+ T-cell responses: Amount of IFN-γ secreting cells after stimulation with a panel of overlapping peptides, spanning the entire HCV polyprotein, in ELISpot assays. Genotype 3a (strain K3a/650) specific peptides were used for testing of T cells derived from CH5276 (A) and genotype 4a (strain ED43) specific peptides were used for testing of T cells derived from CH5300 (B). PBMC were used directly. Intrahepatic CD4+ and CD8+ T cells were expanded from liver biopsies as described in Materials and Methods. Heights of bars represent the total number of IFN-γ secreting CD4+ and CD8+ T cells following stimulation with the different pools, after background subtraction. The number of IFN-γ secreting cells seen after stimulation with individual peptide pools is colour coded. Cut-off points were determined for individual experiments as described in Materials and Methods. ND, not determinable, visualized by dotted line; results below cut-off are indicated by black bars up to the dotted line.

FIG. 3

Genetic Heterogeneity of S52 Virus Population from Chimpanzee Acute Phase Plasma Pool (1) Nt and aa positions refer to pS52. Number (#) and percentage (%, related to respective genomic region) of positions with genetic heterogeneity (GH) in the analysed clones; clonal analysis was done as described in Materials and Methods. GH≥1 clone and GH≥2 clones; GH at the respective position found in at least 1 or in at least 2 of the analysed clones. Defective genomes were not considered to reflect naturally occurring genetic heterogeneity and are therefore not included; in one of the clones analysed at the respective position nt change G5618A introduced a stop codon and nt insertions at position 6761.1 and 9118.1 caused frame shifts.

FIG. 4

Comparison of ORF Sequence of S52 with that of Other Genotype 3a Isolates (1) Nt and aa positions refer to pS52. Number (#) and percentage (%, related to respective genomic region) of positions with sequence variation between S52 consensus sequence and published sequences with complete ORF of other genotype 3a isolates. At nt 5358, 3/6 S52 clones had

19

T, the other 3 had C, while all other genotype 3a isolates had either T or C. Thus, this position was not considered to be different.

FIG. 5

Genetic Heterogeneity of ED43 Virus Population from Chimpanzee Acute Phase Plasma Pool (1) Nt and aa positions refer to pED43. Number (#) and percentage (%, related to respective genomic region) of positions with genetic heterogeneity (GH) in the analysed clones. GH≥1 clone and GH≥12 clones; GH at the respective position found in at least 1 or in at least 2 of the analysed clones. A stop codon (resulting from nt change at position 1930 in one clone) was not considered to reflect naturally occurring genetic heterogeneity and is not included in this analysis.

FIG. 6

Comparison of ORF Sequence of ED43 Derived from Chimpanzee Plasma Pool with ORF of Other Genotype 4a Isolates (1) Nt and aa positions refer to pED43. Number (#) and percentage (%, related to respective genomic region) of positions with sequence variation between ED43 consensus sequence and published sequences of complete ORF of other genotype 4a isolates. At all positions, at which no distinct nt and/or aa consensus was provided, genetic variation was only assumed, if the provided information clearly showed a difference (e.g. at nt 1966 G and A were found for ED43; thus genetic variation was assumed for another isolate, if T or C was found at the respective position).

FIG. 7

3'UTR Variable Region of pS52 and Other Genotype 3a Isolates

Variable 3' UTR in different pS52 and other genotype isolates; n.a., no isolate name assigned.

FIG. 8

3'UTR Variable Region of pED43 and Other Genotype 4a Isolates

Variable 3' UTR in different pED43 and other genotype isolates; n.a., no isolate name assigned.

EXAMPLES

Materials and Methods

Source of HCV strains S52 and ED43. Genotype 3a strain S52 and genotype 4a strain ED43 were derived from challenge plasma pools from chimpanzees, experimentally infected with serum from chronically infected patients.

Amplification, Cloning and Sequence Analysis

RNA was extracted from 200 ul of the S52 or ED43 plasma pool, respectively, with HIGH PURE VIRAL NUCLEIC ACID KIT (Roche) or TRIZOL™ (Invitrogen). cDNA was synthesized with SUPERSCRIPT™ II or III (Invitrogen) and random hexamers or specific reverse primers (TAG Copenhagen). After treatment of cDNA with RNase H (Invitrogen) and RNase T1 Ambion), PCR was carried out with BD ADVANTAGE 2 POLYMERASE MIX (Clontech); PCR of 3'UTR fragments was carried out with AMPLITAQ GOLD™ DNA polymerase (Applied Biosystems). Gel purified amplicons were A-tailed with TAQ™ DNA polymerase (Invitrogen), cloned in pCR2.1-Topo or pCR-XL-TOPO (Invitrogen) and transformed in TOP10 chemically competent bacteria (Invitrogen). In addition, S52 and ED43 3'UTR amplicons were subcloned after restriction digest. Sequence analysis and determination of consensus sequence was done using SEQUENCHER™ (Gene Codes Corporation) and freeware BioEdit.

20

Polyprotein alignments and phylogenetic analysis was done using MEGA4.1 freeware. HCV sequences used for alignments were from the European HCV database website (euHCVdb and the American HCV database website). Standard molecular techniques, such as restriction digest based cloning and fusion PCR, were used for cloning; all fusion PCR were done with PFU™ DNA polymerase (Stratagene).

Sequences of strain S52 were obtained by analysis of four amplicons: (i) nt 24 to 3396, (ii) nt 3359 to 5186, (iii) nt 5065 to 7596, and (iv) nt 7530 to 9401. These amplicons covered (i) aa 1-1019, (ii) aa 1008-1715, (iii) aa 1576-2419, and (iii) aa 2398-3020 on the polyprotein (nt and aa numbers refer to positions on pS52 with nt 1 being the 1st nt of the 5'UTR and aa 1 being the 1st aa of the polyprotein; they do not include primer sequences). Another amplicon (v) contained the C-terminal NS5B sequence (starting from nt 9339) as well as the 3'UTR variable region, poly-(U/UC) region and the first 16 nt of the conserved X region, and was obtained as previously described; this amplicon covered aa 3001-3021 of the polyprotein sequence. After subcloning, 5 clones of amplicon (i), (ii) and (iv), 6 clones of amplicon (iii), and 15 clones of amplicon (v) were sequenced to determine the consensus sequence. At nt positions 1548 in clone A21 (amplicon i) and 5784 in clone C11 (amplicon iii), the nt was not defined; however, at these positions all other clones analysed had the same nt. pS52 was constructed using clones derived from fragment (i)-(iv), a synthetic 3' UTR sequence (Genscript) and pGEM-9Zf-MOD. pGEM-9Zf-MOD was generated by replacement of the NotI/EcoRI fragment containing the HCV H77 sequence in pCV-H77C (Yanagi 1997) by a convenient multiple cloning site. In pS52, the NotI site is located immediately upstream of the T7 promoter sequence and the C-terminal XbaI site is located immediately upstream of a AscI site.

For ED43, 5'UTR and ORF sequences were obtained by two amplicons: (i) nt 28 to 5631, and (ii) nt 5476 to 9376, which covered (i) aa 1-1763 and (ii) aa 1713-3008 (numbers refer to positions on pED43). Another amplicon (iii), spanning the C-terminal NS5B sequence (starting from nt 9301), the 3'UTR variable region, the poly-(U/UC) region, and the first 16 nt of the conserved X region, was obtained as previously described (Yanagi 1997); this amplicon covered aa 2988-3008. After subcloning, 4 clones of amplicon (i), 5 clones of amplicon (ii), and 10 clones of amplicon (iii) were sequenced to determine the consensus sequence. pED43 was constructed by using clones derived from fragment (i)-(iii) inserted into pCV-H77C (Yanagi 1997) using NotI and NheI sites thereby retaining the 3' terminal sequence from pCV-H77C (Yanagi 1997). Endotoxin free maxipreps (Quiagen) were prepared and the HCV sequence was confirmed for pS52 and pED43.

Sequencing of Cell Culture Derived HCV

The consensus sequence of the entire ORF of S52 or ED43 genomes recovered from serum of infected chimpanzees was determined by direct sequence analysis of PCR amplicons obtained in a nested RT-PCR procedure.

RNA was extracted from serum using the HIGH PURE VIRAL NUCLEIC ACID KIT (Roche) according to manufacturer's protocol. Reverse transcription-polymerase chain reactions (RT-PCR) were carried out using RNA extracted from 100 μL serum. Primers (TAG Copenhagen) were 1.25 μM and dNTPs (Invitrogen) were 0.5 mM in RT reactions. For denaturation, RNA was incubated for 2' at 65° C. together with primer and dNTPs and placed on ice. cDNA syntheses was done in a 20 μL volume with SUPER-SCRIPT™ III (Invitrogen). The final RT reaction was treated with 1-4 U RNase H (Invitrogen) and 1000 U RNase T1 (Ambion) for 20' at 37° C. to degrade RNA. 1st round PCR was performed in a 50 µL volume on 2.5 µL of the cDNA reaction using the ADVANTAGE 2 PCR ENZYME SYSTEM (Clontech). Cycle parameters were 5 cycles of 35" at 99° C., 30" at 67° C. and 10' at 68° C., 10 cycles of 35" at 99° C., 30" at 67° C. and 11' at 68° C., 10 cycles of 35" at 99° C., 30" at 67° C. and 12' at 68° C. and 10 cycles of 35" at 99° C., 30" at 67° C. and 13' at 68° C. Several overlapping ~1 kb products were synthesized in a nested PCR covering the entire ORF. PCR was set up as above using 2.5 µL of the 1st round PCR for each reaction. Initial denaturation was 35 sec at 99° C. followed by 35 cycles with 35 sec at 99° C., 30 sec at 67° C. and 6 min at 68° C.

Sequencing, Sequence Analysis and Databases

All sequence reactions were carried out at Macrogen Inc., Seoul, South Korea. Sequence analysis was carried out with Sequencher 4.7, Gene Codes Corporation and freeware BioEdit v. 7.0.5. HCV sequences used for alignments were retrieved from The European HCV database (euHCVdb; accessible at the http internet site "euhcvdb.ibcp.fr/euH-CVdb/") and the American HCV database (LANL; accessible at the http internet site "hcv.lanl.gov/content/hcv-db/index").

Generation of RNA Transcripts and Transfections

Plasmid DNA was linearized with XbaI (New England BioLabs) and purified (WIZARD™ SV Gel and PCR Clean-Up System; Promega). 5 µg linearized DNA was in vitro transcribed with T7 RNA Polymerase for 2 hrs in a final volume of 100 µl, following manufacturer's instructions (Promega). Before generation of RNA transcripts to be used for in vitro transfection, XbaI digested pED43 with and without adaptive mutations was in addition treated with Mung bean nuclease. The amount of RNA transcripts was estimated by standard agarose gel electrophoresis.

For in vitro transfections, Huh7.5 cells were plated at $4 \times 10^5$ per well of a 6-well plate in Dulbecco's modified Eagle medium with 4500 mg/L glucose, GlutaMAX-I™, and Pyruvate (Gibco/Invitrogen Corporation) containing 10% heat-inactivated fetal bovine serum (Sigma), penicillin 100 U/mL and streptomycin 100 µg/mL (Gibco/Invitrogen Corporation), at 5% CO2 and 37° C. After 12-24 hrs, cells were incubated with lipofection complexes (RNA transcripts and 5 µL LIPOFECTAMINE™ 2000 [Invitrogen] (a cationic liposome transfection reagent) in serum-free medium (Opti-MEM; Invitrogen) for approximately 16 hrs.

For in vivo transfections, chimpanzees were housed in compliance with relevant guidelines and requirements, in facilities fully accredited by the Association for Assessment and Accreditation of Laboratory Animal Care International. CH5276 and CH5300 were inoculated intrahepatically by a percutaneous procedure by RNA transcribed as described above from a total of 20 µg XbaI digested and purified pS52 and pED43, respectively.

Monitoring of HCV Infection in Huh7.5 Cells

Huh7.5 cells were immunostained for HCV Core antigen using the primary antibody mouse anti-HCV core protein monoclonal antibody (B2) (Anogen, Yes Biotech Laboratories) at 1:200 in PBS with 5% bovine serum albumin, and the secondary antibody ALEXA FLUOR™ 594 goat anti-mouse IgG (H_L) (Invitrogen) at 1:500 in PBS/TWEEN™ (Polysorbate 20); cell nuclei were counterstained with HOECHST™ 33342 (Invitrogen). The presence of HCV-positive cells was evaluated by fluorescence confocal microscopy. Staining was visualized using a LEICA™ TCS confocal microscope. Mouse anti-HCV core protein monoclonal antibody (B2) was shown to readily recognize S52 and ED43 Core proteins.

Monitoring of HCV Infection in Chimpanzees

Pre-infection sera were obtained at weeks 0, −1, −5 and −39 for CH5276 and at weeks 0, −1, −5 and −16 for CH5300; pre-infection liver biopsies were obtained at weeks −1 and −5 for both animals. For CH5276, serum and liver biopsies were collected weekly during weeks 1-32. For CH5300, serum and liver biopsies were taken weekly during weeks 1-18, and every two weeks during weeks 20-32. Thereafter, both animals were followed monthly until week 54 to determine the final outcome of infection. Serum samples were tested for HCV RNA (In House TAQMAN™ 14 and Monitor 2.0; Roche Diagnostics), HCV antibodies (ELISA 2.0; Abbott,), and alanine aminotransferase (ALT) (Anilytics). Liver biopsy samples were examined for necro-inflammatory changes.

Investigation of Chimpanzee Neutralizing Serum Antibodies

Neutralization assays are known in the art. Briefly, heat-inactivated CH5276 sera were pre-incubated with ~20 focus forming units (FFU) S52/JFH1I793S,K1404Q (Gottwein 2007) and CH5300 sera were pre-incubated with ~45 FFU ED43/JFH1T827A,T977S (Scheel 2008) for 1 hour at 37° C., followed by 3 hours incubation on 6000 Huh7.5 cells. After 48 hours incubation, cultures were immunostained for HCV NS5A with primary antibody 9E10 (gift from C.Rice), used at 1:1000 in PBS/0.1% TWEEN™-20 (Polysorbate 20)over night at 4° C. After washing, a 1:300 dilution of 2° Ab HRP-goat anti-mouse IgG (H+L) (Amersham Biosciences) in PBS/0.1% TWEEN™-20 (Polysorbate 20) was added and incubated for 30' at room temperature. Staining was developed using DAB (diaminobenzidine) substrate kit (DAKO) for 30' after washing. The number of focus forming units (FFU; cluster of infected cells, separated from adjacent clusters of infected cells by at least 2 uninfected cells) was determined on an IMMUNOSPOT™ Series 5 UV Analyzer (CTL Europe GmbH) with customized software kindly provided by Alexey Karulin and Paul Lehmann. From FFU counts in experimental wells, the mean of spot counts of 24 negative control wells was subtracted (~5 spots for the genotype 3 and 4 neutralization experiments). Count numbers were comparable to manual counting, and in general counts of up to 200 FFU/well were considered reliable, because they were in the linear range of dilution series, carried out in an establishment phase. For CH5276, FFU counts ranged from 26 to 73 FFU/well; for CH5300 counts ranged from 59-146 FFU/well. Percentages of neutralization were obtained by comparison with the mean of FFU counts from all wells, in which the respective virus had been pre-incubated with serum samples from week −1 or from week 0.

Investigation of Chimpanzee Cellular Immune Responses

CD4+/CD8+ T cells were isolated from peripheral blood and from the liver. T cells from liver were expanded in vitro before further analysis. Number of interferon-gamma (IFN-γ) secreting T cells was evaluated in ELISpot (U-Cytech) assays after stimulation with HCV peptides. Synthetic peptides, specific for genotype 3a (strain K3a/650) and 4a (strain ED43), that were approximately 20 aa in length, overlapping by 10 residues, and spanning the entire HCV polyprotein were used. These peptides were assembled in 9 pools and used for stimulation.

Example 1

Genetic Analysis of Genotype 3a Strain S52

The HCV source was from an acute-phase challenge plasma pool from a chimpanzee, experimentally infected with serum from a chronically infected Italian patient. In this pool, the HCV RNA titer was $10^{4.3}$ IU/ml and the infectious titer was $10^3$ chimpanzee infectious doses (CID)/ml.

The S52 consensus sequence was determined by clonal sequence analysis of five overlapping RT-PCR amplicons, spanning the complete ORF and partial UTRs as described in Material and Methods. At each nt position, 5-11 clones were analysed. In the 5' UTR sequence of S52, spanning nt 24-339 (all nt positions refer to final pS52 sequence), genetic heterogeneity among the analysed clones was found at 3 nt positions (with 1 clone being different from the other 4 at each position) (FIG. 3).

The S52 ORF consisted of 9063 nt (nt 340-9402), encoding a 3021 aa polyprotein, followed by a single stop codon (nt 9403-9405). Genetic heterogeneity, with at least one of the analysed clones being different from the S52 consensus sequence, was found at 199 nt positions (2.2%) and 67 aa positions (2.2%) (FIG. 3). At 63 nt (0.7%) and 23 aa (0.8%) positions, at least two clones, covering the respective position, deviated from the S52 consensus sequence.

Compared to the entire polyprotein, a high percentage of aa positions with genetic heterogeneity was found in E1, E2, p7, NS2 and NS5A (FIG. 3). The amino acid sequence of E2 HVR1 was identical between the clones. Amino acid positions with genetic heterogeneity are summarized in Table 1. There was evidence of 2 different S52 quasispecies populations (Table 1). For each sequenced clone, differences to the consensus sequence were found in average at 0.48% of positions at the nucleotide level, and 0.54% of positions at the amino acid level. A defective ORF was found in 3 clones (FIG. 3, Table 1). At nt position 5358, no distinct nt consensus could be determined, since 3 of 6 clones had T, the other 3 had C, with T and C encoding the same aa.

The length of S52 3'UTR variable region was difficult to define. Even though there was a consensus ACACUCC motif (nt 9418-9424), as described for other isolates 33, a UG dinucleotide, typically preceding the start of the poly (U/UC region) was only found in 1/15 clones analysed. The first 23 nt of the variable region (nt 9403-9425) were identical in the 15 clones. They were followed by a UUC motif (nt 9426-9428), present in 13/15 clones (a comparison of the pS52 3'UTR variable region to other 3a sequences is shown in FIG. 7). Assuming a variable region of 26 nt (nt 9403-9428), the length of the poly(U/UC) region, which could be determined in 3/15 clones, was 108, 111, and 123 nt, respectively. The first 16nt of the 3'UTR X region were identical in all analysed clones.

Compared to 2 other genotype 3a 5'UTR sequences (genbank accession numbers D17763 and D28917; in the following sections, HCV isolates will be identified by their accession numbers), the obtained S52 consensus sequence showed differences at 1 and 3 nt positions, respectively. In comparison to the partial 5'UTR and complete Core/E1 sequence (nt 58-1488) obtained from the source patient, the S52 consensus sequence obtained in this study differed at 1 nt/aa position in E1. The S52 consensus ORF differed from 3 published genotype 3a isolates with reported ORF in 4.8-6.5% of positions at the nt level and in 3.6-5.9% of positions at the aa level (FIG. 4). A phylogenetic analysis of the polyprotein of developed HCV cDNA clones and representative HCV isolates showed that pS52 clustered with other genotype 3a isolates (FIG. 1).

Comparing genotype 3a 3'UTR variable regions, the consensus sequence of the first 23nt of the S52 3'UTR (nt 9403-9425) was identical to the equivalent sequence of two other genotype 3a isolates with genebank accession numbers ID28917 71 and AF009075, but differed at 1 nt from D17763, and at 3 nt from D85024 and D85025. The consensus UUC (nt 9435-9428), occurring in S52, was also present in D28917; in the other isolates it was replaced by either UUUC or AUUC. The length of the 3'UTR variable region of other genotype 3a isolates was previously defined to be 28-35 nt, determined by a UG motif not occurring for S52 (FIG. 7). Length of the 3'UTR poly(U/UC) tract was 110 nt for AF009075 33, and 84 and 86 nt for D85024 and D8502572, respectively. S52 consensus of the first 16 nt of the 3'UTR X region was identical to genotype 3a isolates AF009075, D85024 and, D85025 and genotype 1a cDNA clone pCV-H77C (AF011751) (Yanagi 1997).

Example 2

Generation of Consensus Clone pS52

The consensus full-length cDNA clone pS52 was constructed in vector pGEM-9Zf as described in Material and Methods. The S52 sequence contained the following structural elements: (I) 5'UTR of 339nt, in which nt 24-339 were the S52 consensus sequence, while nt 1-23 were deduced from published genotype 3a 5' UTR sequences (D28917, D17763). For nt 1, at which G (D28917) and A (D17763) occurred, G was chosen to facilitate in vitro transcription. (II) ORF of 9063 nt (nt 340-9402) with two coding nt changes, G1037A and G1913A, in comparison to the S52 consensus sequence. However, at both positions, A encoded by pS52 was present in 2/5 clones analysed. In addition, in 10 clones of a Core-E2 amplicons generated previously, A was present at position 1037 in 8 clones and at position 1913 in 6 clones. Non-coding nt changes compared to the S52 consensus sequence were A639G, A915T, C1488T, G1575A, C1707T, C2655T, C2805T, C3069T, G3792A, T5187C, T7755A, T8469C, G8745A. Non-coding nt changes A915T and T7755A were inserted to remove consensus XbaI sites, at both positions being present in 5/5 clones analysed. All other non-coding nt changes in pS52 were occurring in at least 1 of the 5 to 6 clones covering the respective position. At position 5358, at which no definite nt consensus was determined, T was introduced in pS52. (III) 3' UTR of 235nt (nt 9403-9637) with a variable region of 26nt (nt 9403-9428), identical to the S52 nt consensus sequence; with a poly(U/UC) region of 111 nt (nt 9429-9539), chosen from one of the 3 clones, in which this region could be entirely sequenced; and with a conserved X region of 98nt (nt 9540-9637), determined by the pCV-H77C (Yanagi 1997) sequence. The X region from 2 genotype 3a isolates (D85024, D85025) was identical to the pCV-H77C X region, whereas genotype 3a isolate AF009075 differed at nt position 9594 and 9635. An XbaI-site was inserted immediately downstream of the HCV 3'UTR, for generation of the exact HCV 3'end.

Example 3

Genetic Analysis of Genotype 4a Strain ED43

The HCV source was an acute-phase challenge plasma pool from a chimpanzee, experimentally infected with serum from a chronically infected Egyptian patient. This plasma pool had an HCV RNA titer of $10^{5.5}$ IU/ml and an infectivity titer of $10^5$ CID/ml. Previously, the complete ORF of the source patient's virus has been sequenced. Furthermore, the complete 3'UTR of the patient's virus has been sequenced previously.

In the present study, ED43 consensus sequence from the chimpanzee plasma pool was determined by clonal sequence analysis of three overlapping RT-PCR amplicons spanning the complete ORF, and partial UTRs as described in Material and Methods. In ED43 5'UTR sequences, from nt 28 to nt 340 (nt positions refer to pED43), genetic heterogeneity among 4 clones was found at 6 nt positions (with one clone differing from the other clones at each position) (FIG. 5).

In agreement with the patient's virus sequence 9, ED43 ORF was found to consist of 9024 nt (nt 341-9364), coding for 3008 aa, and terminated by two stop codons (nt 9365-9367 and 9374-9376). Genetic heterogeneity, with at least one of the analysed clones deviating from the ED43 consensus sequence, was found at 144 nt positions (1.6%) and 64 aa positions (2.1%) (FIG. 5). Genetic heterogeneity with at least two clones deviating from the consensus sequence was found at only 3 nt and none of the aa positions.

Compared to the average for the entire polyprotein, on the aa level genetic heterogeneity was relatively high in Core, E1, p7, NS2, NS3, and NS4A. The nt and aa sequence of HVR1 was identical between the clones. AA positions at which individual clones differed from the ED43 consensus sequence are shown in Table 2. For each sequenced clone, quasispecies were found in average at 0.35% at the nt level, and 0.45% at the aa level compared to the consensus sequence. One defective genome was identified (FIG. 5). No distinct consensus could be determined at nt positions 1966 (G/A), 1999 (C/T), 3751 (A/G), and 3871 (C/T) where 2 clones had one nt and 2 clones another nt; these nt changes were all non-coding.

ED43 3'UTR variable region of 36nt (nt 9365-9400) was identical in the 10 clones analysed; it was terminated by a UG dinucleotide as described for other isolates. The exact length of the poly(U/UC) region could be determined in all 10 clones and ranged from 72-86 nt. The first 16nt of the 3'UTR X region were identical in all clones analysed. The obtained ED43 5'UTR consensus sequence differed from a published genotype 4a 5'UTR sequence (D45193) at 1 nt position. For ED43 derived from the infected patient (Y11604) 9, nt 62-340 of the 5'UTR were determined; this sequence differed from ED43 consensus sequence derived from the chimpanzee plasma pool at 2 nt positions. ED43 consensus ORF sequence, determined in the present study, differed at 125 nt positions (1.4%) and 67 aa positions (2.2%) from Y11604 ORF (FIG. 6).

Differences of at least 2.2% on the aa level were detected in NS2, NS4B, NS5A, and NS5B. Differences of less than 1% were detected in E1 and E2, notably the HVR1 sequence of both isolates was identical at the nt and aa level. At aa 2011 of the ED43 polyprotein, C was found as previously described; C39 in NS5A was described to be critical for replication 62. In contrast, in the infected patient W was reported to be present at this position 9. From 7 other genotype 4a isolates with reported ORF consensus sequence, ED43 consensus sequence differed in 8.8-9.5% at the nt level and at 5.4-6.7% at the aa level (FIG. 6).

Phylogenetic analysis showed that ED43 consensus sequence determined in this study clustering with other genotype 4a isolate sequences, however forming a distinct group with Y11604 (FIG. 1). The 3'UTR variable region of ED43 consensus sequence determined in the present study was identical to the equivalent sequence of the source patient determined previously and differed at 1 nt from the equivalent sequence of Y11604. Also, high homology was found between 3'UTR variable region of ED43 and that of several other genotype 4a isolates (FIG. 8). AF009077 had a poly(U/UC) region of 46nt. The consensus sequence of the first 16nt of the ED43 X region (nt 9482 to 9497) was identical to the equivalent sequence of AF00907733 and pCV-H77C (Yanagi 1997).

Example 4

Generation of Consensus Clone pED43

The consensus full-length cDNA clone pED43 was constructed in pGEM-9Zf with the following structural elements: (I) 5'UTR of 340nt with nt 28-340 being the ED43 nt consensus sequence, while nt 1-27 were derived from D45193. (II) ORF of 9024nt (nt 341-9364), encoding the ED43 aa consensus sequence. Compared to the ED43 nt consensus sequence, non coding changes are A2458G, A2593G, C3988T, A4459C, C4915T and T5428C; each of these nt changes was present in 1/4 clones analysed. For determination of pED43 nt sequence at nt 1966 and nt 1999, at which no distinct nt consensus was obtained, we used information from 7 clonal sequences previously obtained for this region.

Thus, in pED43 at nt1966, G was chosen, because it was seen in 6/7 of these clones. At nt 1999, C was chosen, seen in 5/7 of these clones. At the other two nt positions without distinct consensus, A was chosen at nt 3751 and C was chosen at nt 3871 in pED43. (III) 3' UTR of 215nt (nt 9365-9579) with a variable region of 36 nt (nt 9365-9400) identical to the ED43 nt consensus sequence; with a poly (U/UC) region of 81 nt (nt 9401-9481), chosen from one of the 10 clones analysed; with a conserved X region of 98 nt (nt 9482-9579) determined by the sequence of pCV-H77C (Yanagi 1997), differing at nt position 9556 from X region of the source patient AF009077. An XbaI-site was introduced immediately downstream of the HCV 3'UTR.

Example 5

RNA Transcripts from pS52 and pED43 do Not Lead to Infection of Huh7.5 Hepatoma Cells Because Huh7.5 cells were shown to be permissive to infection with strain JFH1 and JFH1-based intra- and intergenotypic recombinants including recombinants with Core-NS2 sequence of S52 and ED43, the present inventors tested whether full-length S52 and ED43 RNA transcripts led to productive infection of transfected Huh7.5 cultures.

Thus, replicate cultures were transfected with RNA transcripts from p552, pED43, and positive control p36/JFH1. For J6/JFH1, HCV-Core antigen positive cells were detectable 48 hrs post transfection and viral spread to almost the complete Huh7.5 culture occurred in 4-10 days. In contrast, there were no HCV-Core positive cells detected in cultures transfected with RNA transcripts of pS52 and pED43; these cultures were stained 2 to 3 times per week and followed for 4 weeks. In total four independent transfections with RNA transcripts from pS52; and two transfections with pED43 transcripts were analyzed.

The present inventors further tested whether selected adaptive mutations, leading to efficient growth of intergenotypic recombinants S52/JFH1 (Gottwein 2007) and H77/JFH1 (Yi 2007) as well as JFH1 (Kaul 2007) in hepatoma cell lines, could confer replication capability to the full-length S52. Therefore, we constructed pS52 with single nt exchanges in p7: T2717G (identified in S52/JFH1), in NS3: A4549C (identified in S52/JFH1) or A4097T (identified in H77/JFH1), and in NS5A: G7171C (identified in S52/JFH1) or G7621C (Identified in JFH1) (nt positions refer to pS52). Similarly, the present inventors introduced two coding NS2 mutations (A2819G and A3269T), shown to confer cell culture viability to ED43/JFH1 (Scheel 2008), in pED43. However, after transfection of Huh7.5 cells with the respective RNA transcripts, no HCV-Core positive cells were observed; the ED43 (A2819G and A3269T) culture was followed for 1 week, all other cultures were followed for 4 weeks. Thus, cDNA clones pS52 and pED43, with or without putative adaptive mutations, were apparently not replication competent in Huh7.5 cells, and long-term cultures did not lead to adaptation that yielded infectious particles.

Example 6

RNA Transcripts from pS52 are Infectious in Vivo

Figure 2A:
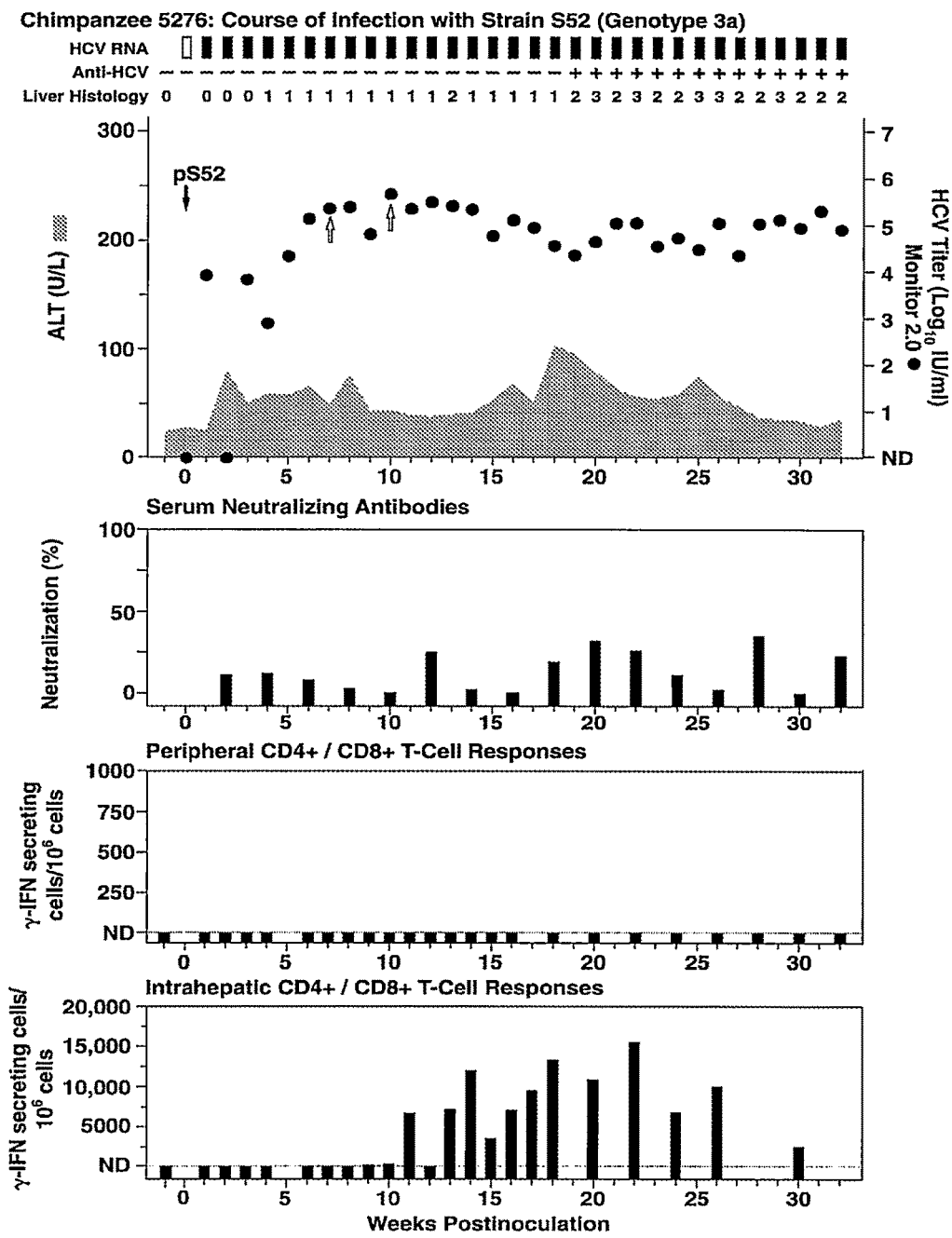
FIG. 2A and FIG. 2B
Course of infection with HCV following intrahepatic transfection of chimpanzees 5276 (FIG. 2A) and 5300 (FIG. 2B) with RNA transcripts of pS52 (genotype 3a) and pED43 (genotype 4a).

After intrahepatic transfection of pS52 in vitro RNA transcripts, CH5276 became viremic at week 1 and peak HCV RNA titers of $10^5$-$10^{5.5}$ IU/ml were reached during weeks 6-14 post transfection (FIG. 2A). The ORF sequence of viral genomes recovered at peak HCV titers from serum taken at weeks 7 and 10, respectively, was identical to the sequence of pS52. The animal became anti-HCV positive in a commercial test from week 19 post-infection. However, CH5276 did not develop significant levels of autologous neutralizing antibodies, since pre-incubation of S52/JFH1 viral particles with 1:20 and 1:80 dilutions of week 2 to 32 sera did not lead to >50% of neutralization of S52/JFH1 infectivity in Huh7.5 cells compared to pre-incubation with pre-infection sera (FIG. 2A). CH5276 eventually developed acute hepatitis with elevated serum ALT levels. High ALT levels of ~100 IU/ml coincided with significant necro-inflammatory liver changes, detected during weeks 19-32. CH5276 became persistently infected with viremia (~$10^5$ IU/ml) at the end of follow-up at week 54. Thus, the constructed S52 consensus sequence was fully functional in vivo.

To further examine the pathogenesis of HCV infection, the present inventors monitored occurrence of HCV specific IFN-γ secreting CD4+/CD8+ T cells in peripheral blood and liver biopsy samples (FIG. 2A). CH5276 peripheral mononuclear cells (PBMC) did not show any IFN-γ secretion above background in ELISpot assays, when stimulated with HCV genotype 3a peptide pools. Intrahepatic IFN-γ secreting CD4+/CD8+ T cells were studied similarly after in vitro expansion and were first detected at week 9 (FIG. 2A). An increase in the percentage of IFN-γ secreting intrahepatic T cells during weeks 11-32 was detected several weeks before occurrence of peak ALT levels and also preceded the most pronounced necro-inflammatory histologic liver changes (observed during weeks 19-32).

Example 7

RNA Transcripts from pED43 are Infectious in Vivo

Figure 2B:
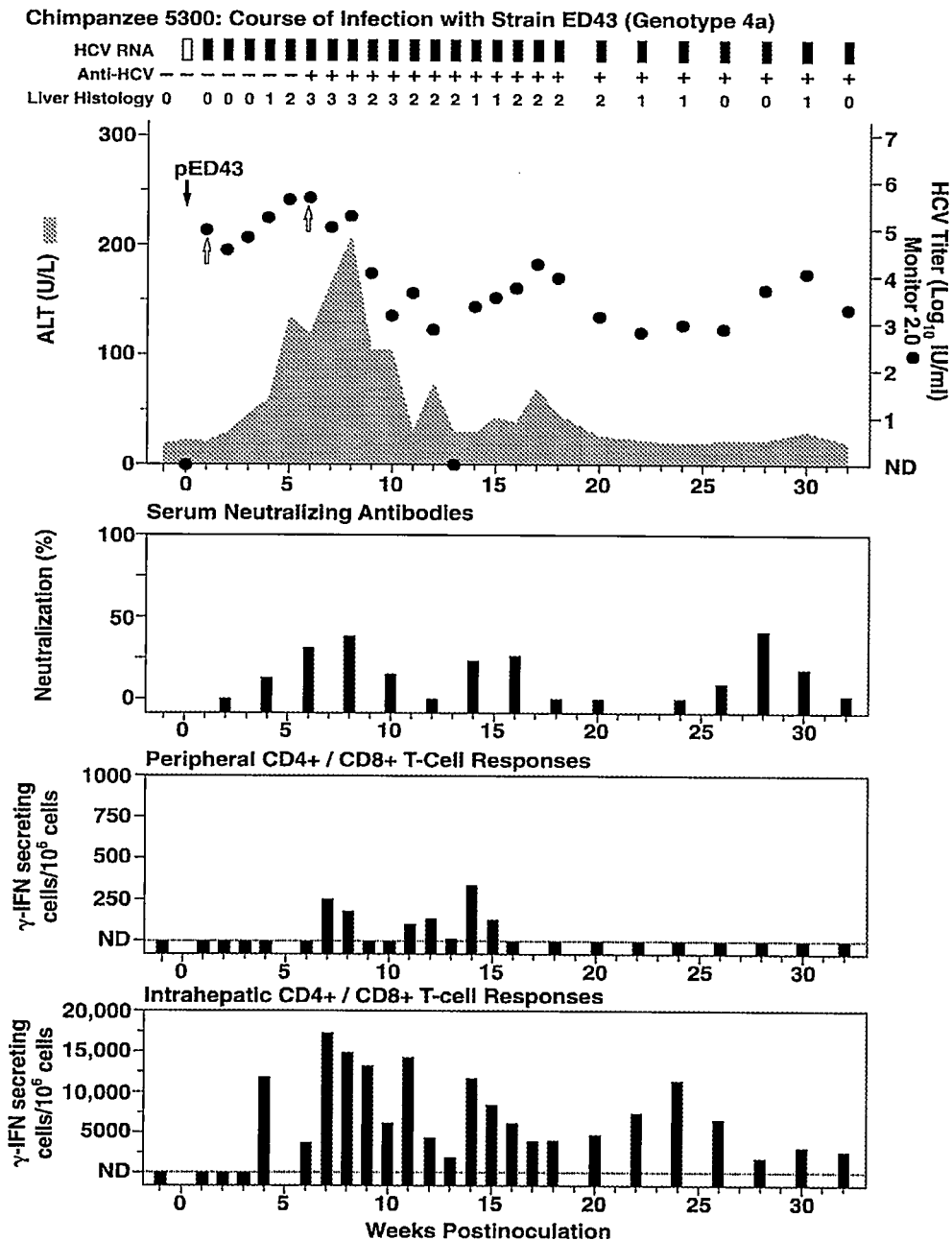

Immediately after intrahepatic transfection of CH5300 with pED43 in vitro transcripts, the HCV RNA titers increased to peak levels of $10^{4.5}$-$10^{5.5}$ IU/ml during weeks 1-8 post transfection (FIG. 2B). The ORF sequence of viral genomes recovered from week 1 and 6 serum did not show any changes compared to the pED43 sequence. CH5300 sero-converted in a commercial test at week 6. However, CH5300 did not develop significant levels of autologous neutralizing antibodies (FIG. 2B). In CH5300, the course of infection was characterized by a fast onset of acute hepatitis with peak serum ALT levels between 100 and 200 IU/ml during weeks 5-10. Peak ALT levels coincided with detection of significant necro-inflammatory liver changes during weeks 5-13. Following week 10, ALT decreased to 20 to 70 IU/ml, followed by decrease of liver necro-inflammatory changes. Between week 9 and 54, RNA titers decreased to levels of $10^{2.5}$-$10^4$ IU/ml. CH5300 was persistently infected with viremia ($10^3$-$10^4$ IU/ml) at the end of follow-up at week 54. In conclusion, the constructed ED43 consensus sequence was fully functional in vivo. Intrahepatic CD4+/CD8+ T cells, secreting IFN-γ upon stimulation with HCV genotype 4a peptide pools, were first detected at week 4 post transfection, coinciding with evidence of acute hepatitis. In CH5300, HCV genotype 4a reactive PBMC were detected at time-points, at which strong intrahepatic T cell responses were observed (FIG. 2B).

Discussion

In this study, the present inventors generated and characterized infectious cDNA clones of important genotypes 3a (pS52) and 4a (pED43). Compared to previously developed cDNA clones of genotypes 1a, 1b and 2a as well as consensus sequences of selected isolates of various genotypes and subtypes, pS52 sequence formed a distinct cluster with previously published genotype 3a isolate sequences, while pED43 sequence clustered with described genotype 4a isolate sequences (FIG. 1). Variation between polyprotein consensus sequence of S52, which originated for Sardinia, Italy, and 3a isolates from New Zealand (NLZ1), Switzerland (452) and Japan (K3a/650) was 3.6-5.9% on the aa level (FIG. 4). Greater variation was observed between sequences of ED43, which originated from Egypt, and several 4a isolates from the Boston area as well as one isolate from Spain (5.4-6.7% on aa level) (FIG. 6). In contrast, ED43 was more similar to genotype 4a isolates obtained from other Egyptian patients. A high degree of variation between S52 and other genotype 3a isolates as well as between ED43 and other genotype 4a isolates was found in genome regions, for which in general a great diversity was described, such as E1, E2 (especially HVR1), p7, NS2, and NS5A (FIGS. 4 and 6).

In contrast, relatively great variation between pED43 and Y11604, which differed in 2.2% of their polyprotein sequence, was also found in NS4B and NS5B, while E1 and E2 were relatively similar (FIG. 6). Interestingly, for ED43 and Y11604, E2 HVR1 was identical on the nt and aa level. ED43 had as Y11604 and other genotype 4a isolates a 4 aa deletion in the interferon sensitivity determining region (ISDR; aa 2210-2245); ED43 and Y11604 ISDR differed at 4 aa (11%) at the N-terminus of this region. Studies of the impact of sequence variations in ISDR on IFN sensitivity will be facilitated by replicon/cell culture systems with genotype specific NS5A (ISDR).

To determine the S52 and ED43 consensus sequence, the inventors studied the quasispecies distribution in standardized acute phase plasma pools. Overall, relatively high genetic heterogeneity was found in genome regions with high genetic diversity such as E1, E2, p7 and NS2 (FIG. 3, 5). In addition, relative high heterogeneity was found in ED43 Core and NS3, two proteins, which in general show less genetic diversity. Another exemption was E2 HVR1, which was identical in all S52 and in all ED43 clones analysed. Genetic heterogeneity in the S52 plasma pool was greater than in the ED43 plasma pool (FIGS. 3 and 5), partly due to occurrence of 2 different quasispecies subpopulations in this pool (Table 1). Different quasispecies subpopulations were previously found in plasma pools of J6 and J4. pED43 cDNA clone reflected the aa consensus sequence, while pS52 had two non consensus aa residues, which were, however, naturally occurring in the S52 pool. As described previously, in pS52 and pED43, the conserved 3'X region was derived from pCV-H77C (Yanagi 1997) but showed close homology to X regions published for other genotype 3a and 4a isolates.

As other previously developed cDNA clones, pS52 and pED43 were not viable in cell culture. Cell culture adaptive mutations identified in JFH1 and JFH1-based intergenotypic recombinants did not lead to cell culture adaptation of pS52 and pED43. The adaptive mechanism of such mutations is not known. They might mediate interaction of HCV proteins derived from different genotypes, however, they might also adapt the respective protein to cell culture, e.g. by facilitation of interaction with cellular binding partners. Proof of functionality of pS52 and pED43 implies proof of functionality of the individual proteins. This knowledge will further development of intergenotypic recombinant cell culture systems containing yet undefined, minimal JFH1 elements, critical for cell culture viability. Transfection of CH5276 and CH5300 with RNA transcripts of pS52 and pED43 led to robust infection. A course of acute HCV infection, comparable to infection with S52 and ED43, was observed in chimpanzees, which were infected by inoculation with viral particles or intrahepatic transfection with RNA transcripts from various cDNA clones. Even though both animals became persistently infected, significant differences were observed regarding the course of viremia, serum ALT, and cellular immune responses. As previously described for H77 infected chimpanzees, in CH5300 the initial increase in viral RNA (week 1-6) showed a biphasic pattern with a primary rapid and secondary slower slope, separated by a transient decline (week 2) (FIG. 2B).

This decrease in viral replication was suggested to result from activation of innate antiviral defence mechanisms and especially the type-I IFN system, because no intrahepatic HCV reactive T cells but elevated intrahepatic 2'5' oligoadenylate synthetase 1 mRNA levels were found during the first weeks of HCV infection. Interestingly, for CH5276 the decline in HCV RNA observed at week 2 was far more pronounced and the following increase in HCV RNA more delayed than in CH5300 and acutely infected chimpanzees previously studied (FIG. 2A). In patients, HCV is highly sensitive to treatment with IFN-γ during the acute phase of infection, and in chronically infected individuals genotype 3a is more sensitive to interferon treatment than genotype 1 and 4. Thus, genotype 3a might also be more sensitive to endogenous IFN production during the acute phase of infection. In line with this, higher spontaneous clearance rates have been reported for genotype 3a in one but not other studies. However, even though genotype 2a is supposed to have a relatively great sensitivity to IFN, after transfection of a chimpanzee with RNA transcripts from a genotype 2a cDNA clone, the decline in RNA titers was not as pronounced as for S52. In order to draw conclusions about dependence of early HCV infection kinetics on genotype, more studies with different isolates including monitoring of correlates of innate immunity and other host factors are of importance. During the further course of acute HCV infection different patterns of viremia were observed in various studies. In 5300, a plateau with peak HCV RNA titers (week 5 and 6) was followed by a rapid 2 log decrease of HCV RNA, associated with liver damage most likely mediated by onset of the adaptive immune response (FIG. 2B). This pattern is typically observed in animals that clear HCV but also in some animals that subsequently develop persistent infection; it has not been clarified which immunological and/or viral features are decisive for differential outcomes. In other animals with persistent infection, as observed for CH5276, HCV RNA is consistently detected in serum during the acute phase of infection.

Early, strong, multispecific and sustained CD4+ and CD8+ T cell responses have been associated with viral clearance in humans and chimpanzees. In chimpanzees, occurrence of intrahepatic HCV reactive IFN-γ secreting CD4+ and CD8+ T cells correlated with ALT increase and with at least temporary resolution of viremia. Also occurrence of HCV reactive PBMC, usually present at low frequency, was associated with viral clearance. In general, T cell responses to HCV are delayed; even during a successful adaptive immune response, they occur first after 4-8 weeks post infection. Also, it is frequently seen during HCV infection, that primarily successful looking immune responses, leading to primary control of viremia, all the sudden fail to control infection and viremia rebounds; this might be due to viral escape mechanisms. In both chimpanzees, CH5300, infected with genotype 4a and in CH5276, infected with genotype 3a, we observed intrahepatic T cell responses. In CH5300, T cells occurred early during infection, whereas intrahepatic T cells occurred late in infection in CH5276. In addition, in CH5300, HCV reactive PBMC were present, whereas these were absent in CH5276. Thus, the immune response observed in CH5300 reflected much more a response thought to be efficient against HCV than the immune response seen in CH5276. In line with this, transient decline in viremia was observed for CH5300. In conclusion, infection with S52 and ED43 both triggered an immune response as typically seen in HCV infected chimpanzees and humans underlining the full functionality of the developed cDNA clones pS52 and pED43. Sequence analysis of viral genomes aimed at demonstrating functionality of the constructed sequences. At the chosen time-points, before onset of adaptive immune responses, S52 and ED43 were genetically stable, indicating full functionality of the developed sequences. This is in contrast to JFH1, which had acquired adaptive mutations already two weeks post transfection.

CH5300 and CH5276 did not develop neutralizing antibodies (ntAB). While ntAB are commonly found in the chronic phase of infection, they are frequently absent during the acute phase. Even though in patients occurrence of nt AB in the acute phase is associated with viral clearance, ntAB are not a pre-requisite for infection control, since they can be absent during resolving infection.

TABLE 1

| | AA Pos | S52 Cons | A3 | A4 | A21 | A34 | A35 | B3 | B5 | B6 | B7 | B8 | C8 | C11 | C12 | C13 | C17 | C19 | D6 | D10 | D11 | D13 | D17 |
|---|---|---|---|---|---|---|---|---|---|---|---|---|---|---|---|---|---|---|---|---|---|---|---|
| Core | 29 | Q | • | P | • | • | • | | | | | | | | | | | | | | | | |
| | 57 | Q | • | • | R | • | • | | | | | | | | | | | | | | | | |
| E1 | 233 | G | • | D | • | • | D | | | | | | | | | | | | | | | | |
| | 237 | T | M | • | M | • | • | | | | | | | | | | | | | | | | |
| | 327 | S | • | • | P | • | • | | | | | | | | | | | | | | | | |
| | 381 | Y | • | • | • | • | C | | | | | | | | | | | | | | | | |
| B2 | 434 | N | • | S | • | • | • | | | | | | | | | | | | | | | | |
| | 436 | T | A | • | • | • | • | | | | | | | | | | | | | | | | |
| | 437 | S | • | • | • | • | S | | | | | | | | | | | | | | | | |
| | 448 | N | • | • | • | T | • | | | | | | | | | | | | | | | | |
| | 466 | R | • | • | • | K | • | | | | | | | | | | | | | | | | |
| | 482 | D | • | A | • | • | • | | | | | | | | | | | | | | | | |
| | 491 | A | • | • | • | P | • | | | | | | | | | | | | | | | | |
| | 496 | S | • | • | • | D | • | | | | | | | | | | | | | | | | |
| | 525 | R | K | • | K | • | • | | | | | | | | | | | | | | | | |
| | 534 | E | • | K | • | • | D | | | | | | | | | | | | | | | | |
| | 579 | P | • | • | • | Q | H | | | | | | | | | | | | | | | | |
| | 580 | E | • | • | • | K | K | | | | | | | | | | | | | | | | |
| | 583 | T | • | • | • | S | S | | | | | | | | | | | | | | | | |
| | 584 | D | • | • | • | H | H | | | | | | | | | | | | | | | | |
| | 651 | N | • | • | • | S | • | | | | | | | | | | | | | | | | |
| p7 | 767 | G | • | E | • | • | • | | | | | | | | | | | | | | | | |
| | 793 | I | • | • | V | • | • | | | | | | | | | | | | | | | | |
| | 795 | G | S | • | S | • | • | | | | | | | | | | | | | | | | |
| NS2 | 830 | A | • | V | • | • | • | | | | | | | | | | | | | | | | |
| | 849 | M | • | • | • | I | I | | | | | | | | | | | | | | | | |
| | 857 | C | R | • | • | • | • | | | | | | | | | | | | | | | | |
| | 875 | S | • | • | • | C | C | | | | | | | | | | | | | | | | |
| | 879 | V | • | • | • | I | • | | | | | | | | | | | | | | | | |
| | 902 | I | • | • | • | M | M | | | | | | | | | | | | | | | | |
| | 923 | V | • | A | • | • | • | | | | | | | | | | | | | | | | |
| | 935 | M | • | T | • | • | • | | | | | | | | | | | | | | | | |
| | 971 | K | • | • | • | R | R | | | | | | | | | | | | | | | | |
| NS3 | 1058 | R | | | | | | • | • | • | • | K | | | | | | | | | | | |
| | 1094 | K | | | | | | • | • | • | • | P | | | | | | | | | | | |
| | 1206 | T | | | | | | • | • | I | • | • | | | | | | | | | | | |
| | 1211 | A | | | | | | • | • | • | • | T | | | | | | | | | | | |
| | 1213 | S | | | | | | • | • | • | • | P | | | | | | | | | | | |
| | 1224 | A | | | | | | • | • | • | • | T | | | | | | | | | | | |
| | 1378 | E | | | | | | • | • | • | V | • | | | | | | | | | | | |
| | 1388 | I | | | | | | • | • | • | • | T | | | | | | | | | | | |
| | 1409 | V | | | | | | • | • | L | • | • | | | | | | | | | | | |
| | 1521 | V | | | | | | • | A | • | • | • | | | | | | | | | | | |
| | 1613 | T | | | | | | • | • | • | • | • | • | M | • | • | • | M | | | | | |
| | 1647 | V | | | | | | | | | | | • | T | • | • | • | T | | | | | |
| NS4A | 1714 | M | | | | | | | | | | | • | • | • | • | V | • | | | | | |

TABLE 1-continued

| Region | AA Pos | Cons | | | | | | | | | | | | | | | |
|---|---|---|---|---|---|---|---|---|---|---|---|---|---|---|---|---|---|
| NS4B | 1755 | I | | | | | | | | • | M | • | • | • | M | | |
| | 1917 | G | | | | | | | | • | • | • | • | • | R | | |
| NS5A | 1996 | D | | | | | | | N | • | • | • | • | • | • | | |
| | 2021 | Y | | | | | | | | • | • | • | • | • | C | | |
| | 2057 | M | | | | | | | | • | T | • | • | • | T | | |
| | 2059 | A | | | | | | | | • | • | • | • | V | • | | |
| | 2062 | W | | | | | | | | • | • | • | • | R | • | | |
| | 2079 | C | | | | | | | | • | • | • | • | • | Y | | |
| | 2289 | A | | | | | | | | • | T | • | • | • | T | | |
| | 2360 | T | | | | | | | | • | S | • | • | • | S | | |
| | 2377 | S | | | | | | | | • | F | • | • | • | F | | |
| | 2382 | R | | | | | | | | • | K | • | • | • | K | | |
| | 2426 | S | | | | | | | | | | • | N | • | • | N |
| NS5B | 2480 | R | | | | | | | | | | • | • | K | K | • |
| | 2526 | S | | | | | | | | | | P | • | • | • | • |
| | 2542 | S | | | | | | | | | | A | • | • | • | • |
| | 2639 | T | | | | | | | | | | • | • | • | • | A |
| | 2650 | D | | | | | | | | | | • | • | • | • | G |
| | 2734 | K | | | | | | | | | | • | • | R | • | • |
| | 2736 | A | | | | | | | | | | • | V | • | • | • |
| | 2894 | V | | | | | | | | | | A | • | • | • | • |

Amino acid positions with genetic heterogeneity of S52 in chimpanzee acute phase plasma pool.

Four overlapping RT-PCR fragments, spanning the complete ORF, and covering (i) aa 1-1019, (ii) aa 1008-1615, (iii) aa 1576-2419, and (iv) aa 2398-3020, were subcloned and analysed. AA Position numbers (AA Pos) refer to pS52. Positions with genetic heterogeneity between clones are shown. Dots represent conserved residues compared to the S52 consensus (S52 Cons) sequence. For non-conserved residues, the aa found at this position is given. Amino acid changes due to defective genomes were not considered to reflect naturally occurring genetic heterogeneity and are therefore not shown: Amino acid frameshift due to nt insertions (nt 6761.1 in clone C8 and nt 9118.1 in clone D17); stop codon (nt change G5618A in clone C19). Grey shadings indicate a minor quasispecies subpopulation, because 2/5 clones of fragment (i), 1/5 clones of fragment (ii), and 2/6 clones of fragment (iii) differed significantly from the majority of clones obtained by subcloning these fragments.

TABLE 2

| | AA Pos | ED43 Cons | A1 | A81 | A41 | A55 | C3 | C5 | C2 | C4 | C1 |
|---|---|---|---|---|---|---|---|---|---|---|---|
| Core | 20 | M | V | ● | ● | ● | | | | | |
| | 50 | R | ● | ● | Q | ● | | | | | |
| | 55 | R | ● | ● | ● | W | | | | | |
| | 79 | P | ● | ● | L | ● | | | | | |
| | 159 | E | V | ● | ● | ● | | | | | |
| | 174 | F | ● | ● | ● | P | | | | | |
| E1 | 193 | N | ● | S | ● | ● | | | | | |
| | 226 | C | R | ● | ● | ● | | | | | |
| | 265 | M | ● | ● | T | ● | | | | | |
| | 269 | A | T | ● | ● | ● | | | | | |
| | 311 | G | ● | ● | ● | R | | | | | |
| | 333 | V | ● | ● | A | ● | | | | | |
| | 367 | N | ● | ● | ● | S | | | | | |
| | 371 | V | ● | A | ● | ● | | | | | |
| E2 | 472 | L | P | ● | ● | ● | | | | | |
| | 501 | S | ● | ● | F | ● | | | | | |
| | 529 | T | N | ● | ● | ● | | | | | |
| | 616 | W | ● | ● | ● | R | | | | | |

TABLE 2-continued

| | AA Pos | ED43 Cons | A1 | A81 | A41 | A55 | C3 | C5 | C2 | C4 | C1 |
|---|---|---|---|---|---|---|---|---|---|---|---|
| | 621 | T | A | ● | ● | ● | | | | | |
| | 658 | D | ● | ● | ● | V | | | | | |
| | 692 | L | ● | ● | ● | F | | | | | |
| pT | 756 | A | ● | ● | V | ● | | | | | |
| | 765 | F | ● | ● | ● | S | | | | | |
| | 768 | A | V | ● | ● | ● | | | | | |
| NS2 | 826 | L | ● | ● | ● | P | | | | | |
| | 854 | E | ● | K | ● | ● | | | | | |
| | 861 | I | ● | ● | ● | V | | | | | |
| | 921 | I | ● | V | ● | ● | | | | | |
| | 990 | T | ● | S | ● | ● | | | | | |
| | 1018 | E | ● | ● | V | ● | | | | | |
| NS3 | 1041 | S | ● | G | ● | ● | | | | | |
| | 1112 | P | S | ● | ● | ● | | | | | |
| | 1193 | V | ● | A | ● | ● | | | | | |
| | 1254 | L | ● | ● | H | ● | | | | | |
| | 1327 | L | ● | P | ● | ● | | | | | |
| | 1484 | R | ● | ● | C | ● | | | | | |
| | 1493 | R | ● | K | ● | ● | | | | | |
| | 1519 | E | ● | ● | ● | G | | | | | |
| | 1526 | A | ● | ● | V | ● | | | | | |
| | 1551 | C | ● | ● | R | ● | | | | | |
| | 1554 | H | R | ● | ● | ● | | | | | |
| | 1566 | T | ● | ● | ● | A | | | | | |
| | 1577 | K | ● | ● | E | ● | | | | | |
| | 1583 | F | ● | ● | S | ● | | | | | |
| NS4A | 1675 | L | ● | ● | ● | P | | | | | |
| | 1688 | L | ● | R | ● | ● | | | | | |
| NS4B | 1713 | K | E | ● | ● | ● | ● | ● | ● | ● | ● |
| | 1791 | M | | | | | ● | T | ● | ● | ● |
| | 1885 | A | | | | | ● | T | ● | ● | ● |
| | 1905 | H | | | | | ● | ● | R | ● | ● |
| | 1954 | T | | | | | ● | ● | P | ● | ● |
| NS5A | 2088 | E | | | | | ● | ● | ● | ● | G |
| | 2130 | L | | | | | ● | ● | ● | ● | I |
| | 2369 | T | | | | | ● | I | ● | ● | ● |
| NS5B | 2455 | Y | | | | | H | ● | ● | ● | ● |
| | 2461 | S | | | | | P | ● | ● | ● | ● |
| | 2547 | N | | | | | ● | ● | ● | D | ● |
| | 2571 | R | | | | | ● | ● | W | ● | ● |
| | 2582 | L | | | | | ● | ● | ● | ● | P |
| | 2627 | S | | | | | ● | ● | ● | ● | P |
| | 2750 | N | | | | | ● | ● | S | ● | ● |
| | 2806 | E | | | | | G | ● | ● | ● | ● |

TABLE 2-continued

| AA Pos | ED43 Cons | A1 | A81 | A41 | A55 | C3 | C5 | C2 | C4 | C1 |
|---|---|---|---|---|---|---|---|---|---|---|
| 2884 | H | | | | Q | ● | ● | ● | ● | |
| 2935 | A | | | | | ● | ● | ● | ● | V |

Amino acid positions with genetic heterogeneity of ED43 in chimpanzee acute phase plasma pool.

Two overlapping RT-PCR fragments, covering (i) aa 1-1763, and (ii) aa 1713-3008, were subcloned and analysed. AA Position numbers (AA Pos) refer to pED43. Positions with genetic heterogeneity between clones are indicated. Dots represent conserved residues compared to the ED43 consensus (ED43 cons) sequence. For non-conserved residues, the aa found at this position is given. A stop codon (resulting from nt change at position 1930 in clone A41) was not considered to reflect naturally occurring genetic heterogeneity and is not shown.

REFERENCES

Gottwein, J. M., T. K. Scheel, A. M. Hoegh, J. B. Lademann, J. Eugen-Olsen, G. Lisby, and J. Bukh, 2007, Robust hepatitis C genotype 3a cell culture releasing adapted intergenotypic 3a/2a (S52/JFH1) viruses: Gastroenterology, v. 133, no. 5, p. 1614-1626.

Gottwein, J. M., T. K. Scheel, T. B. Jensen, J. B. Lademann, J. C. Prentoe, M. L. Knudsen, A. M. Hoegh, and J. Bukh, 2009, Development and characterization of hepatitis C virus genotype 1-7 cell culture systems: role of CD81 and scavenger receptor class B type I and effect of antiviral drugs: Hepatology., v. 49, no. 2, p. 364-377.

Jensen, T. B., J. M. Gottwein, T. K. Scheel, A. M. Hoegh, J. Eugen-Olsen, and J. Bukh, 2008, Highly efficient JFH1-based cell-culture system for hepatitis C virus genotype 5a: failure of homologous neutralizing-antibody treatment to control infection: J Infect. Dis., v. 198, no. 12, p. 1756-1765.

Kaul, A., I. Woerz, P. Meuleman, G. Leroux-Roels, and R. Bartenschlager, 2007, Cell culture adaptation of hepatitis C virus and in vivo viability of an adapted variant: J Virol.

Kolykhalov, A. A., E. V. Agapov, K. J. Blight, K. Mihalik, S. M. Feinstone, and C. M. Rice, 1997, Transmission of hepatitis C by intrahepatic inoculation with transcribed RNA: Science, v. 277, no. 5325, p. 570-574.

Lindenbach, B. D. et al., 2005, Complete replication of hepatitis C virus in cell culture: Science, v. 309, no. 5734, p. 623-626.

Lindenbach, B. D. et al., 2006, Cell culture-grown hepatitis C virus is infectious in vivo and can be recultured in vitro: Proc Natl Acad Sci USA, v. 103, no. 10, p. 3805-3809.

Pietschmann, T. et al., 2006, Construction and characterization of infectious intragenotypic and intergenotypic hepatitis C virus chimeras: Proc Natl Acad Sci USA, v. 103, no. 19, p. 7408-7413.

Scheel, T. K., J. M. Gottwein, T. B. Jensen, J. C. Prentoe, A. M. Hoegh, H. J. Alter, J. Eugen-Olsen, and J. Bukh, 2008, Development of JFH1-based cell culture systems for hepatitis C virus genotype 4a and evidence for cross-genotype neutralization: Proc. Natl. Acad. Sci. U.S.A., v. 105, no. 3, p. 997-1002.

Wakita, T. et al., 2005, Production of infectious hepatitis C virus in tissue culture from a cloned viral genome: Nat Med, v. 11, no. 7, p. 791-796.

Yanagi, M., R. H. Purcell, S. U. Emerson, and J. Bukh, 1997, Transcripts from a single full-length cDNA clone of hepatitis C virus are infectious when directly transfected into the liver of a chimpanzee: Proc Natl Acad Sci USA, v. 94, no. 16, p. 8738-8743.

Yanagi, M., C. M. St, M. Shapiro, S. U. Emerson, R. H. Purcell, and J. Bukh, 1998, Transcripts of a chimeric cDNA clone of hepatitis C virus genotype 1b are infectious in vivo: Virology, v. 244, no. 1, p. 161-172.

Yi, M., Y. Ma, J. Yates, and S. M. Lemon, 2007, Compensatory mutations in E1, p7, NS2, and NS3 enhance yields of cell culture-infectious intergenotypic chimeric hepatitis C virus: J Virol, v. 81, no. 2, p. 629-638.

Zhong, J. et al., 2005, Robust hepatitis C virus infection in vitro: Proc Natl Acad Sci USA, v. 102, no. 26, p. 9294-9299.

What is claimed is:

1. An isolated nucleic acid molecule comprising a mutated human hepatitis C virus genome of genotype 3a wherein said molecule encodes a nucleic acid sequence according to SEQ ID NO:3 wherein all of the sequences encoding the E1 gene, E2 gene, P7 gene, and NS2 gene sequences are deleted, a part of the Core gene sequence is deleted, and a heterologous reporter gene sequence is inserted, and wherein HCV genomic portions of the molecule with the deletions have a sequence identity of at least 98% to a reference SEQ ID NO:3 sequence wherein all of the E1 gene, E2 gene, P7 gene and NS2 gene sequences are deleted and wherein said part of said Core gene sequence is deleted.

2. The nucleic acid molecule according to claim 1, wherein said molecule encoding the mutated human hepatitis C virus of genotype 3a encodes the amino acid sequence that has a sequence identity of at least 98% to that of a reference SEQ ID NO:1 sequence wherein all of the E1, E2, P7, and NS2 amino acid sequences are deleted and part of the Core amino acid sequence is deleted.

3. The nucleic acid molecule according to claim 1, wherein said molecule when encoding human hepatitis C virus of genotype 3a has a sequence identity of at least 99% to the reference SEQ ID NO: 3 sequence wherein nucleic acid sequences encoding all of the E1, E2, P7, and NS2 genes are deleted and part of the Core gene sequence is deleted.

4. A DNA construct comprising a nucleic acid molecule according to claim 1.

5. An RNA transcript of the DNA construct according to claim 4 which encodes the mutated human hepatitis C virus genome of genotype 3a.

6. A cell transfected with the DNA construct of claim 4.

7. A cell transfected with the RNA transcript according to claim 5.

8. A method for producing a mutated hepatitis C virus genome comprising transfecting a host cell with the RNA transcript according to claim 5.

9. A method for assaying candidate antiviral agents for activity against HCV, comprising: a) exposing a cell containing the mutated hepatitis C virus genome according to claim 1 to the candidate antiviral agent; and b) measuring the presence or absence of hepatitis C virus replication or correlates thereof in the cell of step (a).

10. The method according to claim 9, wherein said replication in step (b) is measured by at least one of the following: negative strand RT-PCR, quantitative RT-PCR, Western blot, immunofluorescence, reporter gene activity, or non-fluorescent immuno-staining.

11. A method for determining the susceptibility of cells in vitro to support HCV replication, comprising the steps of: a) growing animal cells in vitro; b) transfecting into said cells the nucleic acid according to claim 1; and c) determining if said cells show indicia of HCV replication.

12. The method according to claim 11, wherein said cells are human cells.

13. The method according to claim 11, wherein said replication in step (c) is measured by at least one of the following reverse transcriptase-polymerase chain reaction (RT-PCR), Western blot, immunofluorescence, or reporter gene activity.

* * * * *